(12) United States Patent
Eldridge

(10) Patent No.: US 7,612,045 B2
(45) Date of Patent: Nov. 3, 2009

(54) COMPOUNDS, COMPOSITIONS AND METHODS FOR CONTROLLING BIOFILMS AND BACTERIAL INFECTIONS

(75) Inventor: Gary R. Eldridge, St. Louis, MO (US)

(73) Assignee: Sequoia Sciences, Inc., St. Louis, MO (US)

( * ) Notice: Subject to any disclaimer, the term of this patent is extended or adjusted under 35 U.S.C. 154(b) by 355 days.

(21) Appl. No.: 11/662,806

(22) PCT Filed: Sep. 14, 2005

(86) PCT No.: PCT/US2005/032874

§ 371 (c)(1),
(2), (4) Date: Mar. 13, 2007

(87) PCT Pub. No.: WO2006/031943

PCT Pub. Date: Mar. 23, 2006

(65) Prior Publication Data

US 2008/0145322 A1    Jun. 19, 2008

(51) Int. Cl.
*A61K 31/70* (2006.01)
*A61K 31/65* (2006.01)
*A61K 31/195* (2006.01)
*A61K 8/18* (2006.01)

(52) U.S. Cl. ............................. 514/31; 514/34; 514/37; 514/39; 514/41; 514/152; 514/154; 514/561; 424/49

(58) Field of Classification Search ............... 514/31, 514/34, 37, 39, 41, 152, 154, 561; 424/49
See application file for complete search history.

(56) References Cited

U.S. PATENT DOCUMENTS

| | | | |
|---|---|---|---|
| 3,996,132 A | 12/1976 | Mateos et al. | |
| 4,606,911 A | 8/1986 | Hayashi et al. | |
| 4,897,268 A | 1/1990 | Tice et al. | |
| 4,929,365 A | 5/1990 | Clark et al. | |
| 5,075,109 A | 12/1991 | Tice et al. | |
| 5,312,813 A | 5/1994 | Costerton et al. | |
| 5,462,644 A | 10/1995 | Woodson | |
| 5,789,239 A | 8/1998 | Eyers et al. | |
| 5,834,437 A | 11/1998 | Jew et al. | |
| 5,882,916 A | 3/1999 | Wiersma | |
| 5,906,825 A | 5/1999 | Seabrook et al. | |
| 5,985,601 A | 11/1999 | Ni et al. | |
| 6,080,323 A | 6/2000 | Yu et al. | |
| 6,264,926 B1 | 7/2001 | Farooqi et al. | |
| 6,267,897 B1 | 7/2001 | Robertson et al. | |
| 6,267,979 B1 | 7/2001 | Raad et al. | |
| 6,369,101 B1 | 4/2002 | Carlson | |
| 6,395,189 B1 | 5/2002 | Fabri et al. | |
| 6,399,115 B2 | 6/2002 | Revel | |
| 6,410,256 B1 | 6/2002 | Ceri et al. | |
| 6,423,219 B1 | 7/2002 | Chandler | |
| 6,455,031 B1 | 9/2002 | Davies et al. | |
| 6,468,549 B1 | 10/2002 | Dupuis et al. | |
| 6,498,862 B1 | 12/2002 | Pierson et al. | |
| 6,555,055 B1 | 4/2003 | Cisar et al. | |

(Continued)

FOREIGN PATENT DOCUMENTS

| WO | WO 98/08091 A1 | 2/1998 |
|---|---|---|
| WO | WO 2006/010147 A2 | 1/2006 |
| WO | WO 2006/019881 A2 | 2/2006 |
| WO | WO 2006/019926 A2 | 2/2006 |
| WO | WO 2006/031943 A1 | 3/2006 |
| WO | WO 2006/102255 A1 | 9/2006 |

OTHER PUBLICATIONS

International Search Report for PCT/US2006/032874, published by the International Bureau of WIPO on Feb. 20, 2006 under WO 2006/031943.

(Continued)

*Primary Examiner*—Raymond J Henley, III
(74) *Attorney, Agent, or Firm*—Kenneth Solomon; Gallop, Johnson & Neuman, L.C.

(57) ABSTRACT

The present invention provides compounds and compositions useful for controlling bacterial biofilms as well as for controlling and/or preventing bacterial infections. The compounds of the invention are pentacyclic acid triterpenes. Methods for controlling biofilms and for controlling and/or preventing bacterial infections are also disclosed.

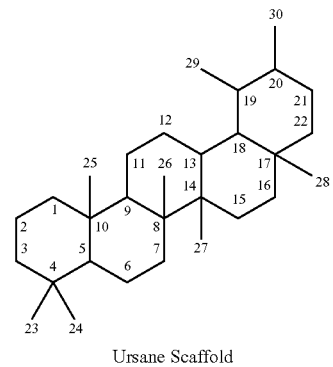

Ursane Scaffold

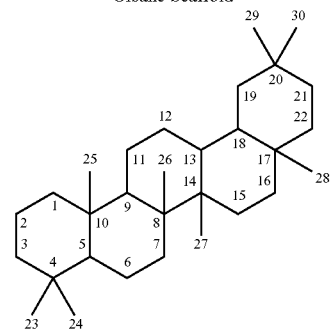

Oleanane Scaffold

57 Claims, 6 Drawing Sheets

U.S. PATENT DOCUMENTS

| | | |
|---|---|---|
| 6,585,961 B1 | 7/2003 | Stockel |
| 6,596,505 B2 | 7/2003 | Ceri et al. |
| 6,669,929 B1 | 12/2003 | Boyd et al. |
| 6,762,160 B2 | 7/2004 | Barbeau et al. |
| 6,946,124 B2 | 9/2005 | Arnaud-Sebillotte et al. |
| 7,098,227 B2 | 8/2006 | Dunkel et al. |
| 7,326,542 B2 | 2/2008 | Bassler et al. |
| 2002/0037260 A1 | 3/2002 | Budny et al. |
| 2003/0225126 A1 | 12/2003 | Markham et al. |
| 2004/0033549 A1 | 2/2004 | Greenberg et al. |
| 2004/0136924 A1 | 7/2004 | Boyd et al. |
| 2005/0137259 A1 | 6/2005 | Matsuyama et al. |
| 2006/0014285 A1 | 1/2006 | Eldridge et al. |
| 2006/0014290 A1 | 1/2006 | Eldridge |
| 2006/0228384 A1 | 10/2006 | Eldridge |
| 2006/0264411 A1 | 11/2006 | Eldridge |
| 2007/0014739 A1 | 1/2007 | Eldridge et al. |

OTHER PUBLICATIONS

Bannon, C. D., et al., Chlorination of olean-12-enes, Australian Journal of Chemistry, 1975, 2649-2654, 28(12).

Begum, S., et al., Chemical constituents from the leaves of Psidium guajava, Natural Product Research, 2004, 135-140, 18(2), Taylor & Francis Ltd.

Bowden, et al., Aust. J. Chem., 1975, 91-103, 28.

Brieskorn, C. H., and Eschelbach, H., Glykamine von Ursol- und 18β-Glycyrrhetinsaure, Arch. Pharm. (Weinheim), 1979, 752-762, 312.

Drefahl, G. and Huneck, S., Uber Reduktinosprodukte verschiedener Triterpenoxime und Triterpensaureamide, Chem. Ber., 1960, 1967-1975, Verlag Chemie Gmbh.

Drefahl, G. and Huneck, S., Chem. Ber., 1961, 1145-1150, 94.

Fried, J., et al., Structure-Activity Relationships in the Field of Antibacterial Steroid Acids, Journal of Medicinal Chemistry, Apr. 20, 1965, 279-282, 8(3), American Chemical Society.

Garcia-Granados, A., et al., Epoxides, Cyclic Sulfites, and Sulfate from Natural Pentacyclic Triterpenoids: Theoretical Calculations and Chemical Transformations, J. Org. Chem., 2003, 4833-4844, 68(12).

Hichri, F., et al., Antibacterial activities of a few prepared derivatives of oleanolic acid and of other natural triterpenic compounds, C. R. Chimie, 2003, 473-483, 6, Elsevier S.A.S.

Isobe, T., et al., Studies of the constituents of Leucoseptrum stellipillum, Yakugaku Zasshi, 1989, 175-178, 109(3), Japan.

Jain, S. M. and Atal, C. K., Indian J. Chem. Sect. B., 1986, 427-428, 25.

Linde, H., Zur Synthese einiger stickstoffhaltiger Oleanol- und Ursolsaurederivate, Arch. Pharm. (Weinheim), 1979, 832-837, 312.

Ma, C., et al., Chemical Modification of Oleanene Type Triterpenes and Their Inhibitory Activity against HIV-1 Protease Dimerization, Chem. Pharm. Bull., 2000, 1681-1688, 48(11).

Ojinnaka, C. M. and Okogun, J. I., The chemical constituents of Musanga cecropioides, Journal of Natural Products, 1985, 337, 48(2).

Osawa, K., et al., Antibacterial and antihemolytic activity of triterpenes and .beta.-sitosterol isolated from Chinese Quince (Chaenomeles sinensis), Natural Medicines, 1997, 365-367, 51(4), Japanese Society of Pharmacognosy, Japan.

Ren, D., et al., Differential Gene Expression for Investigation of Escherichia coli Biofilm Inhibition by Plant Extract Ursolic Acid, Applied and Environmental Microbiology, Jul. 2005, 4022-4034, 71(7).

Takechi, M. and Tanaka, Y., Structure-Activity Relationships of Synthetic Methyl Ursolate Glycosides, Phytochemistry, 1993, 675-677, 34(3), Pergamon Press Ltd., Great Britain.

Tamura, Y., et al., Antimicrobial activities of saponins of pericarpe of Sapindus mukurossi on dermatophytes, Natural Medicines, 2001, 11-16, 55(1), Japanese Society of Pharmacognosy, Japan.

Wang, M., et al., Studies on chemical constituents from root of Rubus innominatus, Zhongcaoyao, 2003, 295-297, 34(4), Zhongcaoyao Zazhi Bianjibu, China.

Wrzeciono, et al., Rocz. Chem., 1973, 955, 956, 960, 961, 47.

Greiner, L. et al., Biofilm Formation by Neisseria gonorrhoeae, Infect. And Immun., Apr. 2005, 73(4), pp. 1964-1970.

Greiner, L. C. et al., Nontypeable Haemophilus influenzae Strain 2019 Produces a Biofilm Containing N-Acetylneuraminic Acid that may Mimic Sialylated O-Linked Glycans, Infect. and Immun., Jul. 2004, 72(7), pp. 4249-4260.

Hall-Stoodley, Luanne et al., Bacterial biofilms: From the natural environment to infectious diseases, Nature Reviews Microbiology, Feb. 2004, vol. 2, No. 2, pp. 95-108.

Hanna, H. A. et al., Antibiotic-Impregnated Catheters Associated with Significant Decrease in Nosocomial and Multidrug-Resistant Bacteremias in Critically Ill Patients, Chest, 2003, 124(3), pp. 1030-1038.

Hardy, G. et al., The Pathogenesis of Disease Due to Nontypeable Haemophilus influenzae, Methods Mol. Med., 2007, 71, M. Herbort © Humana Press Inc., Totawa, NJ, USA, pp. 1-28.

Harrison-Balestra, C. et al., A Wound-isolated Pseudomonas aeruginosa Grows a Biofilm in Vitro within 10 hours and is Visualized by light Microscopy, Dermatol Surg, 2003, 29, pp. 631-635.

Hesse, H. et al., Molecular analysis and control of cysteine biosynthesis: intergration of nitrogen and sulphur metabolism, J. Exp. Bot., Jun. 2004, 55(401), pp. 1283-1292.

Hogema, B. M. et al., Inducer exlusion in Escherichia coli by non-PTS substrates: the role of the PEP to pyruvate ratio in determining the phosphorylation state of enzyme IIAGlc, Molecular Microbiology, 1998, vol. 30(3), Blackwell Science Ltd., pp. 487-498.

Honda, T. et al., Design and Synthesis of 2-Cyano-3, 12-Dioxoolean-1, 9-Dien-28-Oic Acid, a Novel and Highly Active Inhibitor of Nitric Oxide Production in Mouse Macrophages, Bioorganic & Medicinal Chemistry Letters, 1998, 8, pp. 2711-2714.

Honda, T. et al., New Enone Derivatives of Oleanolic Acid and Ursolic Acid as Inhibitors of Nitric Oxide Production in Mouse Macrophages, Bioorganic & Medicinal Chemistry Letters, 1997,7(13), pp. 1623-1628.

Honda, T. et al., Novel Synthetic Oleanane Triterpenoids: A Series of Highly Active Inhibitors of Nitric Oxide Production in Mouse Macrophages; Bioorganic & Medicinal Chemistry Letters, Elsevier Science Ltd., 1999, 9, pp. 3429-3434.

Howell-Jones, R. S. et al., A review of the microbiology, antibiotic usage and resistance in chronic skin wounds, J. Antimicrob. Ther., Jan. 2005, 55(2), pp. 143-149.

Hsu, H. et al., Methods of Decocting and Administering Herbal Drugs, and 382, Centellae Herba, Oriental Materia Medica: A Concise Guide, Oriental Healing Arts Institute, 1986, pp. 39-40 and 443-444.

Hsu, Y. et al., Proliferative inhibition, cell-cycle dysregulation, and induction of apoptosis by ursolic acid in human non-small cell lung cancer A549 cells, Life Sci., Sep. 24, 2004, 75, pp. 2303-2316.

Hu, J. F. et al., Antibacterial, Partially Acetylated Obigorhamnosides from Cleistopholis patens, J. Nat. Prod., American Chemical Society and American Society of Pharmacognosy, 2006, 69, pp. 585-590.

Hu, J. F. et al., Cyclolignans from Scyphocephalium ochocoa via high-throughput natural product chemistry methods; Phytochemistry, Elsevier Ltd., 2005, 66, pp. 1077-1082.

Hu, J. F. et al., Application of Capillary-scale Nmr for the Structure Determination of Phytochemicals, Phytochem. Anal., John Wiley.& Sons, Ltd., 2005, 16, pp. 127-133.

Hu, J. F. et al., Miniaturization of the Structure Elucidation of Novel Natural Products - Two Trace Antibacterial Acylated Caprylic Alcohol Gylcosides from Arctostaphylosis pumila, Planta Med., 2005, 71, pp. 176-180.

Huang, a. X. et al., An Exceptionally Short and Simple Enantioselective Total synthesis of Pentacyclic Triterpenes of the β-Amyrin Family, J. Am. Chem. Soc., 1999, 121, pp. 9999-10003.

Ikuta, A. et al., Ursane- and Oleannane-Type Triterpenes from Ternstroemia gymnanthera Callus Tissues, J. Nat. Prod., 2003, 66, pp. 1051-1054.

Jackson, D. W. et al., Biofilm Formation and Dispersal under the Influence of the Global Regulator CsrA of Escherichia coli, Journal of Bacteriology, Jan. 2002, vVol. 184, No. 1, pp. 290-301.

Jackson, D. et al., Catabolite Repression of Escherichia coli Biofilm Formation, Journal of Bacteriology, Jun. 2002, 184(12), pp. 3406-3410.

Jarrett, C. O. et al., Transmission of Yersinia pestis from an Infectious Biofilm in the Flea Vector, JID, Aug. 15, 2004, 190, pp. 783-792.

Jones, S. M. et al., Effect of vancomycin and rifampicin on methicillin-resistant Staphylococcus aureus biofilms, Lancet, 2001, 357, pp. 40-41.

Justice, S. et al., Differentiation and developmental pathways of uropathogenic Escherichia coli in urinary tract pathogenesis, PNAS, Feb. 3, 2004, 101(5), pp. 1333-1338.

Kaplan, J. B. Methods for the treatment and prevention of bacterial biofilms, Expert Opinion on Therapeutic Patents, Ashley Publications, GB, 2005, vol. 15, No. 8, pp. 955-965.

Kartnig, T., Clinical Application of Centella asiatica (L.) Urb., Herbs, Spices and Medicinal Plants, Oryx Press, Arizona, USA, 1998, 3, pp. 145-173.

Kaufman, P. B. et al., Phytochemicals: the Chemical Components of Plants and Bioseparation of Compounds, Chapters 1 and 7, Natural Products from Plants, CRC Press LLC, Boca Raton, USA, 1999, pp. 1-36 and 207-240.

Kiley, P. J. and Beinert, H., The role of Fe-S proteins in sensing and regulation in bacteria, Current Opinion in . Microbiology, www.currentopinion.com, 2003, vol. 6, pp. 181-185.

Konoike, T. et al., Synthesis of [2- 13C]-Oleanolic Acid and [2-13C]-Myriceone, Tetrahedron, 1999, 55, pp. 14901-14914.

Landa, A. S. et al., Efficacy of Ophthalmic Solutions to Detach Adhering Pseudomonas aeruginosa from Contact Lenses, Cornea, 1998, 17(3), pp. 293-300.

Lavender, H. F. et al., Biofilm Formation in Vitro and Virulence in Vivo of Mutants of Klebsiella pneumonia, Infect, and Immun., Aug. 2004, 72(8), pp. 4888-4890.

Leroy-Dudal, J. et al., Role of $\alpha v \beta 5$ intergrins and vitronectin in Pseudomonas aeruginosa PAK interaction with A549 respiratory cells, Microbes and Infection, 2004, 6, pp. 875-881.

Leyh, T. et al., The DNA Sequence of the Sulfate Activation Locus from Escherichia coli K-12, The Journal of Biological Chemistry, May 25, 1992, 267(15), pp. 10405-10410.

Li, Yung-Hua et al., Natural Genetic Transformation of Streptococcus mutans Growing in Biofilms, J. Bacteriol., Feb. 2001, 183(3), pp. 897-908.

Liaw, Shwu-Jen. et al., Modulation of swarming and virulence by fatty acids through the RsbA Protein in Proteus mirabilis, Infect. Immun., Dec. 2004, 72(12), pp. 6836-6845.

Lilic, M. et al., Identification of the CysB-regulated gene, hsIJ, related to the Escherichia coli novobiocin resistance phenotype, FEMS Microbiology Letters, 2003, 224, pp. 239-246.

Lipsky, Benjamin A., Medical Treatment of Diabetic Foot Infections, CID, 2004, 39 (Supp.2), pp. S104-S114.

Little, C. S. et al., Age Alterations in Extent and Severity of Experimental Intranasal Infection with Chlamydophila pneumoniae in BALB/c Mice, Infection and Immunity, Mar. 2005, 73(3), pp. 1723-1734.

Lockowska, A. et al., Identification of activating region (AR) of Escherichia coli LysR-type transcription factor CysB and CysB contact site on RNA polymerase alpha subunit at the cysP promoter, Molecular Microbiology, 2004, 53(3), pp. 791-806.

Lochowska, A. et al., Functional Dissection of the LysR-type CysB Transcriptional Regulator, The Journal of Biological Chemistry, Jan. 19, 2001, 276(3), pp. 2098-2107.

Mah Thien-Fah, C. et al., Mechanism of biofilm resistance to antimicrobial agents, Trends in Microbiology, Jan. 2001, Elsevier Science, Ltd., vol. 9, No. 1, pp. 34-39.

Maki, D. G. et al., Prevention of Central Venous Catheter-Related Bloodstream Infection by Use of an Antiseptic-Impregnated Catheter, Ann. Int. Med., 1997, 127(4), pp. 257-266.

Martinez, J. J. et al., Type 1 pilus-mediated bacterial invasion of bladder epithelial cells, The EMBO Journal, 2000, 19(12), pp. 2803-2812 (Abstract).

Martinez, J. J. and Hultgren, S. J., Requirement of Rho-family GTPases in the invasion of Type 1-piliated uropathogenic Escherichia coli, Cellular Microbiology, 2002, 4(1), pp. 19-28.

Mclaughlin-Borlace, L. et al., Bacterial biofilm on contact lenses and in lens storage cases in wearers with microbial keratitis, J. of Applied Microbiology, 1998, 84, pp. 827-838.

Menzies, B. E., The role of fibronectin binding proteins in the pathogenesis of Staphylococcus aureus infections, Curr. Opin. Infect. Dis., 2003, 16, pp. 225-229.

Mi, Y. et al., Total Synthesis of (+)-$\alpha$-Onocerin in Four Steps via Four-Component Coupling and Tetracyclization Steps, J. Am. Chem. Soc., 2002, 124, pp. 11290-11291.

Miranda-Vizuete, A. et. al., The Levels of Ribonucleotide Reductase, Thioredoxin, Glutaredoxin 1, and GSH are Balanced in Escherichia coli K12, The Journal of Biological Chemistry, The American Society for Biochemistry and Molecular Biology, Inc., USA, Aug. 9, 1996, vol. 271, No. 32, pp. 19099-19103.

Abe, F. et al., Ursolic acid as a trypanocidal constituent in rosemary, Biol. Pharm. Bull., Nov. 2002, 25 (11), pp. 1485-1487.

Adler and Epstein, Phosphotransferase-System Enzymes as Chemoreceptors for Certain Sugars in Escherichia coli Chemotaxis, Proc. Nat. Acad. Sci. USA, Jul. 1974, 71(7), pp. 2895-2899.

Adnyana et al., Three New Triterpenes from the Seeds of Combretum quadrangulare and their Hepatoprotective Activity, J. Nat. Prod. 2001, 64(3), pp. 360-363 (Abstract).

Akamatsu, H. et al., The inhibition of free radical generation by human neutrophils through the synergistic effects of metronidazole with palmitoleic acid: a possible mechanism of action of metronidazole in rosacea and ance, Archives of Dermatological Research, 1990, 282, pp. 449-454.

Anderson et al., Intracellular Bacterial Biofilm-Like Pods in Urinary Tract Infections, www.sciencemag.org, Jul. 4, 2003, pp. 105-107.

Anderson, K. J. et al., J. Nutr. 2001, 131, pp. 2837-2842.

Ando, E. et al., Biofilm Formation Among Methicillin-Resistant Staphylococcus Aureus Isolates from Patients with Urinary Tract Infection, Acta Med. Okayama, 2004, 58(4), pp. 207-214.

Arevalo-Ferro, C. et al., Biofilm formation of Pseudomonas putida IsoF: the role of quorum sensing as assessed by proteomics, Systematic and Applied Microbiology, 2005, 28, pp. 87-114.

Auger, S. et al., Global Expression Profile of Bacillus subtilis Grown in the Presence of Sulfate or Methionine, Journal of Bacteriology, Sep. 2002, 184(18), pp. 5179-5186.

Ballesta-Acosta, M.C. et al., A New 24-nor-Oleanase Triterpenoid from Salvia carduacea, J. Nat. Prod., 2002, 65, pp. 1513-1515.

Begum, et al., Triterpenoids from the Leaves of Eucalyptus camaldulensis var. obtusa, J. Nat. Prod. 1997, 60, pp. 20-23 (Abstract).

Beloin, C. et al., Finding gene-expression patterns in bacterial biofilms, Trends in Microbiology, Jul. 2005, Elsevier Science Ltd, vol. 13, No. 1, pp. 4022-4034.

Blast search of the cysB gene at the Microbial Genomics database at the National Center for Biotechnology Information (NCBI) of the National Institutes of Health (NIH); http://www.ncbi.nlm.nih.gov/sutils/genom_table.cgi.

Boddicker, J.D. et al., Differential binding to and biofilm formation on, HEp-2 cells by Salmonella enterica Serovar Typhimurium is dependent upon allelic variation in the fimH gene of the fim gene cluster, Molecular Microbiology, 2002, 45(5), pp. 1255-1265.

Borum, P. R. and Monty, K. J., Regulatory Mutants and Control of Cysteine Biosynthetic Enzymes in Salmonella typhimurium; Journal of Bacteriology, USA, Jan. 1976, vol. 125, No. 1, pp. 94-101.

Both, D. et al., Liposome-encapsulated ursolic acid increases ceramides and collagen in human skin cells, Arch Dermatol. Res., 2002, 293, pp. 569-575.

Burkhart, Craig N. et al., Microbiology's principle of biofilms as a major factor in the pathogenesis of acne vulgaris, International J. of Dermatology, 2003, 42, pp. 925-927.

Byrne, C. et al., DNA Sequences of the cysK Regions of Salmonella typhimurium and Escherichia coli and Linkage of the cysK Regions to ptsH, Journal of Bacteriology, Jul. 1988, 170(7), pp. 3150-3157.

Cardenas, C. et al., Effects of ursolic acid on different steps of the angiogenic process, Biochem. Biophys. Res. Commun., Jul. 23, 2004, 320, pp. 402-408.

Centers for Disease Control and Prevention, Guidelines for the Prevention of Intravascular Catheter-Related Infections, MMWR, 2002, 51: No. RR-10.

Centers for Disease Control and Prevention, Update: Investigation of Bioterrorism-Related Anthrax and Interim Guidelines for Exposure Management and Antimicrobial Therapy, Oct. 26, 2001, MMWR 2001, 50(42) pp. 909-919.

Chamber 21st Century Dictionary, Chambers Harrap Publishers Limited 2001, Retrieved Jul. 7, 2008, from http://www.credoreference.com/entry/1215201.

Chaturvedula et al., A New Ursane Triterpene from Monochaetum Vulcenicum that Inhibits DNA Polymerase $\beta$ Lyase, J. Nat. Prod. 2004, 67, pp. 889-901 (Abstract).

Coldren, C. et al., Gene Expression Changes in the Human Fibroblast Induced by Centella asiatica Triterpenoids, Planta Med., 2003, 69, pp. 725-732.

Conley, J. et al., Biofilm Formation by Group A Streptococci: Is there a Relationship with Treatment Failure?, J. Clin. Microbiol., Sep. 2003, 41(9), pp. 4043-4048.

Corey E. J. and Lee, J., Enantioselective Total Synthesis of Oleanolic Acid, Erythrodiol, β-Amyrin, and Other Pentacyclic Triterpenes from a Common Intermediate, J. Am. Chem. Soc. 1993, 115, pp. 8873-8874.

Cortès, G. et al., Role of Lung Epithelial Cells in Defense against Klebsiella pneumoniae Pneumonia, Infect. And Immun., Mar. 2002, 70(3), pp. 1075-1080.

Cossart P. and Sansonetti, P. J., Bacterial Invasion: The Paradigms of Enteroinvasive Pathogens, Science, Apr. 9, 2004, 304, pp. 242-248.

Costerton, J. W. et al., Bacterial Biofilms: A Common Cause of Persistent Infections, Science, May 21, 1999, 284, pp. 1318-1322.

Cremin, P. A. and Zeng, L., High-Throughput Analysis of Natural Product Compound Libraries by Parallel LC-MS Evaporative Light Scattering Detection, Anal. Chem., Nov. 1, 2002, 74(21), pp. 5492-5500.

Cywes, C. et al., Group A Streptococcus tissue invasion by CD44-mediated cell signaling, Nature, 2001, 414, pp. 648-652.

Darouiche, R. et al., A Comparison of Two Antimicrobial-impregnated Central Venous Catheters, New Engl. Jour. Med., 1999, 340(1), pp. 1-8.

Datsenko and Wanner, One-step inactivation of chromosomal genes in Escherichia coli K-12 using PCR products, PNAS, Jun. 6, 2000, 97(12), pp. 6640-6645.

Delic-Attree et al., Cloning, sequence and mutagenesis of the structural gene of Pseudomonas aeruginosa CysB, which can activate algD Transcription, Mol. Microbiol., 1997, 24(6), pp. 1275-1284.

Demuth, D. et al., Discrete Protein Determinant Directs the Species-Species Adherence of Porphyromonas gingivalis to Oral Streptococci, Infection and Immunity, 2001, 69(9), pp. 5736-5741.

Ding, H. and Demple, B., Thiol-Mediated Disassembly and Reassembly of [2Fe-2S] Clusters in the Redox-Regulated Transcription Factor SoxR, American Chemical Society, 1998, vol. 37 published on Web Nov. 19, 1998, pp. 17280-17286.

Donlan, Rodney M. et al., Biofilms: Survival mechanisms of clinically relevant microorganisms, Clinical Microbiology Reviews, Apr. 2002, vol. 15, No. 2, pp. 167-193.

Edwards, J. et al., The role of lipooligosaccharide in Neisseria gonorrhoeae pathogenesis of cervical epithelia: lipid a serves as a C3 acceptor molecule, Cellular Micro., 2002, 4(9), pp. 585-598.

Edwards, R. and Harding, K. G., Bacteria and wound healing, Curr. Opin. Infect. Dis., 2004, 17, pp. 91-96.

Eldridge, G. et al., High-throughput method for the production and analysis of large natural product libraries for drug discovery, Anal. Chem., 2002, 74(16), pp. 3963-3971.

Elsinghorst, Eric A., Measurement of Invasion by Gentamicin Resistance, Methods in Enzymology, 1994, 236, pp. 405-420.

Elvers, K. and Lappin-Scott, H., Biofilms and Biofouling Encyclopedia of Microbiology, vol. 1, 2d ed., Academic Press, San Diego, CA, pp. 478-485.

Ettmayer, Peter, Medicinal Chemistry, Lessons Learned from Marketed and Investigational Prodrugs, 2004, 47 (10), pp. 2394-2404.

Farina, C. et al., Synthesis and Anti-Ulcer Activity of New Derivatives of Glycyrrhetic, Oleanolic and Ursolic Acids, Il Farmaco, 1998, 53, pp. 22-32.

Finlay, B. B. and Cossart, P., Exploitation of Mammalian Host Cell Functions by Bacterial Pathogens, Science, May 2, 1997, 276, pp. 718-725.

Frimodt-Moller, Niels, Correlation Between Pharmacokinetic/Pharmacodynamic Parameters and Efficacy for Antibiotics in the Treatment of Urinary Tract Infection, International Journal of Antimicrobial Agents, 2002, 19, pp. 546-553.

Gallardo-Madlieno, R., et al., in Vivo Transcription of nrdAB Operon and of grxA and fpg Genes I Triggered in Escherichia coli Lacking both Thioredoxin and Glutaredoxin 1 or Thioredoxin and Glutathione, Respectively, Journal of Biological Chemistry, The American Society for Biochemistry and Molecular Biology, Inc., USA, Jul. 17, 1998, vol. 273, No. 29 pp. 18382-18388.

Gao, Ze-Li et al., Effect of Sea buckthorn on liver fibrosis: A clinical study, World J. Gastroenterol., 2003, 9(7), pp. 1615-1617.

Morissette, Sherry L. et al. , High-throughput crystallization: polymorphs, salts, co-crystals and solvates of pharmaceutical solids, Advanced Drug Delivery Reviews, 2004, 56, pp. 275-300.

Mulvey, M. A. et al., Induction and Evasion of Host Defenses by Type 1-Piliated Uropathogenic Escherichia coli, Science, Nov. 20, 1998, 282, pp. 1494-1497.

Murakami, S. et al., Ursolic acid, an antagonist for transforming growth factor (TGF) beta 1, FEBS Lett., May 21, 2004, 566, pp. 55-59.

Murphy, K. and Campellone, K. G., Lambda Red-mediated recon-nbinogenic engineering of enterohemorrhagic and enteropathogenic E. coli, BMC Molecular Biology, 2003, 4, pp. 1-12.

Nishimura, K. et al., Activity-Guided Isolation of Triterpenoid Acyl CoA Cholesteryl Acyl Transferase (ACAT) Inhibitors from Ilex kudincha, J. Nat. Prod., 1999, 62, pp. 1061-1064.

Nociari, M. M. et al., A novel one-step, highly sensitive fluorometric assay to evaluate cell-mediated cytotoxicity, J. Immunol. Met., 1998, 213, pp. 157-167.

Olofsson, A-C. et al., N-Acetyl-LCysteine Affects Growth, Extracellular Polysaccharide Production, and Bacterial biofilm Formation on Solid Surfaces, Applied and Environmental Microbiology, American Society for Microbiology, Aug. 2003, vol. 69, No. 8, pp. 4814-4822.

Parry, J. and Clark, D., Identification of a CysB-regulated gene involved in glutathione transport in Escherichia coli, FEMS Microbiology Letters, 2002, 209, pp. 81-85.

Pendland, S. L. et al., in vitro synergy testing of levofloxacin, ofloxacin, and ciprofloxacin in combination with aztreonam, ceftazidime, or piperacillin against Pseudomonas aeruginosa, Diag. Micro. Inf. Dis., 2002, 42, pp. 75-78.

Perez-Giraldo, C. et al., Influence of N-acetylcysteine on the formation of biofilm by Staphylococcus epidermidis, Journal of Antimicrobial Chemotherapy, The British Society for Antimicrobial Chemotherapy, 1997, vol. 39, pp. 643-646.

Pirzada, O. M. et al., Improved lung function and body mass index associated with long-term use of Macrolide antibiotics, J. Cystic Fibrosis, 2003, 2, pp. 69-71.

Pratt, L. and Kolter, R., Genetic analysis of Escherichia coli biofilm formation: roles of flagelia, motility, chemotaxis and type I pili, Molecular Microbiology, Oct. 1998, 30(2), pp. 285-298.

Price L. B. et al., In vitro selection and characterization of Bacillus anthracis mutants wit high-level resistance to ciprofloxacin, Antimicrob. Agents Chemother., 2003, 47(7), pp. 2362-2365.
Prieto-Alamo, M-J. et al., Transcriptional Regulation of Glutaredoxin and Thioredoxin Pathways and Related Enzymes in Response to Oxidative Stress, May 5, 2000, vol. 275, No. 18, The American Society for Biochemistry and Molecular Biology, Inc., USA, pp. 13398-13405.
Quan, J. et al., Regulation of carbon utilization by sulfur availability in *Escherichia coli* and *Salmonella typhimurium*, Microbiology, 2002, vol. 148, pp. 123-131.
Raad, I. et al., Central Venous Catheters Coated with Minocycline and Rifampin for the Prevention of Catheter-Related Colonization and Bloodstream Infections, Ann. Int. Med., 1997, 127(4), pp. 267-274.
Rakonjac et al., cysB and cysE mutants of *Escherichia coli* K12 show increased resistance to novobiocin, Mol. Gen. Genet., 1991, 228, pp. 307-311.
Ramage, G. et al., Formation of Propionibacterium acnes biofilms on orthopaedic biomaterials and their susceptibility to antimicrobials, Biomaterials, 2003, 24, pp. 3221-3227.
Ramsey, B. W. et al., Intermittent Administration of Inhales Tobramycin in Patients with Cystic fibrosis, New England J. Medicine, 1999, 340(1), pp. 23-30.
Rashid, M. H. et al., Polyphosphate kinase is essential for biofilm development, quorum sensing, and virulence of *Pseudomonas aeruginosa*, Proc. Natl. Acad. Sci., 10.1073/pnas.170283397, Aug. 15, 2000, vol. 97, No. 17, pp. 9636-9641.
Ren, D. et al., Stationary-Phase Quorum-Sensing Signals Affect Autoinducer-2 and Gene Expression in *Escherichia coli*, Applied and Environmental Microbiology, Apr. 2004, 70(4), pp. 2038-2043.
Russo, T. A., and Johnson, J. R., Medical and economic impact of extrainstestinal infections due to *Escherichia coli*: focus on an increasingly important endemic problem, Microbes and Infection, 2003, 5, pp. 449-456.
Saiman, L., The use of macrolide antibiotics in patients with cystic fibrosis, Curr. Opin. Pulm. Med., 2004, 10, pp. 515-523.
Sauer, K. et al., Characterization of Nutrient-Induced Dispersion in Pseudomonas aeruginosa PA01 Biofilm, Journal of Bacteriology, Nov. 2004, 186(21), pp. 7312-7326.

Sauer, K. and Camper, A. K., Characterization of Phenotypic Changes in Pseudomonas putida in Response to Surface-Associated Growth, J. Bacteriol., Nov. 2001, 183(22), pp. 6579-6589.

Sauer, K. et al., Pseudomonas aeruginosa Displays Multiple Phenotypes during Development as a Biofilnn, Journal of Bacteriology, Feb. 2002, 184(4), pp. 1140-1154.

Schembri, M. et al., An attractive surface: gram-negative bacterial biofilms, Sciences Stke, May 2002, vol. 2002, No. 132, pp. 1-8.

Schuhly et al., Planta Medica, 1999, 65, pp. 740-743.

Schwab, U. E. et al., Role of Actin Filament Network in Burkholderia multivorans Invasion in Well-Differentiated Human Airway Epithelia, Infect. And Immun., Nov. 2003, 71(11), pp. 6607-6609.

Singh, P. K et al., A component of innate immunity prevents bacterial biofilm development, Nature, May 30, 2002 vol. 417, Nature Publishing Group, pp. 552-555.

Slack, J. M., Stem Cells in Epithelial Tissues, (Review) Science, 2000, 287(25), pp. 1431-1957.

Stanley, N. et al., Identification of Catabolite Repression as a Physiological Regulator of Biofilm Formation by Bacillus subtilis by Use of DNA Microarrays, Journal of Bacteriology, Mar. 2003, 185(6), pp. 1951-1957.

Stella, Valentino J., Expert Opinion of Therapeutic Patents, Prodrugs as therapeutics, 2004, 14(3), pp. 277-280.

Sturgill, G. et al., Role of CysE in Production of an Extracellular Signaling Molecule in *Providencia struartii* and *Escherichia coli*: Loss of cysE Enhances Biofilm Formation in *Escherichia coli*, J. Bacteriol., Nov. 2004, 186(22), pp. 7610-7617.

Takai, T. et al., Effects of temperature and volatile fatty acids on nitrification-denitrification activity in small-scale anaerobic-aerobic recirculation biofilm process, Water Sci. Technol., 1997, 35(6), pp. 101-108.

Testa, Bernard, Biochemical Pharmacology, Prodrug Research: futile or fertile?, 2004, 68, pp. 2097-2106.

Tran, Q. H., et al., Role of glutathione in the formation of the active form of the oxygen sensor FNR ([4Fe-4S]-FNR) and in control of FNR function, Eur. J. Biochem., 2000, vol. 267, pp. 4817-4824.

Utaisincharoen, P. et al., *Burkhoderia pseudomallei* invasion and activation of epithelial cells requires activation of p38 mitogen-activated protein kinase, Microbial Pathgenesis, 2005, 38, pp. 107-112.

Van Der Ploeg, J. et al., Functional analysis of the Bacillus subtilis cysK and cysJI genes, FEMS Microbiology Letters, 2001, 201, pp. 29-35.

Veeh, R. H. et al., Detection of Staphylococcus aureus Biofilm on Tampons and Menses Components, JID, Aug. 15, 2003, 188, pp. 519-530.

Vergauwen, B. et al., Exogenous Glutathione Completes the Defense against Oxidative Stress in *Haemophilus influenzae*, Journal of Bacteriology, American Society for Microbiology, Mar. 2003, vol. 185, No. 5, pp. 1572-1581.

Verschueren, K. et al., Crystallization of full-length CysB of Klebsiella aerogenes, A LysR-type transcriptional regulator Acta Cryst., 2001, D57, pp. 260-262.

Vippagunta, Sudha R., Crystalline Solids, Advanced Drug Delivery Reviews, 2001, 48, pp. 3-26.

Wei, Y. et al., High-Density Microarray-Mediated Gene Expression Profiling of *Escherichia coli*, Journal of Bacteriology, 2001, 183(2), pp. 545-556.

Wein, L. M. et al., Emergency response to an anthrax attack, PNAS, Apr. 1, 2003, 100(7), pp. 4346-4351.

Wille, J. J. etal., Palmitoleic Acid Isomer (C16:1Δ6) in Human Skin Sebum Is Effective against Gram-Positive Bacteria, Skin Pharmacol. Appl. Skin Physiol., 2003, 16, pp. 176-187.

Wolff et al., Burger's Medicinal Chemistry, 1994, 5th Ed., vol. 1 pp. 975-977.

Xavier, K. and Bassler, B., LuxS quorum sensing: more than just a numbers game, Current Opinion in Microbiology, 2003, 6, pp. 191-197.

U.S. Appl. No. 11/479,095, filed Jun. 30, 2006, Eldridge, Gary R.

Xie, H. et al., Intergeneric Communication in Dental Plaque Biofilms (Notes), J. Bacteriol., Dec. 2000, 182(24), pp. 7067-7069.

Yang, B. et al., Effects of dietary supplementation with sea buckthorn (*Hippophae rhannnoides*) seed and pulp oils on atopic dermatitis, J. Nutr. Bichenn., 1999, 10, pp. 622-630.

Yoo, H-D. et al., Suaveolindole, a New Mass-Limited Antibacterial Indolosesquitepene from Greenwayodendron suaveolens Obtained via High-Throughput Natural Products Chemistry Methods, J. Nat. Prod., American Chemical Society and American Society of Pharmacognosy, published on web Jan. 8, 2005, 68(1), pp. 122-124.

Yoshida, M. et al. Antiproliferative Constituents from Unnbelliferae Plants VII. 1) Active Triterpenes and Rosmarinic Acid from Centella asiatica, Biol. Pharm. Bull., 2005, 28(1), pp. 173-175.

Results of search performed by NERAC for scientific articles regarding Biofilm, Jan. 28, 2005, pp. 1-40.

"Antibacterial Program" from Sequoia Sciences' website located at www.sequoiasciences.com/Antibacterials.htm, Oct. 26, 2004, pp. 1-2.

Product Brochure by Indena® at www.indena.it entitled, "Centella Asiatica Selected Triterpenes: A Highly Standardized Natural Remedy for the Maintenance of an Healthy Venous System", (Date Unknown).

International Search Report for PCT/US2005/24946 (WO 2006/010147), Jan. 26, 2006.

International Search Report for PCT/US2005/25016 (WO 2006/019926 A2), Feb. 23, 2006.

International Search Report for PCT/US2005/24945 (WO 2006/102255 Al), Sep. 28, 2006.

European Search Report for Application No. 05791709.8 dated Oct. 10, 2007, Publication No. EP1773313A2.

European Search Report for Application No. 0579135 dated Jun. 29, 2007, Publication No. EP1771558A2.

International Preliminary Report on Patentability completed on Jun. 5, 2007 for PCT/US05/32874 (WO06/031943).

International Preliminary Report on Patentability completed on Oct. 1, 2006 for PCT/US05/25016 (WO06/019926).

International Preliminary Report on Patentability completed on Oct. 18, 2006 for PCT/US05/24945 (WO06/019881).

International Preliminary Report on Patentability completed on Feb. 21, 2006 for PCT/US05/24946 (WO06/010147).

International Preliminary Report on Patentability completed on Aug. 7, 2006 for PCT/US06/10088 (WO06/102255).

Written Opinion of the International Searching Authority completed on Feb. 16, 2006 for PCT/US05/32874 (WO06/031943).

Written Opinion of the International Search Authority completed on Feb. 6, 2006 for PCT/US05/25016 (WO06/019926).

Written Opinion of the International Search Authority completed on Jan. 23, 2006 for PCT/US05/24945 (WO06/019881).

Written Opinion of the International Search Authority completed on Feb. 21, 2006 for PCT/US05/24946 (WO06/010147).

Written Opinion of the International Search Authority completed on Sep. 25, 2007 for PCT/US06/10088 (WO06/102255).

Office Action issued by the United States Patent and Trademark Office for U.S. Appl. No. 11/085,279 dated May 3, 2007.

Final Office Action issued the United States Patent and Trademark Office for U.S. Appl. No. 11/085,279 dated Apr. 3, 2008.

Office Action issued by the United States Patent and Trademark Office for U.S. Appl. No. 11/181,556 dated Oct. 6, 2008.

Ursane Scaffold

Oleanane Scaffold

COMPOUNDS, COMPOSITIONS AND METHODS FOR CONTROLLING BIOFILMS AND BACTERIAL INFECTIONS

FIELD OF THE INVENTION

The present invention generally relates to compounds useful for reducing or preventing formation of a biofilm. The present invention also relates to compounds useful for reducing or preventing the formation of a biofilm in a tissue and for controlling, preventing or treating a chronic bacterial infection.

BACKGROUND

Bacterial biofilms exist in natural, medical, and engineering environments. The biofilms offer a selective advantage to a microorganism to ensure its survival, or allow it a certain amount of time to exist in a dormant state until suitable growth conditions arise. Unfortunately, this selective advantage poses serious threats to animal health, especially human health.

Chronic infections involving biofilms are serious medical problems throughout the world. For example, biofilms are involved in 65% of human bacterial infections. Biofilms are involved in prostatitis, biliary tract infections, urinary tract infections, cystitis, lung infections, sinus infections, ear infections, acne, rosacea, dental caries, periodontitis, nosocomial infections, open wounds, and chronic wounds.

Compounds that modify biofilm formation would have a substantial medical impact by treating many chronic infections, reducing catheter- and medical device-related infections, and treating lung and ear infections. The potential market for biofilm inhibitors could be enormous given the sheer number of cases in which biofilms contribute to the medical problems. The inhibitors may be used to cure, treat, or prevent a variety of conditions, such as, but are not limited to, arterial damage, gastritis, urinary tract infections, pyelonephritis, cystitis, otitis media, otitis externa, leprosy, tuberculosis, benign prostatic hyperplasia, chronic prostatitis, chronic lung infections of humans with cystic fibrosis, osteomyelitis, bloodstream infections, skin infections, open or chronic wound infections, cirrhosis, and any other acute or chronic infection that involves or possesses a biofilm.

In the United States, the market for antibiotics is greater than $8.5 billion. After cardiovascular therapeutics, the sales of antibiotics are the second largest drug market in the United States. The antibiotic market is fueled by the continued increase in resistance to conventional antibiotics. Approximately 70% of bacteria found in hospitals resist at least one of the most commonly prescribed antibiotics. Because biofilms appear to reduce or prevent the efficacy of antibiotics, co-administration of biofilm inhibitors could significantly boost the antibiotic market.

Using the protection of biofilms, microbes can resist antibiotics at a concentration ranging from 1 to 1.5 thousand times higher than the amount used in conventional antibiotic therapy. During an infection, bacteria surrounded by biofilms are rarely resolved by the immune defense mechanisms of the host. It has been proposed that in a chronic infection, a biofilm gives bacteria a selective advantage by reducing the penetration of an antibiotic into the depths of the tissue needed to completely eradicate the bacteria's existence (Costerton J W et al., Science. 1999 May 21; 284(5418):1318-22).

Traditionally, antibiotics are discovered using the susceptibility test methods established by the National Committee for Clinical Laboratory Standards (NCCLS). The methods identify compounds that specifically affect growth or death of bacteria. These methods involve inoculation of a bacterial species into a suitable growth medium, followed by the addition of a test compound, and then plot of the bacterial growth over a time period post-incubation. Unfortunately these antibiotics derived from the NCCLS methods would not be effective therapeutics against chronic infections involving biofilms because the methods do not test compounds against bacteria in a preformed biofilm. Consistently, numerous publications have reported a difference in gene transcription in bacteria living in biofilms from bacteria in suspension, which further explains the failure of conventional antibiotics to eradicate biofilm infections (Sauer, K. et al. J. Bacteriol. 2001, 183:6579-6589).

Biofilm inhibitors can provide an alternative treatment approach for certain infections. Biofilm inhibitors, on the other hand, act on the biological mechanisms that provide bacteria protection from antibiotics and from a host's immune system. Biofilm inhibitors may be used to "clear the way" for the antibiotics to penetrate the affected cells and eradicate the infection. Traditionally, treatment of nosocomial infections requires an administration of a combination of products, such as amoxicillin/clavulanate and quinupristin/dalfopristin, or an administration of two antibiotics simultaneously. In one study of urinary catheters, rifampin was unable to eradicate methicillin-resistant *Staphylococcus aureus* in a biofilm but was effective against planktonic, or suspended cells (Jones, S. M., et. al., "Effect of vancomycin and rifampicin on methicillin-resistant *Staphylococcus aureus* biofilms", Lancet 357:40-41, 2001).

Bacteria have no known resistance to biofilm inhibitors. Biofilm inhibitors are not likely to trigger growth-resistance mechanisms or affect the growth of the normal human flora. Thus, biofilm inhibitors could potentially extend the product life of antibiotics.

Biofilm inhibitors can also be employed for the treatment of acne. Acne vulgaris is the most common cutaneous disorder. *Propionibacterium acnes*, is the predominant microorganism present in acne. The bacteria reside in biofilms. The bacteria's existence in a biofilm matrix provides them with a protective, physical barrier that limits the effectiveness of antimicrobial agents (Burkhart, C. N. et. al., "Microbiology's principle of biofilms as a major factor in the pathogenesis of acne vulgaris", International J. of Dermatology. 42:925-927, 2003). Biofilm inhibitors may be used to effectively prevent, control, reduce, or eradicate *P. acnes* biofilms in acne.

Plaque biofilms contribute to cavities and periodontitis. Plaque biofilms accumulate due to bacterial colonization of *Streptococci* spp., such as *S. mutans, S. sobrinas, S. gordonii,* and *Porphyromonas gingivalis*, and *Actinomyces* spp (Demuth, D. et al. Discrete Protein Determinant Directs the Species-Species Adherence of *Porphyromonas gingivalis* to Oral *Streptococci*, Infection and Immunity, 2001, 69(9) p 5736-5741; Xie, H., et al. Intergeneric Communication in Dental Plaque Biofilms. J. Bacteriol. 2000, 182(24), p 7067-7069). The primary colonizing bacteria of plaque accumulation are *Streptococci* spp., while *P. gingivalis* are a leading cause of periodontitis (Demuth, D. et al. Discrete Protein Determinant Directs the Species-Species Adherence of *Porphyromonas gingivalis* to Oral *Streptococci*, Infection and Immunity, 2001, 69(9) p 5736-5741). Biofilm inhibitors can be employed to prevent microorganisms from adhering to surfaces that may be porous, soft, hard, semi-soft, semi-hard, regenerating, or non-regenerating. These surfaces may be teeth, polyurethane material of central venous catheters, or metal, alloy, or polymeric surfaces of medical devices, or regenerating proteins of cellular membranes of mammals.

These inhibitors can be coated on or impregnated into these surfaces at a concentration sufficient to control, reduce, or eradicate the microorganisms adherence to these surfaces.

Chronic wound infection represents another illness that is difficult to eradicate. Examples of the most common types of chronic wounds are diabetic foot ulcers, venous leg ulcers, arterial leg ulcers, and pressure ulcers. Diabetic foot ulcers appear to be the most prevalent. These wounds are typically colonized by multiple species of bacteria including *Staphylococcus* spp., *Streptococcus* spp., *Pseudomonas* spp. and Gram-negative bacilli (Lipsky, B. Medical Treatment of Diabetic Foot Infections. Clin. Infect. Dis. 2004, 39, p.S104-14).

Based on clinical evidence, microorganisms cause or contribute to chronic wound infections. Only recently have biofilms been implicated in these infections (Harrison-Balestra, C. et al. A Wound-isolated *Pseudomonas aeruginosa* Grow a Biofilm In Vitro Within 10 Hours and Is Visualized by Light Microscopy, Dermatol Surg 2003, 29; 631-635; Edwards, R. et al. Bacteria and wound healing. Curr Opin Infect Dis, 2004, 17; 91-96). Approximately 140,000 amputations occur each year in the United States due to chronic wound infections that could not be treated with conventional antibiotics. Unfortunately, treating these infections with high doses of antibiotics over long periods of time contributes to the development of antibiotic resistance (Howell-Jones, R. S., et al. A review of the microbiology, antibiotic usage and resistance in chronic skin wounds. J. Antimicrob. Ther. Jan. 2005). Biofilm inhibitors in a combination therapy with antibiotics may provide an effective alternative to the treatment of chronic wounds.

Recent publications describe the cycles of the pathogenesis of numerous species of bacteria involving biofilms. For example, *Escherichia coli*, which causes recurrent urinary tract infections, undergo a cycle of binding to and then invading a host's bladder epithelial cells. The *E. coli* form a biofilm intracellularly, modify its morphology, and then burst out of the host cells to repeat the cycle of pathogenesis (Justice, S. et al. Differentiation and development pathways of uropathogenic *Escherichia coli* in urinary tract pathogenesis, PNAS 2004, 101(5): 1333-1338). The authors suggest that this repetitive cycle of pathogenesis of *E. coli* may explain the recurrence of the infection.

In 1997, Finlay, B. et al. reported that numerous bacteria, including *Staphylococci, Streptococci, Bordetella pertussis, Neisseria* spp., *Helicobactor pylori*, and *Yersinia* spp., adhere to mammalian cells during their pathogenesis. The authors hypothesized that the adherence would lead to an invasion of the host cell. Later publications confirm this hypothesis (Cossart, P. Science, 2004, 304; 242-248; see additional references infra). Other publications presented similar hypotheses to Mulvey, M. et al. (Mulvey, M. et al. "Induction and Evasion of Host Defenses by Type 1-Piliated Uropathogenic *E. coli*" Science 1998, 282 p. 1494-1497). In particular, Mulvey, M. et al. stated invasion of *E. coli* into epithelial cells provide protection from the host's immune response to allow a build up of a large bacterial population.

Cellular invasion and biofilm formation appear to be integral to the pathogenesis of most, if not all bacteria. *Pseudomonas aeruginosa* have been shown to invade epithelial cells during lung infections (Leroy-Dudal, J. et al. Microbes and Infection, 2004, 6, p. 875-881). *P. aeruginosa* are the principal infectious organisms found in the lungs of cystic fibrosis patients, and the bacteria exist within a biofilm. Antibiotics like tobramcyin, and other current antibacterial compounds, do not provide effective treatment against biofilms of chronic infections, perhaps because antibiotic therapy fails to eradicate the biofilm.

The pathogenesis of cellular invasion and biofilm formation gram-negative bacteria follow conserved mechanisms. For example, *Haemophilus influenzae* invade epithelial cells and form biofilms (Hardy, G. et al., Methods Mol. Med., 2003, 71; 1-18; Greiner, L. et al., Infection and Immunity, 2004, 72(7); 4249-4260). *Burkholderia* spp. invade epithelial cells and form biofilm (Utaisincharoen, P. et al., Microb Pathog. 2005, 38(2-3); 107-112; Schwab, U. et al. Infection and Immunity, 2003, 71(11); 6607-6609). *Klebsiella pneumoniae* invade epithelial cells and form biofilm (Cortes, G et al. Infection and Immunity. 2002, 70(3); 1075-1080; Lavender, H. et al., Infection and Immunity. 2004, 72(8); 4888-4890). *Salmonella* spp. invade epithelial cells and form biofilms (Cossart, P. Science, 2004, 304; 242-248; Boddicker, J. et al., Mol. Microbiol. 2002, 45(5); 1255-1265). *Yersinia pestis* invade epithelial cells and form biofilms (Cossart, P. Science, 2004, 304; 242-248; Jarrett, C. et al. J. Infect. Dis., 2004, 190; 783-792). *Neisseria gonorrhea* invade epithelial cells and form biofilms (Edwards, J. et al., Cellular Micro., 2002, 4(9); 585-598; Greiner, L. et al., Infection and Immunity. 2004, 73(4); 1964-1970). *Burkholderia* sp. are another important class of gram-negative bacterial pathogens. *Chlamydia* sp., including *Chlamydia pneumoniae* is an intracellular, Gram-negative pathogen implicated in respiratory infections and chronic diseases such as atherosclerosis and Alzheimer's disease (Little, C. S. et al., Infection and Immunity. 2005, 73(3); 1723-34).

These Gram-negative bacteria cause lung, ear, and sinus infections, gonorrhoeae, plague, diarrhea, typhoid fever, and other infectious diseases. *E. coli* and *P. aeruginosa* are two of the most widely studied Gram-negative pathogens. Researchers believe that the pathogenesis of these bacteria involves invasion of host cells and formation of biofilms. These models have enabled those skilled in the art to understand the pathogenesis of other Gram-negative bacteria.

Gram-positive bacteria also share conserved mechanisms of bacterial pathogenesis involving cellular invasion and biofilm formation. *Staphylococcus aureus* invade epithelial cells and form biofilms (Menzies, B. et al., Curr Opin Infect Dis, 2003, 16; 225-229; Ando, E. et al., Acta Med Okayama, 2004, 58(4); 207-14). *Streptococcus pyogenes* invade epithelial cells and form biofilms (Cywes, C. et al., Nature, 2001, 414; 648-652; Conley, J. et al., J. Clin. Micro., 2003, 41(9); 4043-4048).

U.S. Pat. No. 4,606,911 (referred to as the '911 patent hereafter) describes compounds that selectively inhibit the growth and anti-adherence activities of Gram-positive mouth bacteria *Streptococcus mutans* but do not effect other bacteria. This patent discloses the use of oleanolic and ursolic acid as inhibiting the growth of *S. mutans* and promoting anti-adherence activities. The patent also lists compositions for oral care products in the claims. However, the patent clearly states the benefit of ursolic acid and related compounds is that they do not affect oral microorganisms other than *S. mutans*. Growth inhibition data presented in this patent indicated that ursolic acid completely inhibited *S. mutans* and *S. salivaris* (both gram-positive Streptococcal bacteria) yet failed to inhibit the gram-positive bacterium *S. aureus* (gram-positive) or the gram negative bacteria *E. coli* and *P. aeruginosa*. Oleanolic acid displayed incomplete inhibition of *S. mutans* and *S. salivaris* (both gram-positive bacteria) yet failed to inhibit the gram-positive bacterium *S. aureus* or the gram negative bacteria *E. coli* and *P. aeruginosa*. The '911 patent thus teaches that these compounds are useful for treating tooth decay by specifically inhibiting *S. mutans* growth and adherence. Consequently, the '911 patent neither demonstrates nor suggests that ursolic acid and oleanolic acid or the derivatives described herein prevent, inhibit, or reduce the in vitro or in vivo formation of biofilms. Furthermore, the '911 patent neither demonstrates nor suggests that ursolic acid and oleanolic acid can prevent or treat bacterial infections caused by microorganisms other than *S. mutans*. Moreover, the '911 patent does not teach or suggest use of ursolic acid and oleanolic acid in oral care products in combination with an antimicrobial agent or antibiotic. Finally, the '911 patent only teaches the use of pentacyclic acid triterpene compounds with hydrogen at position C-2 and hydroxyl at C-3 for inhibition of *S. mutans* and *S. salivaris*. As demonstrated in the examples, the compounds of this instant invention may be used in combination with antibiotics to treat chronic infections like plaque.

Honda, T.; et al., in "Design and synthesis of 2-Cyano-3, 12-Dioxoolean-1,9-dien-28-oic acid, a novel and highly active inhibitor of nitric oxide production in mouse macrophages." *Bioorg. Medic. Chem. Lett.*, 1998, 8, 2711-2714, describe various oleanolic and ursolic acid derivatives including 3-hydroxy, 3-chloro-, and 2-chloro. However, this disclosure of oleanolic and ursolic acid derivatives was primarily concerned with discovery of compounds capable of inhibiting Interferon-γ induced nitric oxide production in mouse macrophages. Furthermore, the bulk of this disclosure focused on various enone-derivatives of the C-3 position of the ursane or oleanane scaffold. Finally, Honda et al neither demonstrates nor suggests that ursolic acid and oleanolic acid derivatives can prevent, inhibit, or reduce biofilm formation or bacterial infections caused by microorganisms.

Accordingly, for the reasons discussed above and others, there exists an unmet need for compounds that serve as biofilm inhibitors and/or that would be useful for preventing, reducing, or inhibiting bacterial infections.

SUMMARY OF INVENTION

The present invention provides novel pentacyclic acid triterpene compounds of the following chemical Structure I wherein $R^1$ is selected from the group consisting of hydrogen, hydroxyl, halide, methoxy, acetoxy, —$CH_2$ OH, —$CH_2$ $CH_2OH$, —CN, —$C_{1-2}$(halo)alkyl, —$CH_2$ Cl, —C(O)H, —C(O)$NH_2$, —SH, $CF_3$, $CCl_3$, and —NAA, wherein each A is independently selected from the group consisting of H and $C_1$-$C_2$ alkyl; $R^2$ is selected from the group consisting of hydroxyl, halide, —CN, —C(O)$NH_2$, —SH, —S(O)$NH_2$, $CF_3$, $CCl_3$, —NYY, wherein each Y is independently selected from H or $C_1$-$C_5$ alkyl, $C_{1-5}$ acyl halides, —$C_{1-5}$(halo)alkyl, $C_{1-5}$ acyl residues, $C_{2-5}$ secondary amides, ($C_{1-5}$)($C_{1-5}$)tertiary amides, $C_{1-5}$ alcohols, $C_{1-5}$ substituted alkyls, $C_{2-5}$ alkenyls, and $C_{2-5}$ substituted alkenyls, —OC(O)—OC($CH_3$)$_3$, —OC(O)—CH=CH-phenyl, —OC(O)—R, wherein R is an unbranched or branched $C_1$-$C_5$ alkyl, and —OC(O) $C_{1-5}R^5R^6$ wherein $R^1$ is an alkylene or alkenylene of up to 5 carbons and $R^6$ is selected from the group consisting of substituted and unsubstituted $C_{5-7}$ aromatics, substituted and unsubstituted $C_{5-7}$ cycloalkyls, and substituted and unsubstituted $C_{5-7}$ heterocycloalkyls, provided that: i) $R^2$ is not hydroxyl when $R^1$ is hydrogen, hydroxyl, methoxy, chloride or —CN; ii) $R^2$ is not chloride or —OC(O)$CH_3$ when $R^1$ is hydrogen; iii) $R^2$ is not —OC(O)—CH=CH-(m-hydroxy, p-methoxy-phenyl) or —OC(O)—CH=CH-(p-hydroxy-phenyl) when $R^1$ is hydroxyl; and iv) $R^2$ is not $C_{1-5}$ substituted alkyl, —$C_{1-5}$ (halo)alkyl, or $C_{1-5}$ alcohol when $R^1$ is hydrogen, halide, hydroxyl, methoxy, acetoxy or —SH; and wherein one of $R^3$ and $R^4$ is hydrogen and the other is methyl. Salts, hydrates, solvates, prodrugs and N-oxides of the novel pentacyclic acid triterpene compounds are also contemplated by the present invention. As demonstrated herein, such compounds are useful in controlling bacterial infections and/or biofilm formation in a variety of subjects including animals such as mammals and human patients as well as plants.

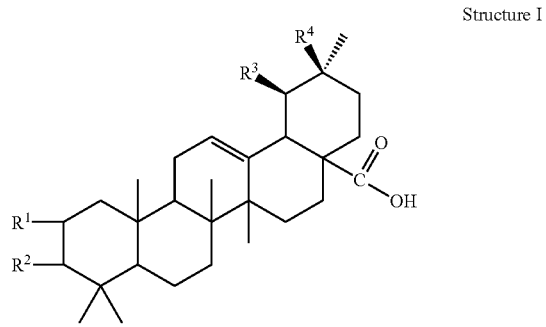

Structure I

Compositions containing the novel pentacyclic acid triterpene compounds described in the preceding paragraph and a pharmaceutically acceptable carrier above are also contemplated by this invention. Such compositions containing the novel pentacyclic acid triterpene compound optionally include an antimicrobial agent. Still other compositions comprising other pentacyclic acid triterpene compounds, a pharmaceutically acceptable carrier and an antimicrobial agent are also contemplated. The other pentacyclic acid triterpenes used in the compositions containing antimicrobial agents are of the preceeding chemical Structure I wherein $R^1$ is selected from the group consisting of hydrogen, hydroxyl, halide, methoxy, acetoxy, —$CH_2$ OH, —$CH_2$ $CH_2OH$, —CN, —$C_{1-2}$(halo)alkyl, —$CH_2$ Cl, —C(O)H, —C(O)$NH_2$, —SH, $CF_3$, $CCl_3$, and —NAA, wherein each A is independently selected from the group consisting of H and $C_1$-$C_2$ alkyl; $R^2$ is selected from the group consisting of hydroxyl, halide, —CN, —C(O)$NH_2$, —SH, —S(O)$NH_2$, $CF_3$, $CCl_3$, —NYY, wherein each Y is independently selected from H or $C_1$-$C_5$ alkyl, $C_{1-5}$ acyl halides, —$C_{1-5}$(halo)alkyl, $C_{1-5}$ acyl residues, $C_{2-5}$ secondary amides, ($C_{1-5}$)($C_{1-5}$)tertiary amides, $C_{1-5}$ alcohols, $C_{1-5}$ substituted alkyls, $C_{2-5}$ alkenyls, and $C_{2-5}$ substituted alkenyls, —OC(O)—OC($CH_3$)$_3$, —OC(O)—CH=CH-phenyl, —OC(O)—R, wherein R is an unbranched or branched $C_1$-$C_5$ alkyl, and —OC(O) $C_{1-5}R^5R^6$ wherein $R^5$ is an alkylene or alkenylene of up to 5 carbons and $R^6$ is selected from the group consisting of substituted and unsubstituted $C_{5-7}$ aromatics, substituted and unsubstituted $C_{5-7}$ cycloalkyls, and substituted and unsubstituted $C_{5-7}$ heterocloalkyls; provided that: i) $R^2$ is not hydroxyl when $R^1$ is hydrogen or hydroxyl; ii) $R^2$ is not —OC(O)$CH_3$ when $R^1$ is hydrogen; and iii) $R^2$ is not —OC(O)—CH=CH-(m-hydroxy, p-methoxy-phenyl) or —OC(O)—CH=CH-(p-hydroxy-phenyl) when $R^1$ is hydroxyl; one of $R^3$ and $R^4$ is hydrogen and the other is methyl. Salts, hydrates, solvates, prodrugs and N-oxides of the pentacyclic acid triterpene compounds are also contemplated by the present invention. As demonstrated herein, such compositions are useful in controlling bacterial infections and/or biofilm formation in a variety of subjects including animals such as mammals and human patients as well as plants.

This invention also provides methods for preventing, inhibiting or reducing a biofilm comprising contacting the biofilm or a cell capable of biofilm formation with an effective amount of a composition or a compound comprising a pentacyclic acid triterpene compound of the preceeding chemical Structure I wherein $R^1$ is selected from the group consisting of hydrogen, hydroxyl, halide, methoxy, acetoxy, —$CH_2$ OH, —$CH_2$ $CH_2OH$, —CN, —$C_{1-2}$(halo)alkyl, —$CH_2$ Cl, —C(O)H, —C(O)$NH_2$, —SH, $CF_3$, $CCl_3$, and —NAA, wherein each A is independently selected from the group consisting of H and $C_1$-$C_2$ alkyl; $R^2$ is selected from the group consisting of hydroxyl, halide, —CN, —C(O)$NH_2$, —SH, —S(O)$NH_2$, $CF_3$, $CCl_3$, —NYY, wherein each Y is independently selected from H or $C_1$-$C_5$ alkyl, $C_{1-5}$ acyl halides, —$C_{1-5}$(halo)alkyl, $C_{1-5}$ acyl residues, $C_{2-5}$ secondary amides, ($C_{1-5}$)($C_{1-5}$)tertiary amides, $C_{1-5}$ alcohols, $C_{1-5}$ substituted alkyls, $C_{2-5}$ alkenyls, and $C_{2-5}$ substituted alkenyls, —OC(O)—OC($CH_3$)$_3$, —OC(O)—CH=CH-phenyl, —OC(O)—R, wherein R is an unbranched or branched $C_1$-$C_5$ alkyl, and —OC(O)$C_{1-5}R^5R^6$ wherein $R^5$ is an alkylene or alkenylene of up to 5 carbons and $R^6$ is selected from the group consisting of substituted and unsubstituted $C_{5-7}$ aromatics, substituted and unsubstituted $C_{5-7}$ cycloalkyls, and substituted and unsubstituted $C_{5-7}$ heterocycloalkyls; provided that: i) $R^2$ is not hydroxyl when $R^1$ is hydrogen or hydroxyl; ii) $R^2$ is not —OC(O)$CH_3$ when $R^1$ is hydrogen; and iii) $R^2$ is not —OC(O)—CH=CH-(m-hydroxy, p-methoxy-phenyl) or —OC(O)—CH=CH-(p-hydroxy-phenyl) when $R^1$ is hydroxyl; one of $R^3$ and $R^4$ is hydrogen and the other is methyl. Salts, hydrates, solvates, prodrugs and N-oxides of the pentacyclic acid triterpene compounds are also contemplated by the present invention. Compositions use the pentacyclic acid triterpene compound contain an acceptable carrier. When the composition is used in animals or humans to prevent biofilms, the acceptable carrier is a pharmaceutically acceptable carrier. When the composition is used in plants to prevent biofilms, the acceptable carrier is a agriculturally acceptable carrier.

Inhibition or reduction of biofilm formation may be effected either in vivo or in vitro. Compositions used to inhibit, reduce or prevent biofilm formation may further include either an antimicrobial agent, antibiotic or a biocide. The methods also provide for preventing, inhibiting or reducing biofilm formation on a variety of substrates.

This invention further provides for methods of inhibiting or preventing a bacterial infection in a subject by administering an effective amount of a composition comprising a pentacyclic acid triterpene compound corresponding to the preceeding chemical Structure I wherein $R^1$ is selected from the group consisting of hydrogen, hydroxyl, halide, methoxy, acetoxy, —$CH_2$ OH, —$CH_2$ $CH_2OH$, —CN, —$C_{1-2}$(halo)alkyl, —$CH_2$ Cl, —C(O)H, —C(O)$NH_2$, —SH, $CF_3$, $CCl_3$, and —NAA, wherein each A is independently selected from the group consisting of H and $C_1$-$C_2$ alkyl; $R^2$ is selected from the group consisting of hydroxyl, halide, —CN, —C(O)$NH_2$, —SH, —S(O)$NH_2$, $CF_3$, $CCl_3$, —NYY, wherein each Y is independently selected from H or $C_1$-$C_5$ alkyl, $C_{1-5}$ acyl halides, —$C_{1-5}$(halo)alkyl, $C_{1-5}$ acyl residues, $C_{2-5}$ secondary amides, ($C_{1-5}$)($C_{1-5}$)tertiary amides, $C_{1-5}$ alcohols, $C_{1-5}$ substituted alkyls, $C_{2-5}$ alkenyls, and $C_{2-5}$ substituted alkenyls, —OC(O)—OC($CH_3$)$_3$, —OC(O)—CH=CH-phenyl, —OC(O)—R, wherein R is an unbranched or branched $C_1$-$C_5$ alkyl, and —OC(O) $C_{1-5}R^5R^6$ wherein $R^5$ is an alkylene or alkenylene of up to 5 carbons and $R^6$ is selected from the group consisting of substituted and unsubstituted $C_{5-7}$ aromatics, substituted and unsubstituted $C_{5-7}$ cycloalkyls, and substituted and unsubstituted $C_{5-7}$ heterocycloalkyls; provided that: i) $R^2$ is not hydroxyl when $R^1$ is hydrogen or hydroxyl; ii) $R^2$ is not —OC(O)$CH_3$ when $R^1$ is hydrogen; and iii) $R^2$ is not —OC(O)—CH=CH-(m-hydroxy, p-methoxy-phenyl) or —OC(O)—CH=CH-p-hydroxy-phenyl) when $R^1$ is hydroxyl; one of $R^3$ and $R^4$ is hydrogen and the other is methyl. Salts, hydrates, solvates, prodrugs and N-oxides of the pentacyclic acid triterpene compounds are also contemplated by the present invention.

The subject may be a human, an animal or a plant. When the subject is a mammal or a human, the carrier is a pharmaceutically acceptable carrier. When the subject is a plant, the carrier is an agriculturally acceptable carrier. Compositions used to inhibit, reduce or prevent bacterial infection may further include either an antimicrobial agent or antibiotic.

The invention also provides for processes of making the both the novel pentacyclic acid triterpene compounds described herein as well as other previously disclosed pentacyclic acid triterpene compounds.

The novel or known pentacyclic acid triterpene compound can be obtained by either modifying a known precursor from a commercial source or a natural source. Alternatively, the novel or known pentacyclic acid triterpene compound can be obtained by direct synthesis. Such compounds may be used in either pharmaceutical compositions, in which case a pharmaceutically acceptable carrier is used, or agricultural compositions, in which case an agriculturally acceptable carrier is used.

Finally, the present invention further provides for other novel pentacyclic acid triterpene compounds corresponding to the following chemical Structure II wherein $R^1$ is selected from the group consisting of hydrogen, hydroxyl, halide, methoxy, acetoxy, —$CH_2$ OH, —$CH_2$ $CH_2OH$, —CN, —$C_{1-2}$(halo)alkyl, —$CH_2$ Cl, —C(O)H, —C(O)$NH_2$, —SH, $CF_3$, $CCl_3$, and —NAA, wherein each A is independently selected from the group consisting of H and $C_1$-$C_2$ alkyl; $R^2$ is selected from the group consisting of hydroxyl, halide, —CN, —C(O)$NH_2$, —SH, —S(O)$NH_2$, $CF_3$, $CCl_3$, —NYY, wherein each Y is independently selected from H or $C_1$-$C_5$ alkyl, $C_{1-5}$ acyl halides, —$C_{1-5}$(halo)alkyl, $C_{1-5}$ acyl residues, $C_{2-5}$ secondary amides, ($C_{1-5}$)($C_{1-5}$)tertiary amides, $C_{1-5}$ alcohols, $C_{1-5}$ substituted alkyls, $C_{2-5}$ alkenyls, and $C_{2-5}$ substituted alkenyls, substituted or unsubstituted $C_{5-7}$ aromatics, —OC(O)—OC($CH_3$)$_3$, —OC(O)—CH=CH-phenyl, —OC(O)—R, wherein R is an unbranched or branched $C_1$-$C_5$ alkyl, and —OC(O) $C_{1-5}R^{13}R^{14}$ wherein $R^{13}$ is an alkylene or alkenylene of up to 5 carbons and $R^{14}$ is selected from the group consisting of substituted and unsubstituted $C_{5-7}$ aromatics, substituted and unsubstituted $C_{5-7}$ cycloalkyls, and substituted and unsubstituted $C_{5-7}$ heterocycloalkyls; provided that: i) $R^2$ is not hydroxyl when $R^1$ is hydrogen, hydroxyl, methoxy, chloride or —CN; ii) $R^2$ is not chloride or —OC(O)$CH_3$ when $R^1$ is hydrogen; iii) $R^2$ is not —OC(O)—CH=CH-(m-hydroxy, p-methoxy-phenyl) or —OC(O)—CH=CH-(p-hydroxy-phenyl) when $R^1$ is hydroxyl; and iv) $R^2$ is not $C_{1-5}$ substituted alkyl, —$C_{1-5}$(halo)alkyl, or $C_{1-5}$ alcohol when $R^1$ is hydrogen, halide, hydroxyl, methoxy, acetoxy or —SH; $R^3$ is selected from the group consisting of hydrogen, methyl, halide, and —$NH_2$; $R^4$ is selected from the group consisting of hydrogen, methyl, hydroxyl, halide, $C_{1-3}$ alkoxy, —CN, —$NH_2$, —C(O)H, —C(O)$NH_2$, —SH, —S(O)$NH_2$, carboxylic acid groups, $C_{1-3}$ acyl halides, $C_{1-3}$ acyl residues, $C_{2-3}$ secondary amides, $C_{1-3}$ alcohols, ($C_{1-2}$)($C_{1-2}$) ethers, $C_{2-3}$ alkyls, $C_{1-3}$ substituted alkyls, $C_{2-3}$ alkenyls, and $C_{2-3}$ substituted alkenyls; $R^5$, and $R^{12}$ are independently selected from the group consisting of hydrogen, hydroxyl, halide, $C_{1-3}$ alkoxy, —CN, —$NH_2$, —C(O)$NH_2$, —OC(O)$C_{1-3}$, —SH, —S(O)$NH_2$, and —$C_{1-3}$(halo)alkyl; $R^6$ and $R^7$ are independently selected from the group consisting of hydrogen, hydroxyl, halide, and —$NH_2$; one of $R^8$ and $R^{10}$ is hydrogen and the other is methyl; and $R^9$ and $R^{11}$ are independently selected from the group consisting of hydrogen, methyl, hydroxyl, halide, $C_{1-3}$ alkoxy, —$NH_2$, and —CN. Salts, hydrates, solvates, prodrugs and N-oxides of the novel pentacyclic acid triterpene compounds of Structure II are also contemplated by the present invention.

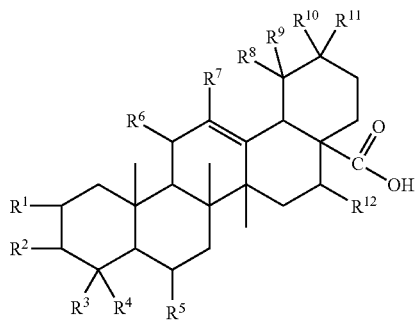

Structure II

DESCRIPTION OF THE INVENTION

Definitions

Figure 1:
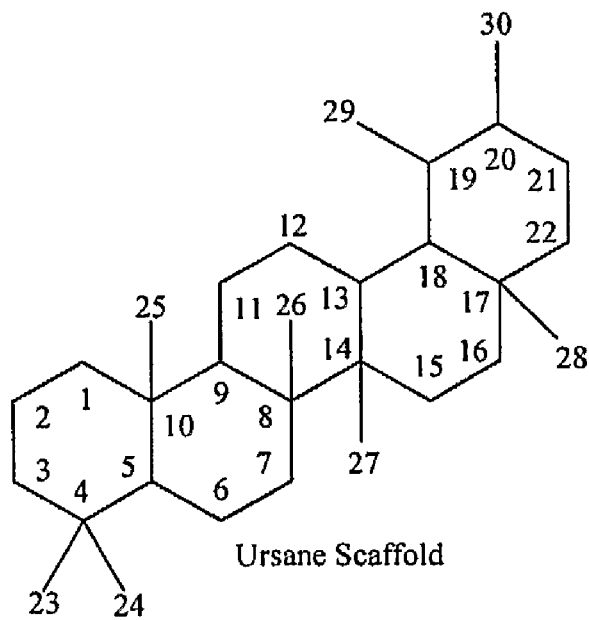
FIG. 1 shows the Ursane and Oleanane scaffold structures with Carbon number designations.
Figure 1:
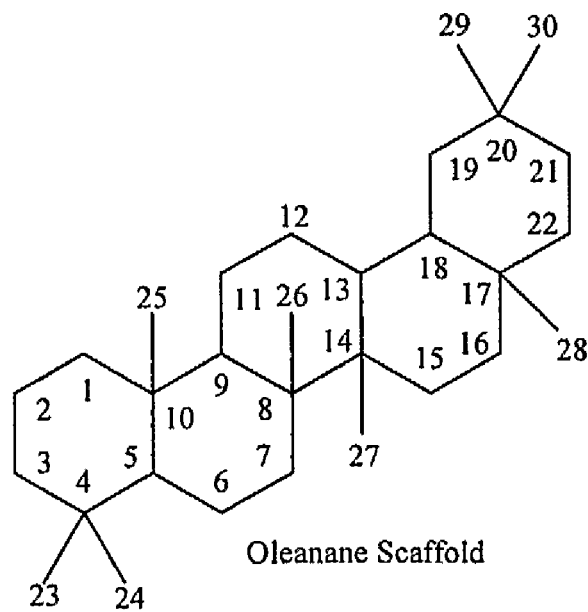

"Acceptable carrier" refers to a carrier that is not deleterious to the other ingredients of the composition and is not deleterious to material to which it is to be applied. "Pharmaceutically acceptable carrier" refers to a carrier that is not deleterious to the other ingredients of the composition and is not deleterious to the human or other animal recipient thereof. "Agriculturally acceptable carrier" refers to a carrier that is not deleterious to the other ingredients of the composition and is not deleterious to the plant recipient thereof. In the context of the other ingredients of the composition, "not deleterious" means that the carrier will not react with or degrade the other ingredients or otherwise interfere with their efficacy. Interference with the efficacy of an ingredient does not encompass mere dilution of the ingredient. In the context of the animal or plant host, "not deleterious" means that the carrier is not injurious or lethal to the plant or animal.

"Administration" refers to any means of providing a compound or composition to a subject. Non-limiting examples of administration means include oral, topical, rectal, percutaneous, parenteral injection, intranasal and inhalation delivery.

"Biofilm" refers to an extracellular matrix in which microorganisms are dispersed and/or form colonies. The biofilm typically is made of polysaccharides and other macromolecules.

"Commercial source" refers to a vendor that provides the desired compound.

"Direct synthesis" refers to production of the desired compound by reacting appropriate compound precursors under appropriate conditions to obtain the desired compound.

"Effective amount" refers to the amount of compound or composition that, in the case of biofilm formation, will reduce the size or volume of existing biofilms; reduce the rate at which bacteria are capable of producing biofilm; or will inhibit or prevent the formation of biofilm by one or more microorganisms. In the context of treating a bacterial infection, an "effective amount" refers the amount of a compound or composition that will reduce the degree of an existing infection or will inhibit or prevent an infection from occurring.

"Essentially pure preparation" refers to a preparation in which the concentration of the desired ingredient is at least 95% or more of the preparation by weight. In the context of this processes used in this invention, the antimicrobial agents and pentacyclic acid triterpene compounds typically and preferably make up 99% or more by weight of the preparation and are referred to herein as "highly pure" preparations.

"In vivo", in the context of biofilm formation, refers to effects mediated in or upon living organisms or subjects. Effects mediated on biofilms associated with medical devices such as central venous catheters, urinary catheters, endotracheal tubes, mechanical heart valves, pacemakers, vascular grafts, stents, and prosthetic joints located within a living organism or subject are considered as "in vivo" uses of the compounds and compositions described herein.

"In vitro", in the context of biofilm formation, refers to effects mediated on substrates located outside of an organism that are potential sites of biofilm formation. Non-limiting examples of substrates include vessel hulls, cars, airplanes, industrial equipment, devices, membranes, filters, microtiter plates, continuous flow chambers, bioreactors, fermentors, chemostats and machinery.

"Is one that permits" as it relates to a pharmaceutically acceptable carrier that has characteristics that enable the preparation to be used for a given mode of administration of the composition. For example, pharmaceutically acceptable carriers that permit parenteral administration to an animal are liquids that are not injurious or lethal to the animals when so injected. Such carriers often comprise sterile water, which may be supplemented with various solutes to increase solubility. Sterile water or sterile water supplemented with solutes is thus a pharmaceutically acceptable carrier that permits parental administration.

"Natural source" is defined as any living organism or material derived therefrom. Note that in the context of this application, the natural source may be a novel living organism or material derived therefrom.

"Reducing or inhibiting" in reference to a biofilm refers to the prevention of biofilm formation or growth, a reduction in the rate of biofilm formation or growth, reduction or removal of preformed or existing biofilm, as well as the partial or complete inhibition of biofilm formation or growth.

"Subject in need thereof" refers to living organism that would benefit from either prevention or reductions in the degree of a bacterial infection. Subjects may include animals or more specifically, mammals or humans. Subjects may also include plants.

"Substrate" refers to any material to which the compound or a composition containing the compound may be applied.

The phrases "C(1-12)alkyl" and "C(1-12)alkyls," as used herein, mean saturated or unsaturated, straight- or branched-chain hydrocarbon radicals containing between one and twelve carbon atoms. Examples of C(1-12)alkyl radicals include, but are not limited to, ethyl, propyl, isopropyl, n-hexyl, octyl, decyl, dodecyl radicals.

The phrases "C(1-12) substituted alkyl" and "C(1-12) substituted alkyls," as used herein, mean a "C(1-12)alkyl" group, as previously defined, substituted by independent replacement of one, two, or three of the hydrogen atoms thereon with substituents including, but not limited to, —F, —Cl, —Br, —I, —OH, protected hydroxy, —NO$_2$, —CN, —C(1-12)alkyl optionally substituted with halogen, —C(2-12)alkenyl optionally substituted with halogen, —C(2-12)alkynyl optionally substituted with halogen, —NH2, protected amino, —NH—C(1-12)alkyl, —NH—C(2-12)alkenyl, —NH—C(2-12)alkenyl, —NH—C(3-12)cycloalkyl, —NH-aryl, —NH-heteroaryl, —NH-heterocycloalkyl, -dialkylamino, -diarylamino, -diheteroarylamino, —O—C(1-12)alkyl, —O—C(2-12)alkenyl, —O—C(3-12)cycloalkyl, —O-aryl, —O$_2$9heteroaryl, —O-heterocycloalkyl, —C(O)—C(1-12)alkyl, —C(O)—C(2-12)alkenyl, —C(O)—C(3-12)cycloalkyl, —C(O)-aryl, —C(O)-heteroaryl, —C(O)-heterocycloalkyl, —CONH2, —CONH—C(1-12)alkyl, —CONH—C(2-12)alkenyl, —CONHC(3-12)-cycloalkyl, —CONH-aryl, —CONH-heteroaryl, —CONH-heterocycloalkyl, —OCO$_2$—C(1-12)alkyl, —OCO$_2$—C(2-12)alkenyl, —OCO$_2$—C(3-12)cycloalkyl, —OCO$_2$-aryl, —OCO$_2$-heteroaryl, —OCO$_2$-heterocycloalkyl, —OCONH2, —OCONHC(1-12)alkyl, —OCONH—C(2-12)alkenyl, —OCONH—C(3-12)cycloalkyl, —OCONH-aryl, —OCONH-heteroaryl, —OCONH-heterocycloalkyl, —NHC(O)—C(1-12)alkyl, —NHC(O)—C(2-12)alkenyl, —NHC(O)—C(3-12)cycloalkyl, —NHC(O)-aryl, —NHC(O)-heteroaryl, —NHC(O)-heterocycloalkyl, —NHCO$_2$—C(1-12)alkyl, —NHCO$_2$—C(2-12)alkenyl, —NHCO$_2$—C(3-12)cycloalkyl, —NHCO$_2$-aryl, —NHCO$_2$-heteroaryl, —NHCO$_2$-heterocycloalkyl, —NHC(O)NH2, NHC(O)NHC(1-12)alkyl, —NHC(O)NH—C(2-12)alkenyl, —NHC(O)NH—C(3-12)cycloalkyl, —NHC(O)NH-aryl, —NHC(O)NH-heteroaryl, —NHC(O)NH-heterocycloalkyl, NHC(S)NH2, NHC(S)NH—C(1-12)alkyl, —NHC(S)NH—C(2-12)alkenyl, —NHC(S)NH—C(3-12)cycloalkyl, —NHC(S)NH-aryl, —NHC(S)NH-heteroaryl, —NHC(S)NH-heterocycloalkyl, —NHC(NH)NH2, NHC(NH)NH—C(1-12)alkyl, —NHC(NH)NH—C(2-12)alkenyl, —NHC(NH)NH—C(3-12)cycloalkyl, —NHC(NH)NH-aryl, —NHC(NH)NH-heteroaryl, —NHC(NH)NH-heterocycloalkyl, NHC(NH)—C(1-12)alkyl, —NHC(NH)—C(2-12)alkenyl, —NHC(NH)—C(3-12)cycloalkyl, —NHC(NH)-aryl, —NHC(NH)-heteroaryl, —NHC(NH)-heterocycloalkyl, —C(NH)NH—C(1-12)alkyl, —C(NH)NH—C(2-12)alkenyl, —C(NH)NH—C(3-12)cycloalkyl, —C(NH)NH-aryl, —C(NH)NH-heteroaryl, —C(NH)NH heterocycloalkyl, —S(O)—C(1-12)alkyl, —S(O)—C(2-12)alkenyl, —S(O)—C(3-12)cycloalkyl, —S(O)-aryl, —S(O)-heteroaryl, —S(O)-heterocycloalkyl —SO$_2$NH2, —SO$_2$NH—C(1-12)alkyl, —SO$_2$NHC(2-12)alkenyl, —SO$_2$NH—C(3-12)cycloalkyl, —SO$_2$NH-aryl, —SO$_2$NH-heteroaryl, —SO$_2$NHheterocycloalkyl, —NHSO$_2$—C(1-12)alkyl, —NHSO$_2$—C(2-12)alkenyl, —NHSO$_2$—C(3-12)cycloalkyl, 30-NHSO$_2$-aryl, —NHSO$_2$-heteroaryl, —NHSO$_2$-heterocycloalkyl, —CH2NH2, —CH2SO$_2$CH3, -aryl, -arylalkyl, -heteroaryl, -heteroarylalkyl, -heterocycloalkyl, —C(1-12)-cycloalkyl, -methoxymethoxy, -methoxyethoxy, —SH, —S—C(1-12)alkyl, —S—C(2-12)alkenyl, —S—C(3-12)cycloalkyl, —S-aryl, —S-heteroaryl, —S-heterocycloalkyl, or methylthiomethyl.

In the present invention, "alkoxy," by itself or as part of another substituent, means a radical of the formula —OR, where R is an alkyl or cycloalkyl group as defined herein. Representative examples alkoxy groups include, but are not limited to, methoxy, ethoxy, propoxy, isopropoxy, butoxy, tert-butoxy, cyclopropyloxy, cyclopentyloxy, cyclohexyloxy and the like.

In the present invention, "alkoxycarbonyl," by itself or as part of another substituent, refers to a radical of the formula —C(O)-alkoxy, where alkoxy is as defined herein.

"Alkylthio," by itself or as part of another substituent, means a radical of the formula —SR, where R is an alkyl or cycloalkyl group as defined herein.

Representative examples of Alkylthio groups include, but are not limited to, methylthio, ethylthio, propylthio, isopropylthio, butylthio tert-butylthio, cyclopropylthio, cyclopentylthio, cyclohexylthio, and the like.

The phrases "C(2-12)alkenyl" and "C(2-12)alkenyls," as used herein, mean a monovalent group derived from a hydrocarbon moiety containing from two to twelve carbon atoms having at least one carbon-carbon double bond by the removal of a single hydrogen atom. C(2-12)alkenyl groups include, but are not limited to, for example, ethenyl, propenyl, butenyl, 1-methyl-2-buten-1-yl, and the like.

The phrases "C(2-12) substituted alkenyl" and "C(2-12) substituted alkenyls," as used herein, mean a "C(2-12)alkenyl" as previously defined, substituted by independent replacement or one, two, or three of the hydrogen atoms thereon with substituents including, but not limited to, —F, —Cl, —Br, —I, —OH, protected hydroxy, —NO$_2$, —CN, —C(1-12)-alkyl optionally substituted with halogen, C(2-12)alkenyl optionally substituted with halogen, —C(2-12)alkynyl optionally substituted with halogen, —NH2, protected amino, —NH—C(1-12)alkyl, —NH—C(2-12)alkenyl, —NH—C(3-12)cycloalkyl, —NH-aryl, —NH-heteroaryl, —NH-heterocycloalkyl, -dialkylamino, -diarylamino, -diheteroarylamino, —O—C(1-12)alkyl, —OC(2-12)alkenyl, —O—C(1-12)cycloalkyl, —O-aryl, —O-heteroaryl, —O-heterocycloalkyl, —C(O)—C(1-12)alkyl, —C(O)—C(2-12)alkenyl, —C(O)—C(3-12)-cycloalkyl, —C(O)-aryl, —C(O)-heteroaryl, —C(O)-heterocycloalkyl, —CONH2, —CONH—C(1-12)alkyl, —CONH—C(2-12)alkenyl, —CONH—C(2-12)alkenyl, —CONH—C(3-12)cycloalkyl, —CONH-aryl, —CONH-heteroaryl, —CONHheterocycloalkyl, —OCO$_2$—C(1-12)alkyl, —OCO$_2$—C(2-12)alkenyl, —OCO$_2$—C(2-12)alkenyl, —OCO$_2$—C(3-12)cycloalkyl, —OCO$_2$-aryl, —OCO$_2$-heteroaryl, —OCO$_2$-heterocycloalkyl, —OCONH, —OCONH—C(1-12)alkyl, —OCONH—C(2-12)alkenyl, —OCONH—C(2-12)alkenyl, —OCONH—C(3-12)cycloalkyl, —OCONH-aryl, —OCONH-heteroaryl, —OCONHheterocycloalkyl, —NHC(O)—C(1-12)alkyl, —NHC(O)—C(2-12)alkenyl, —NHC(O)—C(2-12)alkenyl, —NHC(O)—C(3-12)cycloalkyl, —NHC(O)-aryl, —NHC(O)-heteroaryl, —NHC(O)-heterocycloalkyl, —NHCO$_2$—C(1-12)alkyl, —NHCO$_2$—C(2-12)alkenyl, —NHCO$_2$—C(2-12)alkenyl, —NHCO$_2$—C(3-12)cycloalkyl, —NHCO$_2$-aryl, —NHCO$_2$-heteroaryl, —NHCO$_2$-heterocycloalkyl, —NHC(O)NH2, NHC(O)NH—C(1-12)alkyl, —NHC(O)NH—C(2-12)alkenyl, —NHC(O)NH—C(2-12)alkenyl, —NHC(O)NH—C(3-12)cycloalkyl, —NHC(O)NH-aryl, —NHC(O)NH-heteroaryl, —NHC(O)NH-heterocycloalkyl, NHC(S)NH2, NHC(S)NH—C(1-12)alkyl, —NHC(S)NH—C(2-12)alkenyl, —NHC(S)NH—C(2-12)alkenyl, —NHC(S)NH—C(3-

12)cycloalkyl, —NHC(S)NH-aryl, —NHC(S)NH-heteroaryl, —NHC(S)NH-heterocycloalkyl, —NHC(NH)NH2, NHC(NH)NH—C(1-12)alkyl, —NHC(NH)NH—C(2-12)alkenyl, —NHC(NH)NH—C(2-12)alkenyl, —NHC(NH)NH—C(3-12)cycloalkyl, —NHC(NH)NH-aryl, —NHC(NH)NH-heteroaryl, —NHC(NH)NH-heterocycloalkyl, NHC(NH)—C(1-12)alkyl, —NHC(NH)—C(2-12)alkenyl, —NHC(NH)C(2-12)alkenyl, —NHC(NH)—C(3-12)cycloalkyl, —NHC(NH)-aryl, —NHC(NH)-heteroaryl, —NHC(NH)-heterocycloalkyl, —C(NH)NH—C(1-12)alkyl, —C(NH)NHC(2-12)alkenyl, —C(NH)NH—C(2-12)alkenyl, —C(NH)NH—C(3-12)cycloalkyl, —C(NH)NH-aryl, —C(NH)NH-heteroaryl, C(NH)NH-heterocycloalkyl, —S(O)—C(1-12)alkyl, —S(O)—C(2-12)alkenyl, —S(O)—C(2-12)alkenyl, —S(O)—C(3-12)cycloalkyl, —S(O)-aryl, —S(O)-heteroaryl, —S(O)-heterocycloalkyl-SO$_2$ NH2, —SO$_2$ NH—C(1-12)alkyl, —SO$_2$ NH—C(2-12)alkenyl, —SO$_2$ NH—C(2-12)alkenyl, —SO$_2$ NH—C(3-12)cycloalkyl, —SO$_2$ NH-aryl, —SO$_2$ NH heteroaryl, —SO$_2$ NH-heterocycloalkyl, —NHSO$_2$—C(1-12)alkyl, —NHSO$_2$—C(2-12)alkenyl, —NHSO$_2$—C(2-12)alkenyl, —NHSO$_2$—C(3-12)cycloalkyl, —NHSO$_2$-aryl, —NHSO$_2$-heteroaryl, —NHSO$_2$-heterocycloalkyl, —CH2 NH2, —CH2 SO$_2$ CH3, -aryl, -arylalkyl, -heteroaryl, -heteroarylalkyl, -heterocycloalkyl, —C(3-12)cycloalkyl, methoxymethoxy, -methoxyethoxy, —SH, —S—C(1-12)alkyl, —S—C(2-12)alkenyl, —S—C(2-12)alkenyl, —S—C(3-12)cycloalkyl, —S-aryl, -Sheteroaryl, —S-heterocycloalkyl, or methylthiomethyl.

The phrase "C(2-12)alkynyl" and "C(2-12)alkynyls," as used herein, mean a monovalent group derived from a hydrocarbon moiety containing from two to twelve carbon atoms having at least one carbon-carbon triple bond by the removal of a single hydrogen atom. Representative alkynyl groups include, but are not limited to, for example, ethynyl, 1-propynyl, 1-butynyl, and the like.

The phrases "substituted alkynyl" and "substituted alkynyls," as used herein, mean a "C(2-12)alkynyl" group as previously defined, substituted by independent replacement or one, two, or three of the hydrogen atoms thereon with substituents including, but not limited to, —F, —Cl, —Br, —I, —OH, protected hydroxy, —NO$_2$, —CN, —C(1-12) alkyl optionally substituted with halogen, C(2-12)alkenyl optionally substituted with halogen, —C(2-12)alkynyl optionally substituted with halogen, —NH2, protected amino, —NHC(1-12)alkyl, —NH—C(2-12)alkenyl, —NH—C(2-12)alkenyl, —NH—C(3-12)cycloalkyl, —NH-aryl, —NHheteroaryl, —NH-heterocycloalkyl, -dialkylamino, -diarylamino, -diheteroarylamino, —O—C(1-12)alkyl, —O—C(2-12)alkenyl, —O—C(2-12)alkenyl, —O—C(3-12)cycloalkyl, —O-aryl, —O-heteroaryl, —O-heterocycloalkyl, —C(O)—C(1-12)alkyl, —C(O)—C(2-12)alkenyl, —C(O)—C(2-12)alkenyl, —C(O)—C(3-12)cycloalkyl, —C(O)-aryl, —C(O)-heteroaryl, —C(O)-heterocycloalkyl, —CONH2, —CONHC(1-12)alkyl, —CONH—C(2-12)alkenyl, —CONH—C(2-12)alkenyl, —CONH—C(3-12)cycloalkyl, —CONH-aryl, —CONH-heteroaryl, —CONH-heterocycloalkyl, —OCO$_2$—C(1-12)alkyl, —OCO$_2$—C(2-12)alkenyl, —OCO$_2$—C(2-12)alkenyl, —OCO$_2$—C(3-12)cycloalkyl, —OCO$_2$-aryl, —OCO$_2$-heteroaryl, —OCO$_2$-heterocycloalkyl, —OCONH2, —OCONH—C(1-12)alkyl, —OCONH—C(2-12)alkenyl, —OCONH—C(2-12)alkenyl, —OCONH—C(3-12)cycloalkyl, —OCONH-aryl, —OCONH heteroaryl, —OCONH-heterocycloalkyl, —NHC(O)—C(1-12)alkyl, —NHC(O)—C(2-12)alkenyl, —NHC(O)—C(2-12)alkenyl, —NHC(O)—C(3-12)cycloalkyl, —NHC(O)-aryl, —NHC(O)-heteroaryl, —NHC(O)-heterocycloalkyl, —NHCO$_2$—C(1-12)alkyl, —NHCO$_2$—C(2-12)alkenyl, —NHCO$_2$—C(2-12)alkenyl, —NHCO$_2$—C(3-12)cycloalkyl, —NHCO$_2$-aryl, —NHCO$_2$-heteroaryl, —NHCO$_2$-heterocycloalkyl, —NHC(O)NH2, NHC(O)NH—C(1-12)alkyl, —NHC(O)NH—C(2-12)alkenyl, —NHC(O)NH—C(2-12)alkenyl, —NHC(O)NHC(3-12)cycloalkyl, —NHC(O)NH-aryl, —NHC(O)NH heteroaryl, —NHC(O)NH-heterocycloalkyl, NHC(S)NH2; NHC(S)NH—C(1-12)alkyl, —NHC(S)NH—C(2-12)alkenyl, —NHC(S)NH—C(2-12)alkenyl, —NHC(S)NH—C(3-12)cycloalkyl, —NHC(S)NH-aryl, —NHC(S)NH-heteroaryl, —NHC(S)NH-heterocycloalkyl, —NHC(NH)NH2, NHC(NH)NH—C(1-12)alkyl, —NHC(NH)NH—C(2-12)alkenyl, —NHC(NH)NH—C(2-12)alkenyl, —NHC(NH)NH—C(3-12)cycloalkyl, —NHC(NH)NH-aryl, —NHC(NH)NH-heteroaryl, —NHC(NH)NH-heterocycloalkyl, NHC(NH)—C(1-12)alkyl, —NHC(NH)—C(2-12)alkenyl, —NHC(NH)—C(2-12)alkenyl, —NHC(NH)—C(3-12)cycloalkyl, —NHC(NH)-aryl, —NHC(NH)-heteroaryl, —NHC(NH)-heterocycloalkyl, —C(NH)NH—C(1-12)alkyl, —C(NH)NH—C(2-12)alkenyl, —C(NH)NH—C(2-12)alkenyl, —C(NH)NH—C(3-12)cycloalkyl, —C(NH)NH-aryl, —C(NH)NH-heteroaryl, —C(NH)NH-heterocycloalkyl, —S(O)—C(1-12)alkyl, —S(O)—C(2-12)alkenyl, —S(O)—C(2-12)alkenyl, —S(O)—C(3-12)cycloalkyl, —S(O)-aryl, —S(O)-heteroaryl, —S(O)-heterocycloalkyl-SO$_2$ NH2, —SO$_2$ NH—C(1-12)alkyl, —SO$_2$ NH—C(2-12)alkenyl, —SO$_2$ NH—C(2-12)alkenyl, —SO$_2$ NH—C(3-12)cycloalkyl, —SO$_2$ NH-aryl, —SO$_2$ NH-heteroaryl, —SO$_2$ NHheterocycloalkyl, —NHSO$_2$—C(1-12)alkyl, —NHSO$_2$—C(2-12)alkenyl, —NHSO$_2$—C(2-12)alkenyl, —NHSO$_2$—C(3-12)cycloalkyl, —NHSO$_2$-aryl, —NHSO$_2$-heteroaryl, —NHSO$_2$-heterocycloalkyl, —CH2 NH2, —CH2 SO$_2$ CH3, -aryl, -arylalkyl, -heteroaryl, -heteroarylalkyl, -heterocycloalkyl, —C(3-12)cycloalkyl, -methoxymethoxy, -methoxyethoxy, —SH, —S—C(1-12)alkyl, —S—C(2-12)alkenyl, —S—C(2-12)alkenyl, —S—C(3-12)cycloalkyl, —S-aryl, —S-heteroaryl, -Sheterocycloalkyl, or methylthiomethyl.

As used herein, "acyl" means —C(O)R, wherein R is alkyl or aryl.

The phrase "C(2-12) acyl residues" means groups comprising an acyl group as defined herein, which includes 2 to 12 carbon atoms.

The phrase "C(1-12) acyl halides" means groups that comprise an acyl group, as defined herein, in which the carbonyl group is bonded to a halogen, e.g., acetyl chloride, hexanoyl bromide.

"Aryloxycarbonyl," by itself or as part of another substituent, refers to a radical of the formula —C(O)—O-aryl, where aryl is as defined herein.

"Carbamoyl," by itself or as part of another substituent, refers to a radical of the formula —C(O)NR'R", where R' and R" are each, independently of one another, selected from the group consisting of hydrogen, alkyl and cycloalkyl as defined herein, or alternatively, R' and R", taken together with the nitrogen atom to which they are bonded, form a 5-, 6- or 7-membered cycloheteroalkyl ring as defined herein, which may optionally include from 1 to 4 of the same or different additional heteroatoms selected from the group consisting of O, S and N.

The phrase "C(1-12) carboxylic acids" means groups that comprise 1 to 12 carbon atoms and at least one carboxy group, such as formic acid, acetic acid, propanoic acid, and so on.

The phrase "C(1-12) ethers" means groups that comprise the functional group —OR',
wherein R' consists of C(1-12)alkyl, substituted alkyl, C(2-12)alkenyl, substituted alkenyl, C(2-12)alkynyl, substituted alkynyl, aryl, substituted aryl, heteroaryl, and/or substituted heteroaryl, wherein the oxygen atom in such functional group is bonded to the remainder of the compound.

The phrase "C(1-12)-C(1-12) ethers" means groups that comprise the functional group R'OR", wherein R' and R" separately consist of C(1-12)alkyl, substituted alkyl, C(2-12) alkenyl, substituted alkenyl, C(2-12)alkynyl, substituted alkynyl, aryl, substituted aryl, heteroaryl, and/or substituted heteroaryl.

The phrase "C(1-12) esters" means groups that comprise the functional group —COOR', wherein R' consists of C(1-12)alkyl, substituted alkyl, C(2-12)alkenyl, substituted alkenyl, C(2-12)alkynyl, substituted alkynyl, aryl, substituted aryl, heteroaryl, substituted heteroaryl, alkylamino, and/or dialkylamino, wherein the carbon atom in such functional group is either bonded to, or is part of, the remainder of the compound.

The phrase "C(1-12)-C(1-12) esters" means groups that comprise the functional group R'—COOR", wherein R' and R" separately consist of C(1-12)alkyl, substituted alkyl, C(2-12)alkenyl, substituted alkenyl, C(2-12)alkynyl, substituted alkynyl, aryl, substituted aryl, heteroaryl, substituted heteroaryl, alkylamino, and/or dialkylamino.

The phrase "C(1-12) secondary amides" means groups that comprise the functional group —NHR', wherein R' consists of C(1-12)alkyl, substituted alkyl, C(2-12)alkenyl, substituted alkenyl, C(2-12)alkynyl, substituted alkynyl, aryl, substituted aryl, heteroaryl, and/or substituted heteroaryl, wherein the nitrogen atom is bonded to the remainder of the compound.

The phrase "C(1-12)-C(1-12)tertiary amides" means groups that comprise the functional group —NR'R", wherein R' and R" separately consist of C(1-12)alkyl, substituted alkyl, C(2-12)alkenyl, substituted alkenyl, C(2-12)alkynyl, substituted alkynyl, aryl, substituted aryl, heteroaryl, and/or substituted heteroaryl, wherein the nitrogen atom is bonded to the remainder of the compound.

The phrases "C(1-12) alcohol" and "C(1-12) alcohols" mean groups that comprise the functional group —ROH, wherein R consists of C(1-12)alkyl, C(2-12)alkenyl, or C(2-12) alkynyl, such as —CH2OH, —(CH2)2OH, —(CH2)3OH, and the like.

The terms "halide", "halo" and "halogen," as used herein, mean an atom selected from fluorine, chlorine, bromine and iodine.

"Aryl" and "C(5-12) aryls," as used herein, mean mono- or bicyclic carbocyclic ring systems comprising 5 to 12 carbon atoms, which consist of one or two aromatic rings, including without limitation phenyl, naphthyl, tetrahydronaphthyl, indanyl, idenyl and the like.

The phrase "substituted aryl," as used herein, means an aryl group, as previously defined, substituted by independent replacement or one, two, or three of the hydrogen atoms thereon with substituents including, but not limited to, —F, —Cl, —Br, —I, —OH, protected hydroxy, —NO₂, —CN, —C(1-12)alkyl, —C(-12)alkyl substituted with halogen, C(2-12)alkenyl, C(2-12)alkenyl substituted with halogen, C(2-12)alkynyl optionally substituted with halogen, —NH2, protected amino, —NH—C(1-12)alkyl, —NH—C(2-12)alkenyl, —NH—C(2-12)alkenyl, —NH—C(3-12)cycloalkyl, —NH-aryl, —NH-heteroaryl, —NH-heterocycloalkyl, -dialkylamino, -diarylamino, -diheteroarylamino, —O—C(1-12)alkyl, —O—C(2-12)alkenyl, —O—C(2-12)alkenyl, —O—C(3-12)cycloalkyl, —O-aryl, —O-heteroaryl, —O-heterocycloalkyl, —C(O)—C(1-12)alkyl, —C(O)—C(2-12)alkenyl, —C(O)—C(2-12)alkenyl, —C(O)—C(3-12)cycloalkyl, —C(O)-aryl, —C(O)-heteroaryl, —C(O)-heterocycloalkyl, —CONH2, —CONH—C(1-12)alkyl, —CONH—C(2-12)alkenyl, —CONH—C(2-12)alkenyl, —CONH—C(3-12)cycloalkyl, —CONH-aryl, —CONH-heteroaryl, —CONH-heterocycloalkyl, —OCO₂—C(1-12)alkyl, —OCO₂—C(2-12)alkenyl, —OCO₂—C(2-12)alkenyl, —OCO₂—C(3-12)cycloalkyl, —OCO₂-aryl, —OCO₂-heteroaryl, —OCO₂-heterocycloalkyl, —OCONH2, —OCONH—C(1-12)alkyl, —OCONH—C(2-12)alkenyl, —OCONHC(2-12)alkenyl, —OCONH—C(3-12)cycloalkyl, —OCONH-aryl, —OCONH-heteroaryl, —OCNH-heterocycloalkyl, —NHC(O)—C(1-12)alkyl, —NHC(O)—C(2-12)alkenyl, —NHC(O)—C(2-12)alkenyl, —NHC(O)—C(3-12)cycloalkyl, —NHC(O)-aryl, —NHC(O)-heteroaryl, —NHC(O)-heterocycloalkyl, —NHCO₂—C(1-12)alkyl, —NHCO₂—C(2-12)alkenyl, —NHCO₂—C(2-12)alkenyl, —NHCO₂—C(3-12)cycloalkyl, —NHCO₂-aryl, —NHCO₂-heteroaryl, —NHCO₂-heterocycloalkyl, —NHC(O)NH2, NHC(O)NH—C(1-12)alkyl, —NHC(O)NH—C(2-12)alkenyl, —NHC(O)NH—C(2-12)alkenyl, —NHC(O)NH—C(3-12)cycloalkyl, —NHC(O)NH-aryl, —NHC(O)NHheteroaryl, —NHC(O)NH-heterocycloalkyl, NHC(S)NH2, NHC(S)NH—C(1-12)alkyl, —NHC(S)NH—C(2-12)alkenyl, —NHC(S)NH—C(2-12)alkenyl, —NHC(S)NH—C(3-12)cycloalkyl, —NHC(S)NH-aryl, —NHC(S)NH-heteroaryl, —NHC(S)NH-heterocycloalkyl, —NHC(NH)NH2, NHC(NH)NH—C(1-12)alkyl, —NHC(NH)NH—C(2-12)alkenyl, —NHC(NH)NH—C(2-12)alkenyl, —NHC(NH)NH—C(3-12)cycloalkyl, —NHC(NH)NH-aryl, —NHC(NH)NH-heteroaryl, —NHC(NH)NH-heterocycloalkyl, NHC(NH)—C(1-12)alkyl, —NHC(NH)—C(2-12)alkenyl, —NHC(NH)—C(2-12)alkenyl, —NHC(NH)—C(3-12)cycloalkyl, —NHC(NH)-aryl, —NHC(NH)-heteroaryl, —NHC(NH)-heterocycloalkyl, —C(NH)NH—C(1-12)alkyl, —C(NH)NH—C(2-12)alkenyl, —C(NH)NH—C(2-12)alkenyl, —C(NH)NH—C(3-12)cycloalkyl, —C(NH)NH-aryl, —C(NH)NH-heteroaryl, —C(NH)NH-heterocycloalkyl, —S(O)—C(1-12)alkyl, —S(O)—C(2-12)alkenyl, —S(O)—C(2-12)alkenyl, —S(O)—C(3-12)cycloalkyl, —S(O)-aryl, —S(O)-heteroaryl, —S(O)-heterocycloalkyl-SO₂ NH2, —SO₂ NH—C(1-12)alkyl, —SO₂ NH—C(2-12)alkenyl, —SO₂ NH—C(2-12)alkenyl, —SO₂ NH—C(3-12)cycloalkyl, —SO₂ NH-aryl, —SO₂ NH-heteroaryl, —SO₂ NHheterocycloalkyl, —NHSO₂—C(1-12)alkyl, —NHSO₂—C(2-12)alkenyl, —NHSO₂—C(2-12)alkenyl, —NHSO₂—C(3-12)cycloalkyl, —NHSO₂-aryl, —NHSO₂-heteroaryl, —NHSO₂-heterocycloalkyl, —CH2 NH2, —CH2 SO₂ CH3, -aryl, -arylalkyl, -heteroaryl, -heteroarylalkyl, -heterocycloalkyl, —C(3-12)cycloalkyl, -methoxymethoxy, -methoxyethoxy, —SH, —S—C(1-12)alkyl, —S—C(2-12)alkenyl, —S—C(2-12)alkenyl, —S—C(3-12) cycloalkyl, —S-aryl, —S-heteroaryl, -Sheterocycloalkyl, or methylthiomethyl.

The term "arylalkyl," as used herein, means a C(1-12)alkyl group attached to an aryl ring. Examples include, but are not limited to, benzyl, phenethyl and the like.

The term "substituted arylalkyl," as used herein, means an arylalkyl group, as previously defined, substituted by independent replacement or one, two, or three of the hydrogen atoms thereon with substituents including, but not limited to, —F, —Cl, —Br, —I, —OH, protected hydroxy, —NO₂, CN, —C(1-12)alkyl optionally substituted with halogen, C(2-12) alkenyl optionally substituted with halogen, —C(2-12)alkynyl optionally substituted with halogen, NH2, protected amino, —NH—C(1-12)alkyl, —NHC(2-12)alkenyl, —NH—C(2-12)alkenyl, —NH—C(3-12)cycloalkyl, —NH-aryl, —NH-heteroaryl, —NHheterocycloalkyl, -dialkylamino, -diarylamino, -diheteroarylamino, —O—C(1-12)

alkyl, —O—C(2-12)alkenyl, —O—C(2-12)alkenyl, —O—C(3-12)cycloalkyl, —O-aryl, —O-heteroaryl, -Oheterocycloalkyl, —C(O)—C(1-12)alkyl, —C(O)—C(2-12)alkenyl, —C(O)—C(2-12)alkenyl, —C(O)—C(3-12)cycloalkyl, —C(O)-aryl, —C(O)-heteroaryl, —C(O)-heterocycloalkyl, —CONH2, —CONH—C(1-12)alkyl, —CONH—C(2-12)alkenyl, —CONH—C(2-12)alkenyl, —CONH—C(3-12)cycloalkyl, —CONHaryl, —CONH-heteroaryl, —CONH-heterocycloalkyl, —OCO$_2$—C(1-12)alkyl, —OCO$_2$—C(2-12)alkenyl, —OCO$_2$—C(2-12)alkenyl, —OCO$_2$—C(3-12)cycloalkyl, —OCO$_2$-aryl, —OCO-heteroaryl, —OCO$_2$-heterocycloalkyl, —OCONH2, —OCONH—C(1-12)alkyl, —OCONH—C(2-12)alkenyl, —OCONH—C(2-12)alkenyl, —OCONH—C(3-12)cycloalkyl, —OCONH-aryl, —OCONH-heteroaryl, —OCONH-heterocycloalkyl, —NHC(O)—C(1-12)alkyl, —NHC(O)—C(2-12)alkenyl, —NHC(O)—C(2-12)alkenyl, —NHC(O)—C(3-12)cycloalkyl, —NHC(O)-aryl, —NHC(O)-heteroaryl, —NHC(O)-heterocycloalkyl, —NHCO$_2$—C(1-12)alkyl, —NHCO$_2$—C(2-12)alkenyl, —NHCO$_2$—C(2-12)alkenyl, —NHCO$_2$—C(3-12)cycloalkyl, —NHCO$_2$-aryl, —NHCO$_2$-heteroaryl, —NHCO$_2$-heterocycloalkyl, —NHC(O)NH2, NHC(O)NH—C(1-12)alkyl, —NHC(O)NH—C(2-12)alkenyl, —NHC(O)NH—C(2-12)alkenyl, —NHC(O)NH—C(3-12)cycloalkyl, —NHC(O)NH-aryl, —NHC(O)NHheteroaryl, —NHC(O)NH-heterocycloalkyl, NHC(S)NH2, NHC(S)NH—C(1-12)alkyl, —NHC(S)NH—C(2-12)alkenyl, —NHC(S)NH—C(2-12)alkenyl, —NHC(S)NH—C(3-12)cycloalkyl, —NHC(S)NH-aryl, —NHC(S)NH-heteroaryl, —NHC(S)NH-heterocycloalkyl, —NHC(NH)NH2,NHC(NH)NH—C(1-12)alkyl, —NHC(NH)NH—C(2-12)alkenyl, —NHC(NH)NH—C(2-12)alkenyl, —NHC(NH)NH—C(3-12)cycloalkyl, —NHC(NH)NH-aryl, —NHC(NH)NH-heteroaryl, —NHC(NH)NH-heterocycloalkyl, NHC(NH)—C(1-12)alkyl, —NHC(NH)—C(2-12)alkenyl, —NHC(NH)—C(2-12)alkenyl, —NHC(NH)—C(3-12)cycloalkyl, —NHC(NH)-aryl, —NHC(NH)-heteroaryl, —NHC(NH)-heterocycloalkyl, —C(NH)NH—C(1-12)alkyl, —C(NH)NH—C(2-12)alkenyl, —C(NH)NH—C(2-12)alkenyl, —C(NH)NH—C(3-12)cycloalkyl, —C(NH)NH-aryl, —C(NH)NH-heteroaryl, —C(NH)NH-heterocycloalkyl, —S(O)—C(1-12)alkyl, —S(O)—C(2-12)alkenyl, —S(O)—C(2-12)alkenyl, —S(O)—C(3-12)cycloalkyl, —S(O)-aryl, —S(O)-heteroaryl, —S(O)-heterocycloalkyl-SO$_2$ NH2, —SO$_2$ NH—C(1-12)alkyl, —SO$_2$ NH—C(2-12)alkenyl, —SO$_2$ NH—C(2-12)alkenyl, —SO$_2$NH—C(3-12)cycloalkyl, —SO$_2$NH-aryl, —SO$_2$NH-heteroaryl, —SO$_2$NHheterocycloalkyl, —NHSO$_2$—C(1-12)alkyl, —NHSO$_2$—C(2-12)-alkenyl, —NHSO$_2$—C(2-12)alkenyl, —NHSO$_2$—C(3-12)cycloalkyl, —NHSO$_2$-aryl, —NHSO$_2$-heteroaryl, —NHSO$_2$-heterocycloalkyl, CH2 NH2, —CH2 SO$_2$ CH3, -aryl, -arylalkyl, -heteroaryl, -heteroarylalkyl, -heterocycloalkyl, —C(3-12)cycloalkyl, -methoxymethoxy, -methoxyethoxy, —SH, —S—C(1-12)alkyl, —S—C(2-12)alkenyl, —S—C(2-12)alkenyl, —S—C(3-12)cycloalkyl, —S-aryl, —S-heteroaryl, —S-heterocycloalkyl, or methylthiomethyl.

The term "heteroaryl," as used herein, means a mono-, bi-, or tri-cyclic aromatic radical or ring having from five to ten ring atoms of which one ring atom is selected from S, O and N; zero, one or two ring atoms are additional heteroatoms independently selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The phrase "substituted heteroaryl," as used herein, means a heteroaryl group as previously defined, substituted by independent replacement or one, two, or three of the hydrogen atoms thereon with substituents including, but not limited to, —F, —Cl, —Br, —I, —OH, protected hydroxy, —NO$_2$, —CN, —C(1-12)alkyl optionally substituted with halogen, C(2-12)alkenyl optionally substituted with halogen, —C(2-12)alkynyl optionally substituted with halogen, —NH2, protected amino, —NH—C(1-12)alkyl, —NH—C(2-12)alkenyl, —NH—C(2-12)alkenyl, —NH—C(3-12)cycloalkyl, —NH-aryl, —NH-heteroaryl, —NH-heterocycloalkyl, -dialkylamino, -diarylamino, -diheteroarylamino, —O—C(1-12)alkyl, —O—C(2-12)alkenyl, —O—C(2-12)alkenyl, —OC(3-12)cycloalkyl, —O-aryl, —O-heteroaryl, —O-heterocycloalkyl, —C(O)—C(1-12)alkyl, —C(O)—C(2-12)alkenyl, —C(O)—C(2-12)alkenyl, —C(O)—C(3-12)cycloalkyl, —C(O)-aryl, —C(O)-heteroaryl, —C(O)-heterocycloalkyl, —CONH2, —CONH—C(1-12)alkyl, —CONH—C(2-12)alkenyl, —CONH—C(2-12)alkenyl, —CONH—C(3-12)cycloalkyl, —CONH-aryl, —CONH heteroaryl, —CONH-heterocycloalkyl, —OCO$_2$—C(1-12)alkyl, —OCO$_2$—C(2-12)alkenyl, —OCO$_2$—C(2-12)alkenyl, —OCO$_2$—C(3-12)cycloalkyl, —OCO$_2$-aryl, —OCO$_2$-heteroaryl, —OCO$_2$-heterocycloalkyl, —OCONH2, —OCONH—C(1-12)alkyl, —OCONH—C(2-12)alkenyl, —OCONHC(2-12)alkenyl, —OCONH—C(3-12)cycloalkyl, —OCONH-aryl, —OCONH-heteroaryl, —OCONH heterocycloalkyl, —NHC(O)—C(1-12)alkyl, —NHC(O)—C(2-12)alkenyl, —NHC(O)—C(2-12)alkenyl, —NHC(O)—C(3-12)cycloalkyl, —NHC(O)-aryl, —NHC(O)-heteroaryl, —NHC(O)-heterocycloalkyl, —NHCO$_2$—C(1-12)alkyl, —NHCO$_2$—C(2-12)alkenyl, —NHCO$_2$—C(2-12)alkenyl, —NHCO$_2$—C(3-12)cycloalkyl, —NHCO$_2$-aryl, —NHCO$_2$-heteroaryl, —NHCO$_2$-heterocycloalkyl, —NHC(O)NH2, NHC(O)NH—C(1-12)alkyl, —NHC(O)NH—C(2-12)alkenyl, —NHC(O)NH—C(2-12)alkenyl, —NHC(O)NH—C(3-12)cycloalkyl, —NHC(O)NH-aryl, —NHC(O)NHheteroaryl, —NHC(O)NH-heterocycloalkyl, NHC(S)NH2, NHC(S)NH—C(1-12)alkyl, —NHC(S)NH—C(2-12)alkenyl, —NHC(S)NH—C(2-12)alkenyl, —NHC(S)NH—C(3-12)cycloalkyl, —NHC(S)NH-aryl, —NHC(S)NH-heteroaryl, —NHC(S)NH-heterocycloalkyl, —NHC(NH)NH2, NHC(NH)NH—C(1-12)alkyl, —NHC(NH)NH—C(2-12)alkenyl, —NHC(NH)NH—C(2-12)alkenyl, —NHC(NH)NH—C(3-12)cycloalkyl, —NHC(NH)NH-aryl, —NHC(NH)NH-heteroaryl, —NHC(NH)NH-heterocycloalkyl, NHC(NH)—C(1-12)alkyl, —NHC(NH)—C(2-12)alkenyl, —NHC(NH)C(2-12)alkenyl, —NHC(NH)—C(3-12)cycloalkyl, —NHC(NH)-aryl, —NHC(NH)-heteroaryl, —NHC(NH)-heterocycloalkyl, —C(NH)NH—C(1-12)alkyl, —C(NH)NH—C(2-12)alkenyl, —C(NH)NH—C(2-12)alkenyl, —C(NH)NH—C(3-12)cycloalkyl, —C(NH)NH-aryl, —C(NH)NH-heteroaryl, —C(NH)NH-heterocycloalkyl, —S(O)—C(1-12)alkyl, —S(O)—C(2-12)alkenyl, —S(O)—C(2-12)alkenyl, —S(O)—C(3-12)cycloalkyl, —S(O)-aryl, —S(O)-heteroaryl, —S(O)-heterocycloalkyl-SO$_2$ NH2, —SO$_2$ NH—C(1-12)alkyl, —SO$_2$ NH—C(2-12)alkenyl, —SO$_2$ NH—C(2-12)alkenyl, —SO$_2$ NH—C(3-12)cycloalkyl, —SO$_2$NH-aryl, —SO$_2$NH-heteroaryl, —SO$_2$NHheterocycloalkyl, —NHSO$_2$—C(1-12)alkyl, —NHSO$_2$—C(2-12)alkenyl, —NHSO$_2$—C(2-12)alkenyl, —NHSO$_2$—C(1-12)cycloalkyl, —NHSO$_2$-aryl, —NHSO$_2$-heteroaryl, —NHSO$_2$-heterocycloalkyl, —CH2 NH2, —CH$_2$ SO$_2$ CH3, -aryl, -arylalkyl, -heteroaryl, -heteroarylalkyl, -heterocycloalkyl, —C(3-12)cycloalkyl, -methoxymethoxy, -methoxyethoxy, —SH, —S—C(1-12)alkyl, —S—C(1-12)alkenyl, —S—C(2-12)alkenyl, —S—C(3-12)cycloalkyl, —S-aryl, —S-heteroaryl, -Sheterocycloalkyl, or methylthiomethyl.

The phrase "C(3-12)cycloalkyl," as used herein, means a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl.

The phrase "substituted C(3-12)cycloalkyl," as used herein, means a C(3-12)cycloalkyl group as previously defined, substituted by independent replacement or one, two, or three of the hydrogen atoms thereon with substituents including, but not limited to, —F, —Cl, —Br, —I, —OH, protected hydroxy, —NO$_2$, —CN, —C(1-12)alkyl optionally substituted with halogen, C(2-12)alkenyl optionally substituted with halogen, —C(2-12)alkynyl optionally substituted with halogen, —NH2, protected amino, —NH—C(1-12)alkyl, —NH—C(2-12)alkenyl, —NH—C(2-12)alkenyl, —NH—C(3-12)cycloalkyl, —NH-aryl, —NH-heteroaryl, —NH-heterocycloalkyl, -dialkylamino, -diarylamino, -diheteroarylamino, —O—C(1-12)alkyl, —O—C(2-12)alkenyl, —O—C(2-12)alkenyl, —OC(3-12)cycloalkyl, —O-aryl, —O-heteroaryl, —O-heterocycloalkyl, —C(O)—C(1-12)alkyl, —C(O)—C(2-12)alkenyl, —C(O)—C(2-12)alkenyl, —C(O)—C(3-12)cycloalkyl, —C(O)-aryl, —C(O)-heteroaryl, —C(O)-heterocycloalkyl, —CONH2, —CONH—C(1-12)alkyl, —CONH—C(2-12)alkenyl, —CONH—C(2-12)alkenyl, —CONH—C(3-12)cycloalkyl, —CONH-aryl, —CONH heteroaryl, —CONH-heterocycloalkyl, —OCO$_2$—C(1-12)alkyl, —OCO$_2$—C(2-12)alkenyl, —OCO$_2$—C(2-12)alkenyl, —OCO$_2$—C(3-12)cycloalkyl, —OCO$_2$-aryl, —OCO$_2$-heteroaryl, —OCO$_2$-heterocycloalkyl, —OCONH2, —OCONH—C(1-12)alkyl, —OCONH—C(2-12)alkenyl, —OCONHC(2-12)alkenyl, —OCONH—C(3-12)cycloalkyl, —OCONH-aryl, —OCONH-heteroaryl, —OCONH heterocycloalkyl, —NHC(O)—C(1-12)alkyl, —NHC(O)—C(2-12)alkenyl, —NHC(O)—C(2-12)alkenyl, —NHC(O)—C(3-12)cycloalkyl, —NHC(O)-aryl, —NHC(O)-heteroaryl, —NHC(O)-heterocycloalkyl, —NHCO$_2$—C(1-12)alkyl, —NHCO$_2$—C(2-12)alkenyl, —NHCO$_2$—C(2-12)alkenyl, —NHCO$_2$—C(3-12)cycloalkyl, —NHCO$_2$-aryl, —NHCO$_2$-heteroaryl, —NHCO$_2$-heterocycloalkyl, —NHC(O)NH2, NHC(O)NH—C(1-12)alkyl, —NHC(O)NH—C(2-12)alkenyl, —NHC(O)NH—C(2-12)alkenyl, —NHC(O)NH—C(3-12)cycloalkyl, —NHC(O)NH-aryl, —NHC(O)NHheteroaryl, —NHC(O)NH-heterocycloalkyl, NHC(S)NH2, NHC(S)NH—C(1-12)alkyl, —NHC(S)NH—C(2-12)alkenyl, —NHC(S)NH—C(2-12)alkenyl, —NHC(S)NH—C(3-12)cycloalkyl, —NHC(S)NH-aryl, —NHC(S)NH-heteroaryl, —NHC(S)NH-heterocycloalkyl, —NHC(NH)NH2, NHC(NH)NH—C(1-12)alkyl, —NHC(NH)NH—C(2-12)alkenyl, —NHC(NH)NH—C(2-12)alkenyl, —NHC(NH)NH—C(3-12)cycloalkyl, —NHC(NH)NH-aryl, —NHC(NH)NH-heteroaryl, —NHC(NH)NH-heterocycloalkyl, NHC(NH)—C(1-12)alkyl, —NHC(NH)—C(2-12)alkenyl, —NHC(NH)C(2-12)alkenyl, —NHC(NH)—C(3-12)cycloalkyl, —NHC(NH)-aryl, —NHC(NH)-heteroaryl, —NHC(NH)-heterocycloalkyl, —C(NH)NH—C(1-12)alkyl, —C(NH)NH—C(2-12)alkenyl, —C(NH)NH—C(2-12)alkenyl, —C(NH)NH—C(3-12)cycloalkyl, —C(NH)NH-aryl, —C(NH)NH-heteroaryl, —C(NH)NH-heterocycloalkyl, —S(O)—C(1-12)alkyl, —S(O)—C(2-12)alkenyl, —S(O)—C(2-12)alkenyl, —S(O)—C(3-12)cycloalkyl, —S(O)-aryl, —S(O)-heteroaryl, —S(O)-heterocycloalkyl-SO$_2$ NH2, —SO$_2$ NH—C(1-12)alkyl, —SO$_2$ NH—C(2-12)alkenyl, —SO$_2$ NH—C(2-12)alkenyl, —SO$_2$ NH—C(3-12)cycloalkyl, —SO$_2$ NH-aryl, —SO$_2$ NH-heteroaryl, —SO$_2$ NHheterocycloalkyl, —NHSO$_2$—C(1-12)alkyl, —NHSO$_2$—C(2-12)alkenyl, —NHSO$_2$—C(2-12)alkenyl, —NHSO$_2$—C(1-12)cycloalkyl, —NHSO$_2$-aryl, —NHSO$_2$-heteroaryl, —NHSO$_2$-heterocycloalkyl, —CH2 NH2, —CH2 SO$_2$ CH3, -aryl, -arylalkyl, -heteroaryl, -heteroarylalkyl, -heterocycloalkyl, —C(3-12)cycloalkyl, -methoxymethoxy, -methoxyethoxy, —SH, —S—C(1-12)alkyl, —S—C(1-12)alkenyl, —S—C(2-12)alkenyl, —S—C(3-12)cycloalkyl, —S-aryl, —S-heteroaryl, -Sheterocycloalkyl, or methylthiomethyl.

The term "heterocycloalkyl," as used herein, means a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The phrase "substituted heterocycloalkyl," as used herein, means a heterocycloalkyl group, as previously defined, substituted by independent replacement of one, two, or three of the hydrogen atoms thereon with substituents including, but not limited to, —F, —Cl, —Br, —I, —OH, protected hydroxy, —NO$_2$, —CN, —C(1-12)alkyl optionally substituted with halogen, C(2-12)alkenyl optionally substituted with halogen, —C(2-12)alkynyl optionally substituted with halogen, —NH2, protected amino, —NH—C(1-12)alkyl, —NH—C(2-12)alkenyl, —NH—C(2-12)alkenyl, —NH—C(3-12)cycloalkyl, —NH-aryl, —NH-heteroaryl, —NH-heterocycloalkyl, -dialkylamino, -diarylamino, -diheteroaryl amino, —O—C(1-12)alkyl, —O—C(2-12)alkenyl, —O—C(2-12)alkenyl, —OC(3-12)cycloalkyl, —O-aryl, —O-heteroaryl, —O-heterocycloalkyl, —C(O)—C(1-12)alkyl, —C(O)—C(2-12)alkenyl, —C(O)—C(2-12)alkenyl, —C(O)—C(3-12)cycloalkyl, —C(O)-aryl, —C(O)-heteroaryl, —C(O)-heterocycloalkyl, —CONH2, —CONH—C(1-12)alkyl, —CONH—C(2-12)alkenyl, —CONH—C(2-12)alkenyl, —CONH—C(3-12)cycloalkyl, —CONH-aryl, —CONH heteroaryl, —CONH-heterocycloalkyl, —OCO$_2$—C(1-12)alkyl, —OCO$_2$—C(2-12)alkenyl, —OCO$_2$—C(2-12)alkenyl, —OCO$_2$—C(3-12)cycloalkyl, —OCO$_2$-aryl, —OCO$_2$-heteroaryl, —OCO$_2$-heterocycloalkyl, —OCONH2, —OCONH—C(1-12)alkyl, —OCONH—C(2-12)alkenyl, —OCONHC(2-12)alkenyl, —OCONH—C(3-12)cycloalkyl, —OCONH-aryl, —OCONH-heteroaryl, —OCONH heterocycloalkyl, —NHC(O)—C(1-12)alkyl, —NHC(O)—C(2-12)alkenyl, —NHC(O)—C(2-12)alkenyl, —NHC(O)—C(3-12)cycloalkyl, —NHC(O)-aryl, —NHC(O)-heteroaryl, —NHC(O)-heterocycloalkyl, —NHCO$_2$—C(1-12)alkyl, —NHCO$_2$—C(2-12)alkenyl, —NHCO$_2$—C(2-12)alkenyl, —NHCO$_2$—C(3-12)cycloalkyl, —NHCO$_2$-aryl, —NHCO$_2$-heteroaryl, —NHCO$_2$-heterocycloalkyl, —NHC(O)NH2, NHC(O)NH—C(1-12)alkyl, —NHC(O)NH—C(2-12)alkenyl, —NHC(O)NH—C(2-12)alkenyl, —NHC(O)NH—C(3-12)cycloalkyl, —NHC(O)NH-aryl, —NHC(O)NHheteroaryl, —NHC(O)NH-heterocycloalkyl, NHC(S)NH2, NHC(S)NH—C(1-12)alkyl, —NHC(S)NH—C(2-12)alkenyl, —NHC(S)NH—C(2-12)alkenyl, —NHC(S)NH—C(3-12)cycloalkyl, —NHC(S)NH-aryl, —NHC(S)NH-heteroaryl, —NHC(S)NH-heterocycloalkyl, —NHC(NH)NH2, NHC(NH)NH—C(1-12)alkyl, —NHC(NH)NH—C(2-12)

alkenyl, —NHC(NH)NH—C(2-12)alkenyl, —NHC(NH) NH—C(3-12)cycloalkyl, —NHC(NH)NH-aryl, —NHC (NH)NH-heteroaryl, —NHC(NH)NH-heterocycloalkyl, NHC(NH)—C(1-12)alkyl, —NHC(NH)—C(2-12)alkenyl, —NHC(NH)C(2-12)alkenyl, —NHC(NH)—C(3-12)cycloalkyl, —NHC(NH)-aryl, —NHC(NH)-heteroaryl, —NHC(NH)-heterocycloalkyl, —C(NH)NH—C(1-12) alkyl, —C(NH)NH—C(2-12)alkenyl, —C(NH)NH—C(2-12)alkenyl, —C(NH)NH—C(3-12)cycloalkyl, —C(NH) NH-aryl, —C(NH)NH-heteroaryl, —C(NH)NH-heterocycloalkyl, —S(O)—C(1-12)alkyl, —S(O)—C(2-12) alkenyl, —S(O)—C(2-12)alkenyl, —S(O)—C(3-12) cycloalkyl, —S(O)-aryl, —S(O)-heteroaryl, —S(O)-heterocycloalkyl-SO$_2$ NH2, —SO$_2$ NH—C(1-12)alkyl, —SO$_2$ NH—C(2-12)alkenyl, —SO$_2$ NH—C(2-12)alkenyl, —SO$_2$ NH—C(3-12)cycloalkyl, —SO$_2$NH-aryl, —SO$_2$ NH-heteroaryl, —SO$_2$ NHheterocycloalkyl, —NHSO$_2$—C(1-12) alkyl, —NHSO$_2$—C(2-12)alkenyl, —NHSO$_2$—C(2-12)alkenyl, —NHSO$_2$—C(1-12)cycloalkyl, —NHSO$_2$-aryl, —NHSO$_2$-heteroaryl, —NHSO$_2$-heterocycloalkyl, —CH2 NH2, —CH2 SO$_2$ CH3, -aryl, -arylalkyl, -heteroaryl, -heteroarylalkyl, -heterocycloalkyl, —C(3-12)cycloalkyl, -methoxymethoxy, -methoxyethoxy, —SH, —S—C(1-12)alkyl, —S—C(1-12)alkenyl, —S—C(2-12)alkenyl, —S—C(3-12) cycloalkyl, —S-aryl, —S-heteroaryl, -Sheterocycloalkyl, or methylthiomethyl.

The term "alkylamino" means a group having the structure —NH(C(1-12)alkyl), wherein C(1-12)alkyl is as previously defined.

The phrase "C(1-3)alkyl-amino," as used herein, means one or two C(1-12)alkyl groups, as previously defined, comprising 1 to 3 carbons each, attached to the parent molecular moiety through a nitrogen atom. Examples of C(1-3)alkylamino include, but are not limited to, methylamino, dimethylamino, ethylamino, diethylamino, and propylamino.

As used herein, "dialkylamino" or "monoalkylamino," by themselves or as part of other substituents, mean radicals of the formula —NRR and —NHR, respectively, where each R is independently selected from the group consisting of alkyl and cycloalkyl, as defined herein. Representative examples of dialkylamino groups include, but are not limited to, dimethylamino, methylethylamino, di-(1-methylethyl)amino, (cyclohexyl)(methyl)amino, (cyclohexyl)(ethyl)amino, (cyclohexyl)(propyl)amino and the like. Representative examples of monalkylamino groups include, but are not limited to, methylamino, ethylamino, propylamino, isopropylamino, cyclohexylamino, and the like.

The term "carboxaldehyde," as used herein, means a group of formula —CHO.

The term "carboxy," as used herein, means a group of formula —COOH.

The term "hydroxy," as used herein, means a group of formula —OH.

"Sulfamoyl," by itself or as part of another substituent, refers to a radical of the formula —S(O)$_2$ NR'R", where R' and R" are each, independently of one another, selected from the group consisting of hydrogen, alkyl and cycloalkyl as defined herein, or alternatively, R' and R", taken together with the nitrogen atom to which they are bonded, form a 5-, 6- or 7-membered cycloheteroalkyl ring as defined herein, which may optionally include from 1 to 4 of the same or different additional heteroatoms selected from the group consisting of O, S, and N.

The phrase "hydroxy protecting group," as used herein, means a labile chemical moiety which is known in the art to protect a hydroxyl group against undesired reactions during synthetic procedures. Following such procedures, the hydroxy protecting group may be selectively removed. Examples of hydroxy protecting groups include, but are not limited to, methylthiomethyl, tert-butyldimethylsilyl, tertbutyldiphenylsilyl, acyl substituted with an aromatic group, and the like.

The phrase "protected hydroxy," as used herein, means a hydroxy group protected with a hydroxy protecting group, as defined above, including benzoyl, acetyl, trimethylsilyl, triethylsilyl, methoxymethyl groups, for example.

The phrase "amino protecting group," as used herein, means a labile chemical moiety which is known in the art to protect an amino group against undesired reactions during synthetic procedures. Following such procedures, the amino protecting group may be selectively removed. Examples of amino protecting groups include, but are not limited to, t-butoxycarbonyl, 9-fluorenylmethoxycarbonyl, benzyloxycarbonyl, and the like.

The phrase "protected amino," as used herein, means an amino group protected with an amino protecting group as defined above.

COMPOUNDS USED IN THE INVENTION

In accordance with the present invention, a group of pentacyclic acid triterpene compounds that is surprisingly effective in inhibiting the formation of biofilms, reducing existing biofilms and inhibiting bacterial infections is disclosed. The biofilm inhibiting activity of the pentacyclic acid triterpenes was previously unappreciated. Since the pentacyclic acid triterpenes that inhibit biofilm formation do not directly inhibit the growth of many bacteria outside of an infected host, the use of the pentacyclic acid triterpene compounds in inhibiting the growth of those same bacteria in an infected host was also unappreciated. Furthermore, it is also disclosed that the co-administration of a pentacyclic acid triterpene compound with an antimicrobial agent or antibiotic to a bacterial biofilm provides increased susceptibility of the bacteria to the antibiotic. The instant invention thus provides for novel pentacyclic acid triterpene compounds, compositions comprising pentacyclic acid triterpenes, compositions comprising pentacyclic acid triterpenes and antimicrobial agents or antibiotics, and various methods of using pentacyclic acid triterpene compositions to control biofilms or bacterial infections.

The broad group of compounds useful in the practice of this invention are collectively referred to herein as pentacyclic acid triterpenes. Pentacyclic acid triterpenes are defined in the context of this invention to encompass any compounds that have either the ursane or oleanane triterpene scaffolds depicted below and in FIG. 2 wherein C28 is a carboxylic acid. More preferably, these compounds will have a carboxylic acid at position 28, a single, unsubstituted methyl at positions 25, 26, 27, 29, and 30 and a single unsubstituted or substituted methyl at positions 23 and 24 of either the Ursane or Oleanane scaffold shown below.

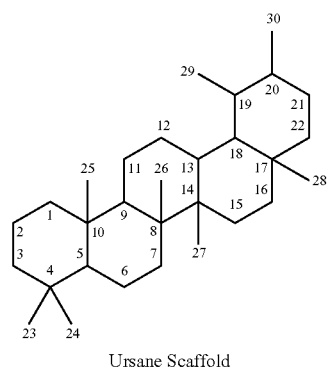

Ursane Scaffold

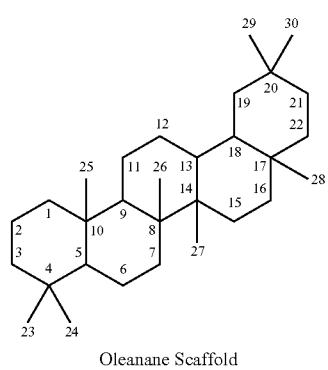

Oleanane Scaffold

The following exemplary pentacyclic acid triterpene compounds have been shown to prevent or inhibit biofilms and/or to prevent or inhibit bacterial infections:

Compound 99 (30-hydroxyursolic acid)

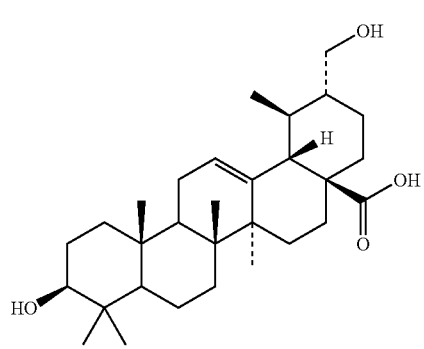

Compound 107 (2-hydroxyoleanic acid)

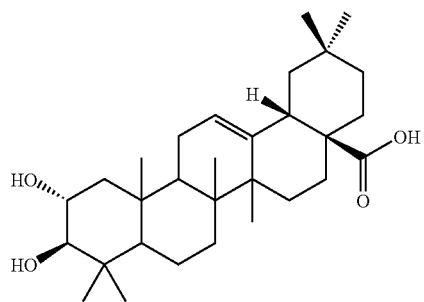

Compound 108 (Corosolic Acid)

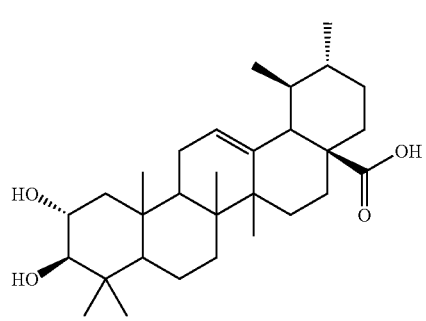

Compound 110 (Ursolic Acid)

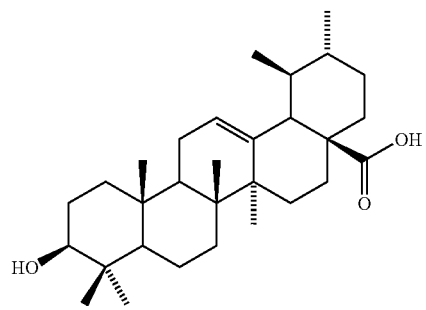

Compound 116 (-3-O-[3-hydroxy, 4-methoxy-cinnamoyl(trans-)]-2hydroxyursolic acid)

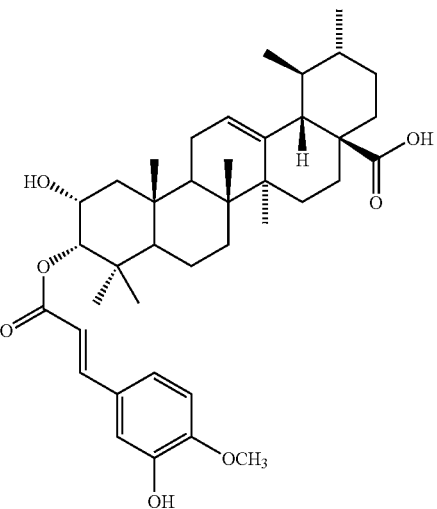

Compound 188 (3-[4-Hydroxycinnamoyl(cis-)], 20-hydroxy-ursolic acid)
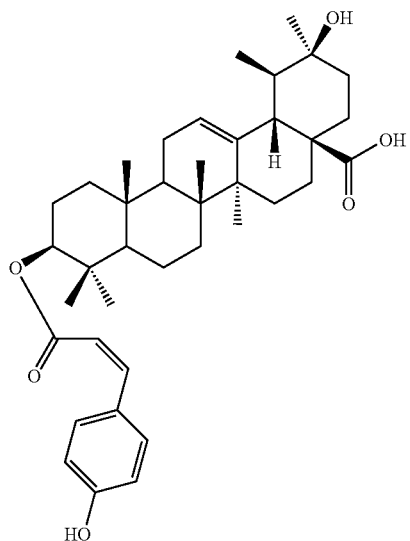
Compound 189 (3-[4-hydroxycinnamoyl(trans-)]-2-hydroxyursolic acid)
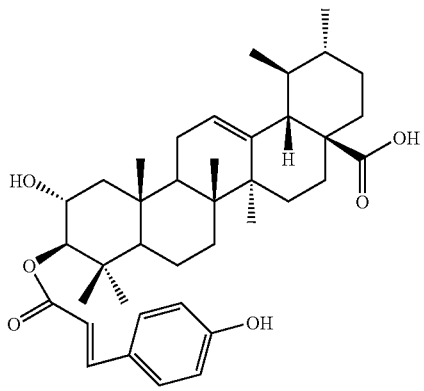
Compound 190 (3-[4-hydroxycinnamoyl(cis-)]-2-hydroxyursolic acid)
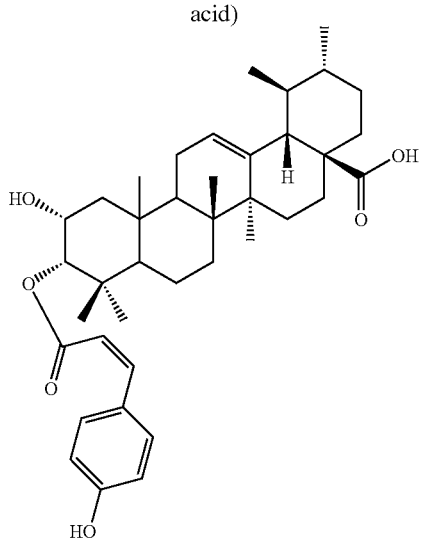
Compound 192 (Euscaphic Acid)
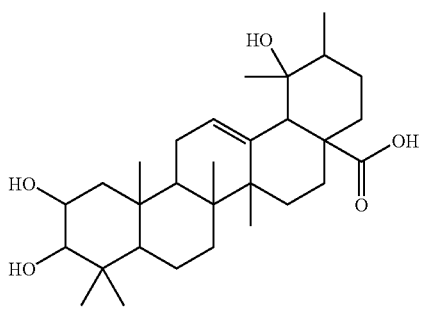
Compound 195 (20B-hydroxyursolic acid)
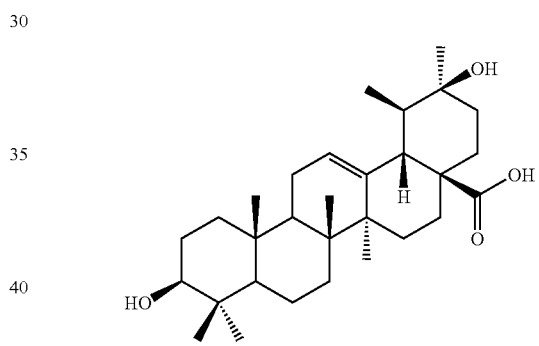
Compound 203 (Tormentic Acid)
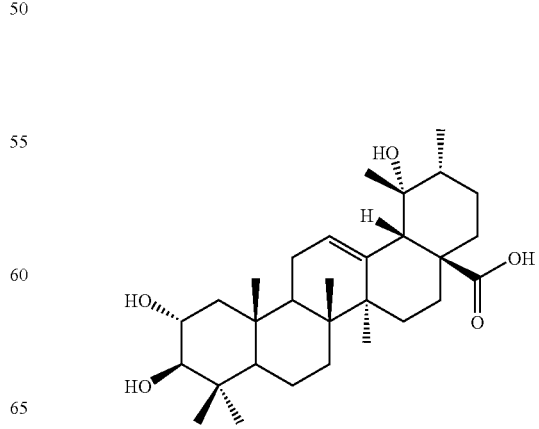

Compound 225 (Oleanolic Acid)
Compound 323 (Caulophyllogenin)
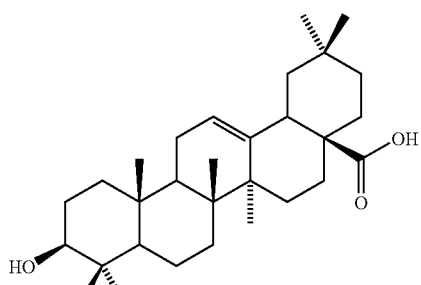
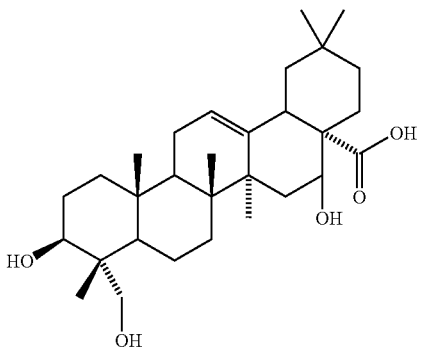
Compound 255 (Asiatic Acid)
Compound 456 (Pygenic Acid A)
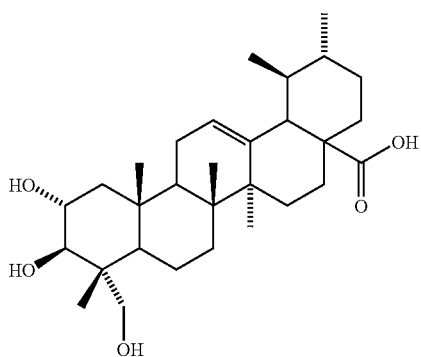
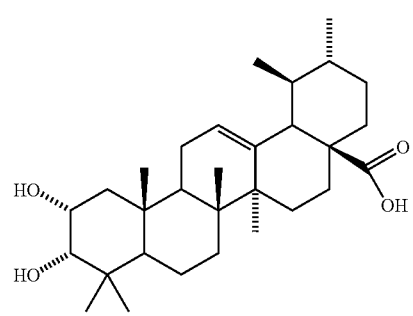
Compound 314 (Madecassic Acid)
Compound 457 (Pygenic Acid B)
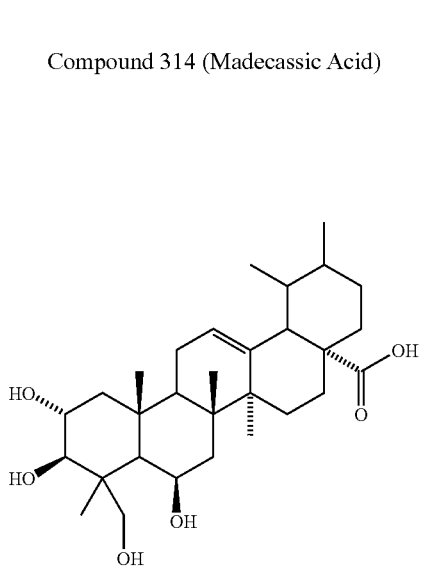
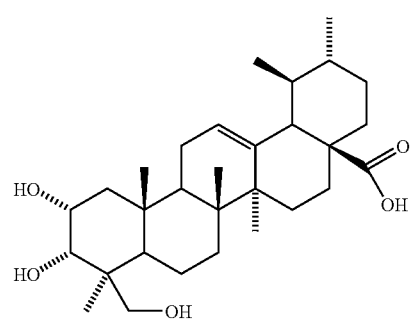

29
Compound 458 (Pygenic Acid C)
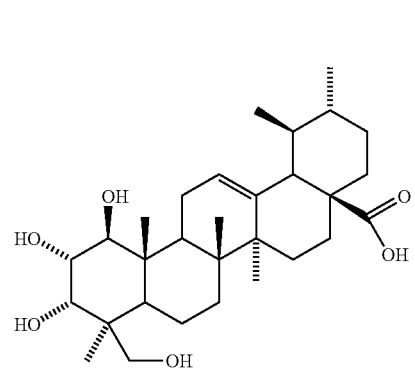
Compound 430 (3-hydroxy-12,20(30) ursadien-28-oic acid)
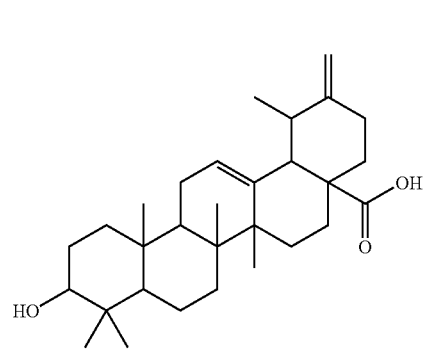
Compound 455 (Echinocystic Acid)
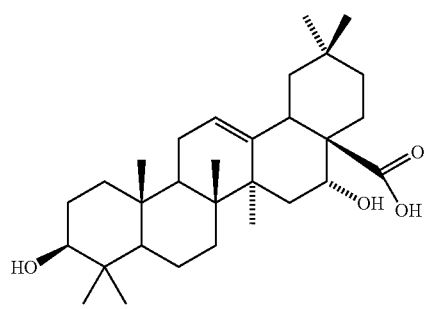
30
Compound 480 (3-acetyl oleanolic acid)
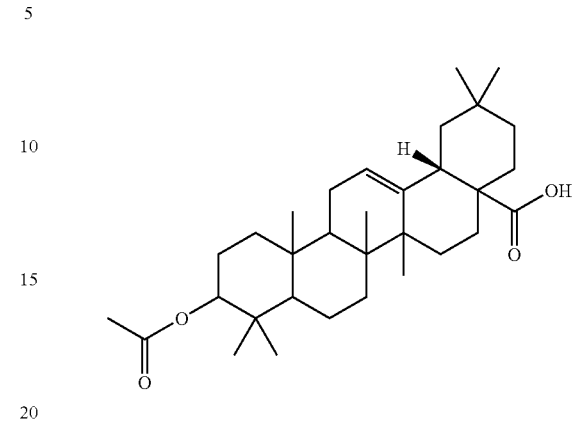
3β-O-tert-butyloxycarbonyl-ursolic acid
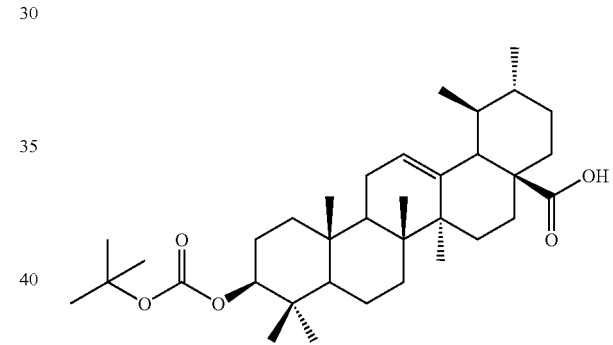
2β-methoxyl-3α-cinnamoyl-ursolic acid
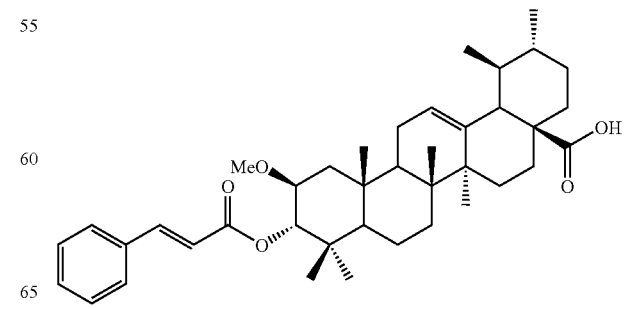

Compound 410
(2β-methoxy-3α-hydroxy-12-ursen-28-oic acid)

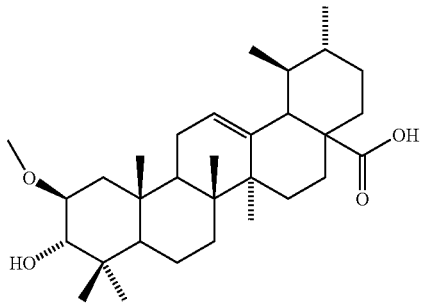

Compound 431 (2β,3α-dihydroxy-12-ursen-28-oic acid)

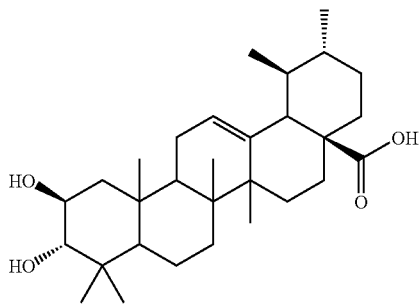

Having discovered that the preceding pentacyclic acid triterpene compounds containing either the Ursane or Oleanane scaffold structure (FIG. 1) are capable of inhibiting biofilm formation, this invention further recognizes that pentacyclic acid triterpenes containing either the Ursane or Oleanane scaffold structure can be modified or derivatized to yield other pentacyclic acid triterpene compounds that are also capable of inhibiting biofilm formation. The other pentacyclic acid triterpene compounds that inhibit biofilm formation may be novel pentacyclic acid triterpenes. In particular, structure-activity analysis of the naturally occurring pentacyclic acid triterpene biofilm inhibition activity provides for the instant invention of novel compounds of the current invention containing substitutions at key scaffold positions. This invention thus discloses that certain substitutions at either the C2 or C3 positions of either the Ursane or Oleanane scaffolds provide novel compounds that inhibit biofilm formation. The invention further discloses substituting R groups and stereochemical configurations at both the C2 or C3 positions for obtaining novel pentacyclic acid triterpene compounds that inhibit biofilm formation. These derivatives are described by the following chemical Structure I wherein $R^1$ is selected from the group consisting of hydrogen, hydroxyl, halide, methoxy, acetoxy, —$CH_2$ OH, —$CH_2$ $CH_2OH$, —CN, —$C_{1-2}$(halo)alkyl, —$CH_2$ Cl, —C(O)H, —C(O)$NH_2$, —SH, $CF_3$, $CCl_3$, and —NAA, wherein each A is independently selected from the group consisting of H and $C_1$-$C_2$ alkyl; $R^2$ is selected from the group consisting of hydroxyl, halide, —CN, —C(O)$NH_2$, —SH, —S(O)$NH_2$, $CF_3$, $CCl_3$, —NYY, wherein each Y is independently selected from H or $C_1$-$C_5$ alkyl, $C_{1-5}$ acyl halides, —$C_{1-5}$(halo)alkyl, $C_{1-5}$ acyl residues, $C_{2-5}$ secondary amides, ($C_{1-5}$)($C_{1-5}$)tertiary amides, $C_{1-5}$ alcohols, $C_{1-5}$ substituted alkyls, $C_{2-5}$ alkenyls, and $C_{2-5}$ substituted alkenyls, —OC(O)—OC($CH_3$)$_3$, —OC(O)—CH=CH-phenyl, —OC(O)—R, wherein R is an unbranched or branched $C_1$-$C_5$ alkyl, and —OC(O) $C_{1-5}R^5R^6$ wherein $R^5$ is an alkylene or alkenylene of up to 5 carbons and $R^6$ is selected from the group consisting of substituted and unsubstituted $C_{5-7}$ aromatics, substituted and unsubstituted $C_{5-7}$ cycloalkyls, and substituted and unsubstituted $C_{5-7}$ heterocycloalkyls, provided that: i) $R^2$ is not hydroxyl when $R^1$ is hydrogen, hydroxyl, methoxy, chloride or —CN; ii) $R^2$ is not chloride or —OC(O)$CH_3$ when $R^1$ is hydrogen; iii) $R^2$ is not —OC(O)—CH=CH-(m-hydroxy, p-methoxy-phenyl) or —OC(O)—CH=CH-(p-hydroxy-phenyl) when $R^1$ is hydroxyl; and iv) $R^2$ is not $C_{1-5}$ substituted alkyl, —$C_{1-5}$(halo)alkyl, or $C_{1-5}$ alcohol when $R^1$ is hydrogen, halide, hydroxyl, methoxy, acetoxy or —SH; and wherein one of $R^3$ and $R^4$ is hydrogen and the other is methyl. Salts, hydrates, solvates, prodrugs and N-oxides of the novel pentacyclic acid triterpene compounds are also contemplated by the present invention. As demonstrated herein, such compounds are useful in controlling bacterial infections and/or biofilm formation in a variety of subjects including animals such as mammals and human patients as well as plants.

Structure I

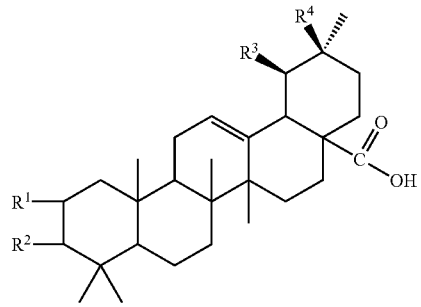

In other embodiments, positions C23 and -24 and C6, C16,-19, and C20 may be derivatized to enhance biofilm inhibition activity of the pentacyclic acid triterpene compounds encompassed by and used in the present invention. These derivatives are described by the following chemical chemical Structure II wherein $R^1$ is selected from the group consisting of hydrogen, hydroxyl, halide, methoxy, acetoxy, —$CH_2$ OH, —$CH_2$ $CH_2OH$, —CN, —$C_{1-2}$(halo)alkyl, —$CH_2$ Cl, —C(O)H, —C(O)$NH_2$, —SH, $CF_3$, $CCl_3$, and —NAA, wherein each A is independently selected from the group consisting of H and $C_1$-$C_2$ alkyl; $R^2$ is selected from the group consisting of hydroxyl, halide, —CN, —C(O)$NH_2$, —SH, —S(O)$NH_2$, $CF_3$, $CCl_3$, —NYY, wherein each Y is independently selected from H or $C_1$-$C_5$ alkyl, $C_{1-5}$ acyl halides, —$C_{1-5}$(halo)alkyl, $C_{1-5}$ acyl residues, $C_{2-5}$ secondary amides, ($C_{1-5}$)($C_{1-5}$)tertiary amides, $C_{1-5}$ alcohols, $C_{1-5}$ substituted alkyls, $C_{2-5}$ alkenyls, and $C_{2-5}$ substituted alkenyls, substituted or unsubstituted $C_{5-7}$ aromatics, —OC(O)—OC($CH_3$)$_3$, —OC(O)—CH=CH-phenyl, —OC(O)—R, wherein R is an unbranched or branched $C_1$-$C_5$ alkyl, and —OC(O) $C_{1-5}R^{13}R^{14}$ wherein $R^{13}$ is an alkylene or alkenylene of up to 5 carbons and $R^{14}$ is selected from the group consisting of substituted and unsubstituted $C_{5-7}$ aromatics, substituted and unsubstituted $C_{5-7}$ cycloalkyls, and substituted and unsubstituted $C_{5-7}$ heterocycloalkyls; provided that: i) $R^2$ is not hydroxyl when $R^1$ is hydrogen, hydroxyl, methoxy, chloride or —CN; ii) $R^2$ is not chloride or —OC(O)$CH_3$ when $R^1$ is hydrogen; iii) $R^2$ is not —OC(O)—CH=CH-(m-hydroxy, p-methoxy-phenyl) or —OC(O)—CH=CH-(p-hydroxy-phenyl) when $R^1$ is hydroxyl; and iv) $R^2$ is not $C_{1-5}$ substituted alkyl, —$C_{1-5}$(halo)alkyl, or $C_{1-5}$ alcohol when $R^1$ is hydrogen, halide, hydroxyl, methoxy, acetoxy or —SH; $R^3$ is selected from the group consisting of hydrogen, methyl, halide, and —$NH_2$; $R^4$ is selected from the group consisting of hydrogen, methyl, hydroxyl, halide, $C_{1-3}$ alkoxy, —CN, —$NH_2$, —C(O)H, —C(O)$NH_2$, —SH, —S(O)$NH_2$, carboxylic acid groups, $C_{1-3}$ acyl halides, $C_{1-3}$ acyl residues, $C_{2-3}$ secondary amides, $C_{1-3}$ alcohols, ($C_{1-2}$)($C_{1-2}$) ethers, $C_{2-3}$ alkyls, $C_{1-3}$ substituted alkyls, $C_{2-3}$ alkenyls, and $C_{2-3}$ substituted alkenyls; $R^5$, and $R^{12}$ are independently selected from the group consisting of hydrogen, hydroxyl, halide, $C_{1-3}$ alkoxy, —CN, —$NH_2$, —C(O)$NH_2$, —OC(O)$C_{1-3}$, —SH, —S(O)$NH_2$, and —$C_{1-3}$(halo)alkyl; $R^6$ and $R^7$ are independently selected from the group consisting of hydrogen, hydroxyl, halide, and —$NH_2$; one of $R^8$ and $R^{10}$ is hydrogen and the other is methyl; and $R^9$ and $R^{11}$ are independently selected from the group consisting of hydrogen, methyl, hydroxyl, halide, $C_{1-3}$ alkoxy, —$NH_2$, and —CN. Salts, hydrates, solvates, prodrugs and N-oxides of the novel pentacyclic acid triterpene compounds of Structure II are also contemplated by the present invention.

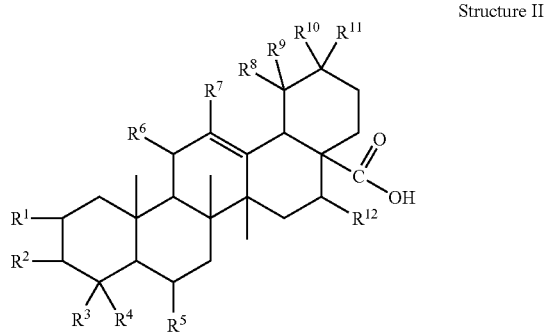

Structure II

Alternatively, the other pentacyclic acid triterpene compounds that inhibit biofilm formation may be pentacyclic acid triterpenes derivatives that have previously been disclosed for other uses. For example, U.S. Pat. No. 5,834,437 (herein incorporated by reference in its entirety) discloses various derivatives of Asiatic acid and Madecassic acid at the C-2 and C-3 positions of those pentacyclic triterpenes for use as wound healing agents. U.S. Pat. No. 6,369,101 B1 (herein incorporated by reference in its entirety) discloses various derivatives at the C-2 and C-3 positions of a pentacyclic acid triterpene for use in treating herpes virus infections. U.S. Patent Application publication US 2005/0137259 A1 (herein incorporated by reference in its entirety) discloses methods of obtaining acyl derivatives the C-2 and/or C-3 positions of corosolic acid, maslinic acid, ursolic acid and oleanolic acid as early insulin secretion stimulators. This instant invention contemplates previously unappreciated uses of these disclosed pentacyclic acid triterpenes in novel compositions comprising the pentacyclic acid triterpene and an antimicrobial agent. This instant invention further contemplates previously unappreciated methods of using the disclosed pentacyclic acid triterpenes to inhibit or prevent biofilms and to inhibit or prevent bacterial infections.

The compounds described herein to be useful in practicing the invention contain one or more asymmetric centers and thus give rise to enantiomers, diastereomers, and other stereoisomeric forms that may be defined, in terms of absolute stereochemistry, as (R)- or (S)-. Stereoisomeric forms may alternatively be defined as being in the α configuration or β-configuration relative to the chiral carbon in the nomenclature typically adopted in natural product chemistry descriptions. The present invention encompasses all such possible isomers, as well as their racemic and optically pure forms. Optical isomers may be prepared from their respective optically active precursors using the procedures described herein, or by resolving the racemic mixtures. The resolution can be carried out in the presence of a resolving agent, by chromatography or by repeated crystallization or by some combination of these techniques which are known to those skilled in the art.

It has further been found that particular stereochemical configurations of the $R^1$ and $R^2$ groups respectively located at the chiral carbons C-2 and C-3 of the ursane or oleanane scaffolds are preferred in the practice of this invention. More specifically, the $R^1$ group may be in the α configuration relative to the chiral carbon C-2 in the nomenclature typically adopted in natural product chemistry descriptions. The $R^2$ group may be in the β-configuration relative to the chiral carbon C-3 in the nomenclature typically adopted in natural product chemistry descriptions.

In another embodiment, the $R^1$ group is in the αconfiguration relative to the chiral carbon C-2 and the $R^2$ group is in the α-configuration relative to the chiral carbon C-3. This configuration is observed in Pygenic acid B. Biofilm inhibitory activity associated with these compounds is described in the examples of the specification.

In another embodiment of the invention is $R^1$ group is in the β configuration relative to the chiral carbon C-2 and the $R^2$ group is in the α-configuration relative to the chiral carbon C-3. This configuration is observed in 2β-methoxy-3α-cinnamoyl-12-ursen-28-oic acid, 30-O-tert-butyloxycarbonyl-ursolic acid, 2β-methoxy-3α-hydroxy-12-ursen-28-oic acid, and 2β,3α-dihydroxy-12-ursen-28-oic acid. Biofilm inhibitory activity associated with these compounds is described in the examples of the specification.

When the compounds described herein contain olefinic double bonds, other unsaturation, or other centers of geometric asymmetry, and unless specified otherwise, it is intended that the compounds include both E and Z geometric isomers or cis- and trans-isomers. Similarly, all tautomeric forms are intended to be encompassed by the present invention. The cis-trans configuration relative to any double bond appearing herein is selected for convenience only and is not intended to designate a particular configuration unless the text so states; thus, the cis or trans configuration is depicted arbitrarily herein and notwithstanding the configuration shown, may be cis, trans, or a mixture of the two in any proportion.

Methods of Isolation, Purification, and Modification

A key feature of this invention is that it further provides methods for obtaining the pentacyclic acid triterpene compounds.

The pentacyclic acid triterpene compounds disclosed herein may be obtained by modifying known pentacyclic acid triterpene compounds obtained from natural sources or purchased from commercial vendors. Alternatively, the pentacyclic acid triterpene compounds disclosed herein may be obtained by modifying a known pentacyclic acid triterpene compound obtained by direct synthesis. Furthermore, the known pentacyclic acid triterpene compounds obtainable from any of the sources described may be separated and purified using methods such as column chromatography, high pressure liquid chromatography, and/or recrystallization prior to their modification to yield the desired novel pentacyclic acid triterpenes of this invention. As will be appreciated by the skilled artisan, further methods of synthetically producing and derivatizing or modifying the compounds disclosed herein will be evident to those of ordinary skill in the art. Additionally, the various isolation, purification, and/or synthetic steps may be performed in an alternate sequence or order to produce the desired compounds.

Many of the known pentacyclic acid triterpenes used herein as precursors to the novel pentacyclic acid triterpenes described herein may be isolated and purified from a natural source such as plants or materials derived from plants. Alternatively, the known pentacyclic acid triterpene precursors can often be obtained from commercial sources. Ursolic Acid (Compound 110) is particularly useful known pentacyclic acid triterpene that can be used as a precursor to certain novel pentacyclic acid triterpene compounds of the present invention. Ursolic acid can be obtained either from plants such as those listed in Table 1 or from commercial sources (Sigma-Aldrich, St. Louis, Mo.). Oleanolic acid (Compound 225) is another particularly useful known pentacyclic acid triterpene that can be used as a precursor to certain novel pentacyclic acid triterpene compounds of the present invention. Oleanolic Acid can also be obtained either from plants such as those listed in Table 1 or from commercial sources (Sigma-Aldrich, St. Louis, Mo.).

of this invention and specifically applicable to purifying certain pentacyclic acid triterpenes are known. Nishimura, et al. (J. Nat. Prod. 1999, 62, 1061-1064) described the identification of 2,3-dihydroxy-24-nor-urs-4(23),12-dien-28-oic acid and 23-hydroxyursolic acid. It is now apparent from the written descriptions contained herein that these compounds will inhibit the formation of biofilms using the procedures described in the examples. Nishimura described procedures to isolate these compounds. Procedures described herein demonstrate these compounds will be contained in flash chromatography fraction 3 (FCF3) as described in the examples. Similar HPLC procedures described herein can be used to further purify these compounds including using a gradient with water with 0.05% TFA and acetonitrile with 0.05% TFA, mobile phase A and B respectively, with a C18 BetaMax Neutral column (250×8 mm; 5 um). The gradient may consist of 40% β isocratic for 5 min, then from approximately 40% to 70% B in 30 min. A skilled artisan would recognize the general applicability of the methods described in Nishimura et al to efficiently isolate either the pentacyclic acid triterpene compounds described herein or structurally related pentacyclic acid triterpenes from various plants and that these compounds will exhibit biofilm inhibition using the procedures described in the examples.

TABLE ONE

Plant Sources of Pentacyclic Acid Triterpene Compounds

| Compound | Compound Number | Plant Species |
| --- | --- | --- |
| 30-hydroxyursolic acid | 99 | *Arctostaphylos tomentosa* (California, USA); *Arctostaphylos edmundsii* (California, USA); and *Phyla nodiflora* (Texas, USA) |
| 2-hydroxyoleanolic acid | 107 | *Diospyros dendo* (Gabon, Africa) |
| Corosolic acid | 108 | *Diospyros dendo* (Gabon, Africa) |
| Ursolic acid | 110 | *Diospyros dendo* (Gabon, Africa); *Arctostaphylos tomentosa* (California, USA); *Arctostaphylos edmundsii* (California, USA); and *Malus domestica* (California, USA). |
| -3-O-[3-hydroxy, 4-methoxy-cinnamoyl(trans-)]-2hydroxyursolic acid | 116 | *Diospyros dendo* (Gabon, Africa) |
| 3-[4-Hydroxycinnamoyl (cis-)], 20-hydroxy-ursolic acid | 188 | *Diospyros dendo* (Gabon, Africa) |
| 3-[4-hydroxycinnamoyl(trans-)]-2-hydroxyursolic acid | 189 | *Diospyros dendo* (Gabon, Africa); and *Malus domestica* (California, USA) |
| 3-[4-hydroxycinnamoyl(cis-)]-2-hydroxyursolic acid | 190 | *Diospyros dendo* (Gabon, Africa) |
| Euscaphic acid | 192 | *Brazzeia soyauxii* (Gabon, Africa) |
| 20B-hydroxyursolic acid | 195 | *Arctostaphylos tomentosa* (California, USA); and *Arctostaphylos edmundsii* (California, USA); |
| Tormentic acid | 203 | *Brazzeia soyauxii* (Gabon, Africa) |
| Asiatic acid | 255 | *Centella asiatica* (Florida, USA) |
| Madecassic acid | 314 | *Centella asiatica* (Florida, USA) |
| Pygenic acid A | 456 | *Pygeum africanum* |
| Pygenic acid B | 457 | *Pygeum africanum* |
| 3-hydroxy-12, 20(30) ursadienoic acid | 430 | *Hyptis emoryi* (California, USA) |
| Oleanolic acid | 225 | *Vitis* L. spp.; *Crataegus* L.spp. |
| Caulophyllogenin | 323 | *Caulophyllum* spp. |
| Echinocystic acid | 455 | *Albizia* spp. |
| 3-acetyl oleanolic acid | 480 | *Drosera intermedia* |

A variety of illustrative methods that are generally applicable to purifying the pentacyclic acid triterpene compounds Other illustrative methods that are generally applicable to purifying other pentacyclic acid triterpenes and specifically applicable to purifying certain pentacyclic acid triterpenes are also known. Ballesta-Acosta, et al. (J. Nat. Prod. 2002, 65, p. 1513-1515) described the identification of 2,3-dihydroxy-24-nor-4(23),12-oleanadien-28-oic acid. Begum, et al. (J. Nat. Prod. 1997, 60, p. 20-23) described the isolation of camaldulenic acid also listed at 2,3-dihydroxyolean-11,13 (18)-dien-28-oic acid and other related compounds. Chaturvedula, et al. (J. Nat. Prod. 2004, 67, p. 899-901) described the isolation of 3-acetoxy-2-hydroxy ursolic acid, 3-(p-coumaroyl)ursolic acid, and 2,3-diacetoxyursolic acid. Adnyana, et al. (J. Nat. Prod. 2001, 64, p. 360-363) described the isolation of 2,3,6,19-tetrahydroxyoleanolic acid, 2,3,19-trihydroxyoleanolic acid, 2,3,19,23-tetrahydroxyursolic acid, and 2,3,23-trihydroxyoleanolic acid. Ikuta, et al. (J. Nat. Prod. 2003, 66, p. 1051-1054) described the isolation of 2,3-dihydroxyurs-12-en-11-on-28-oic acid and 2,3-dihydroxy-11-methoxyurs-12-en-28-oic acid. Procedures described herein demonstrate these compounds will be contained in FCF3. Similar HPLC procedures described herein can be used to further purify these compounds including using a gradient with water with 0.05% TFA and acetonitrile with 0.05% TFA, mobile phase A and B respectively, with a C18 BetaMax Neutral column (250×8 mm; 5 um). The gradient may consist of 40% β isocratic for 5 min, then from approximately 40% to 70% B in 30 min. A skilled artisan now understands how the written description contained herein can be used to efficiently isolate these known pentacyclic acid triterpene precursor compounds and that these compounds can be further modified as described herein to obtain the pentacyclic acid triterpenes of this invention that will exhibit biofilm inhibition.

Finally, another source of the known pentacyclic acid triterpene precursors used to make the pentacyclic acid triterpenes of the invention are commercial sources or vendors. Purified forms of corosolic acid, ursolic acid, oleanolic acid, madecassic acid, asiatic acid, pygenic acid (A, B or C), caulophyllogenin and echinocystic acid may be obtained from a commercial source. For example, ursolic acid and oleanolic acid may be purchased from Sigma-Aldrich Chemical Company (St. Louis, Mo., USA) and corosolic acid, asiatic acid, madecassic acid, pygenic acid (A, B, or C), caulophyllogenin and echinocystic acid may be purchased from Chromadex (Santa Ana, Calif., USA). The compounds obtained from commercial sources may be furthered separated and purified as needed using methods such as column chromatography, high pressure liquid chromatography (HPLC), and/or recrystallization described herein. As will be appreciated by the skilled artisan, further methods of synthetically producing and derivatizing the compounds disclosed herein will be evident from this specification. Additionally, the various isolation, purification, and/or synthetic steps may be performed in an alternate sequence or order to produce the desired compounds.

It is further anticipated that the compounds of the invention can be obtained by direct synthesis. Direct synthesis may include either total synthesis or semi-synthesis. Both synthetic methods for obtaining these compounds are described below.

Publications illustrate the total synthesis of oleanolic acid and other known pentacyclic acid triterpene precursors used to make the pentacyclic acid triterpene compounds of the invention. Total synthesis is thus regarded herein as another means of obtaining the pentacyclic acid triterpene compounds of the invention by direct synthesis. See Corey, E. J. and J. Lee, "Enantioselective Total Synthesis of Oleanolic Acid, Erythrodiol, B-Amyrin, and Other Pentacyclic Triterpenes from a Common Intermediate." *J. Am. Chem. Soc.* 1993, 115; 8873-8874. See Huang, A., et al., "An exceptionally short and simple enantioselective total synthesis of pentacyclic triterpenes of the B-Amyrin family." *J. Am. Chem. Soc.*, 1999, 121; 9999-10003. See Mi, Y., et al., "Total synthesis of (+)-α-onocerin in four steps via four-component coupling and tetracyclization steps." *J. Am. Chem. Soc.* 2002, 124; 11290-11291. It is anticipated that the methods taught by these publications will be generally applicable by one skilled in the art to obtaining known pentacyclic acid triterpene precursors useful for the total synthesis of the pentacyclic acid triterpenes of the invention.

Figure 2:
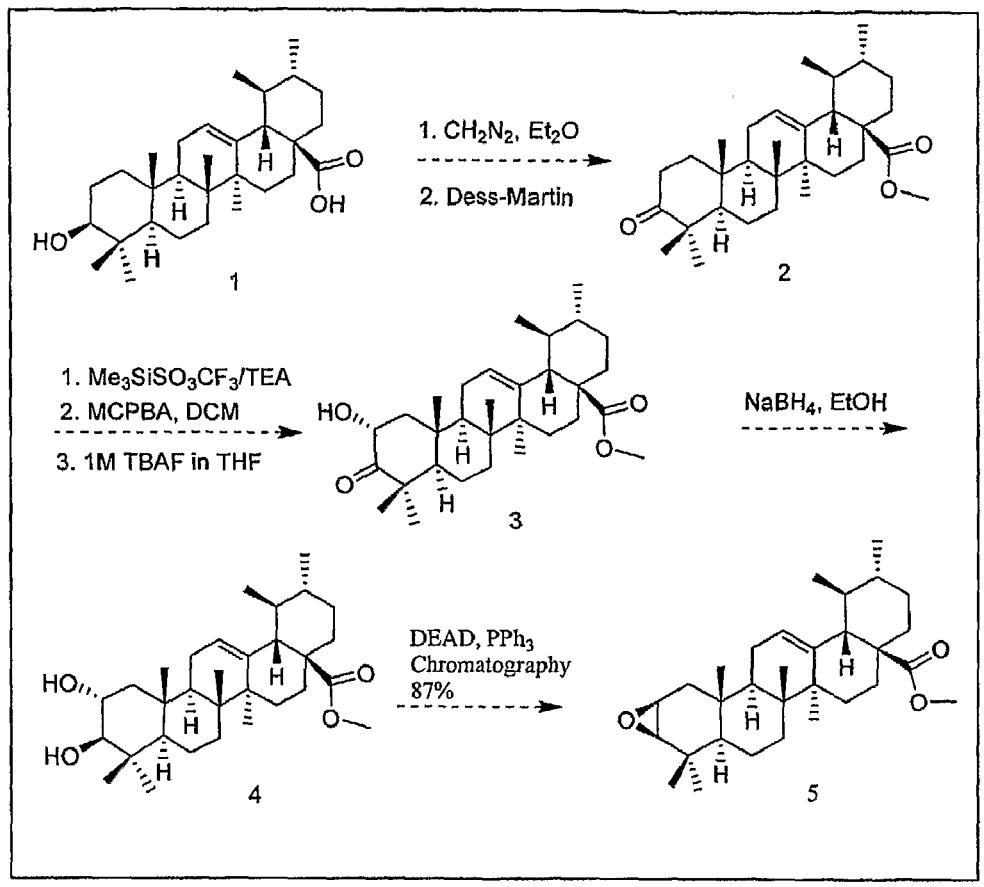
FIG. 2 shows a synthetic scheme for obtaining pentacyclic acid triterpene enone and epoxide intermediate precursors.

Recent publications also illustrate the semi-synthesis of the pentacyclic acid triterpene compounds of the invention. Publications refer to these pentacyclic acid triterpenes as derivatives of ursolic acid and oleanolic acid. These publications also refer to the Carbon number (e.g. C-1 which means Carbon 1) as shown in FIG. 2. This nomenclature will be used within the specification to accurately describe derivatives useful in the practice of this invention. See Farina, C. et al., "Synthesis and anti-ulcer activity of new derivatives of glycyrrhetic oleanolic, and ursolic acids." *Il Farmaco.* 1998, 53, 22-32. See Honda, T.; et al., "Design and synthesis of 2-Cyano-3,12-Dioxoolean-1,9-dien-28-oic acid, a novel and highly active inhibitor of nitric oxide production in mouse macrophages." *Bioorg. Medic. Chem. Lett.,* 1998, 8, 2711-2714. See Konoike, T.; et al., "Synthesis of [2-13C]-Oleanolic acid and [2-13C]-Myricerone." *Tetrahedron.* 1999, 55; 14901-14914. These publications demonstrate semi-synthetic modifications to positions at C-3, C-28, and C-30; and positions C-2, C-3, and C-12; and positions at C-1, C-2, C-3, and the A-ring, respectively, of the compounds of the invention.

In the semi-synthetic preparation of pentacyclic acid compounds of the invention, a typical starting basic chemical compound may be ursolic acid, oleanolic acid, corosolic acid, asiatic acid, or madecassic acid. In designing semi-synthetic strategies to prepare analogs of the basic chemical compound, modifications at certain positions of the scaffold of the basic chemical compound prove to be important for modulating biofilm inhibition, while other modifications at positions can improve the bioavailability of the compound. Improvement of the bioavailability of the compound would expand the therapeutic range of the compounds by reducing certain cellular toxicities in the subject.

As demonstrated by the biofilm inhibition of corosolic acid and ursolic acid, a hydroxyl group of corosolic acid at position C-2 increases the biofilm inhibition. Modification of position C-19 of corosolic acid, as exemplified in tormentic acid slightly reduces the biofilm inhibition against *P. aeruginosa*. However, modification of corosolic acid at positions C-3 (hydroxycinnamoyl) and C-20 (hydroxyl), as exemplified in 3-[4-Hydroxycinnamoyl(cis-)], 20-hydroxy-ursolic acid, increases biofilm inhibition against *P. aeruginosa*. These examples merely demonstrate that the modifications at certain positions of the ursane or oleanane scaffold can modulate the magnitude of biofilm inhibition. The examples are not meant to limit the scope of claimed invention.

Methods for synthesizing various pentacyclic acid triterpene derivatives from precursors such as Ursolic acid, Oleanolic acid, Corosolic acid, Asiatic acid, Maslinic acid and Madecassic acid have also been disclosed. For example, U.S. Pat. No. 5,834,437 (herein incorporated by reference in its entirety) discloses methods of obtaining various derivatives of Asiatic acid and Madecassic acid at the C-2 and C-3 positions of those pentacyclic triterpenes. U.S. Pat. No. 6,369,101 B1 (herein incorporated by reference in its entirety) discloses methods of obtaining various derivatives of betulin at the C-2 and C-3 positions of that pentacyclic triterpene. U.S. Patent Application publication US 2005/0137259 A1 (herein incorporated by reference in its entirety) discloses methods of obtaining acyl derivatives the C-2 and/or C-3 positions of corosolic acid, maslinic acid, ursolic acid and oleanolic acid.

Prodrugs of the pentacyclic acid triterpene compounds described herein are also anticipated. As used herein, the term "prodrug" means a derivative of an active compound (drug) that undergoes a transformation under the conditions of use, such as within the body, to release an active drug. It is understood that this application discloses pentacyclic acid triterpenes that are active compounds and that may be converted to prodrugs by the methods described herein. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

A wide variety of progroups, as well as the resultant promoieties, suitable for masking functional groups in active compounds to yield prodrugs are well-known in the art. For example, a hydroxyl functional group may be masked as a sulfonate, ester or carbonate promoiety, which may be hydrolyzed in vitro to provide the hydroxyl group. An amino functional group may be masked as an amide, imine, phosphinyl, phosphonyl, phosphoryl or sulfenyl promoiety, which may be hydrolyzed in vivo to provide the amino group. A carboxyl group may be masked as an ester (including silyl esters and thioesters), amide or hydrazide promoiety, which may be hydrolyzed in vivo to provide the carboxyl group. Other specific examples of suitable progroups and their respective promoieties will be apparent to those of skill in the art.

In the present invention, a "progroup" means a type of protecting group that, when used to mask a functional group within an active drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH3 comprises the progroup —C(O)CH3.

Specific prodrug embodiments of the compounds of the invention include derivatives of the C-3 hydroxyl group and/or the C-28 carboxyl group of the ursane and oleanane scaffolds that represent pentacyclic acid triterpene compounds of the invention (FIG. 2). One set of prodrugs contemplated by this invention are esters, sulfonates, and carbonates of the C-3 hydroxyl group of a compound of the invention. Another set of prodrugs contemplated by this invention include esters, amides, and hydrazides of the C-28 carboxyl group of a compound of the invention.

Pharmaceutical Compositions

Pharmaceutical compositions comprising a pharmaceutically acceptable carrier and a compound corresponding to the following Structure I

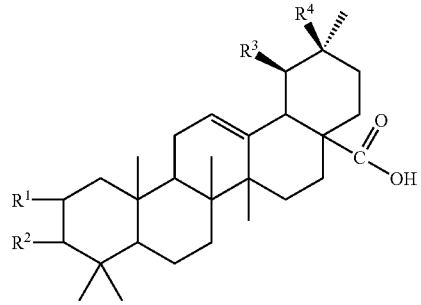

Structure I wherein $R^1$ is selected from the group consisting of hydrogen, hydroxyl, halide, methoxy, acetoxy, —$CH_2$OH, —$CH_2CH_2OH$, —CN, —$C_{1-2}$(halo)alkyl, —$CH_2$Cl, —C(O)H, —C(O)$NH_2$, —SH, $CF_3$, $CCl_3$, and —NAA, wherein each A is independently selected from the group consisting of H and $C_1$-$C_2$ alkyl; $R^2$ is selected from the group consisting of hydroxyl, halide, —CN, —C(O)$NH_2$, —SH, —S(O)$NH_2$, $CF_3$, $CCl_3$, —NYY, wherein each Y is independently selected from H or $C_1$-$C_5$ alkyl, $C_{1-5}$ acyl halides, —$C_{1-5}$(halo)alkyl, $C_{1-5}$ acyl residues, $C_{2-5}$ secondary amides, $(C_{1-5})(C_{1-5})$tertiary amides, $C_{1-5}$ alcohols, $C_{1-5}$ substituted alkyls, $C_{2-5}$ alkenyls, and $C_{2-5}$ substituted alkenyls, —OC(O)—OC($CH_3$)$_3$, —OC(O)—CH═CH-phenyl, —OC(O)—R, wherein R is an unbranched or branched $C_1$-$C_5$ alkyl, and —OC(O)$C_{1-5}R^5R^6$ wherein $R^5$ is an alkylene or alkenylene of up to 5 carbons and $R^6$ is selected from the group consisting of substituted and unsubstituted $C_{5-7}$ aromatics, substituted and unsubstituted $C_{5-7}$ cycloalkyls, and substituted and unsubstituted $C_{5-7}$ heterocycloalkyls, provided that: i) $R^2$ is not hydroxyl when $R^1$ is hydrogen, hydroxyl, methoxy, chloride or —CN; ii) $R^2$ is not chloride or —OC(O)$CH_3$ when $R^1$ is hydrogen; iii) $R^2$ is not —OC(O)—CH═CH-(m-hydroxy, p-methoxy-phenyl) or —OC(O)—CH═CH-(p-hydroxy-phenyl) when $R^1$ is hydroxyl; and iv) $R^2$ is not $C_{1-5}$ substituted alkyl, —$C_{1-5}$(halo)alkyl, or $C_{1-5}$ alcohol when $R^1$ is hydrogen, halide, hydroxyl, methoxy, acetoxy or —SH; and wherein one of $R^3$ and $R^4$ is hydrogen and the other is methyl are contemplated by this invention.

Such compositions containing the novel pentacyclic acid triterpene compound described above may optionally include an antimicrobial agent. It is anticipated that combining the compounds of this invention with an antimicrobial agent and a pharmaceutically acceptable carrier will in some instances yield a superior pharmaceutical composition for either preventing, inhibiting or reducing a biofilm or its formation or for treating, controlling, reducing or preventing a bacterial infection in a subject in need thereof. The antimicrobial agent may be selected from the group consisting of triclosan, metronidazole, tetracyclines, quinolones, plant essential oils, camphor, thymol, carvacrol, menthol, eucalyptol, methyl salicylate, tobramycin, clindamycin, ciprofloxacin, rifampin, oxfloxacin, macrolides, penicillins, cephalosporins, amoxicillin/clavulanate, quinupristin/dalfopristin, amoxicillin/sulbactum, fluoroquinolones, ketolides, and aminoglycosides. For dentifrices, it is envisioned that the antimicrobial agent is selected from a preferred group consisting of consisting of triclosan, metronidazole, tetracyclines, quinolones, plant essential oils, camphor, thymol, carvacrol, menthol, eucalyptol, and methyl salicylate. For other compositions useful as oral, topical, parenterally injected, percutaneous, rectal, intranasal or inhaled dose forms it is envisioned that the antimicrobial agent is an antibiotic selected from the group consisting of tobramycin, clindamycin, ciprofloxacin, tetracyclines, rifampin, triclosan, oxfloxacin, macrolides, penicillins, cephalosporins, amoxicillin/clavulanate, quinupristin/dalfopristin, amoxicillin/sulbactum, metronidazole, fluoroquinolones, quinolones, ketolides, and aminoglycosides.

Still other compositions comprising other pentacyclic acid triterpene compounds, a pharmaceutically acceptable carrier and an antimicrobial agent are also contemplated. The other pentacyclic acid triterpenes used in the compositions containing antimicrobial agents are of the preceeding chemical Structure I wherein $R^1$ is selected from the group consisting of hydrogen, hydroxyl, halide, methoxy, acetoxy, —$CH_2OH$, —$CH_2$ $CH_2OH$, —CN, —$C_{1-2}$(halo)alkyl, —$CH_2$ Cl, —C(O)H, —C(O)$NH_2$, —SH, $CF_3$, $CCl_3$, and —NAA, wherein each A is independently selected from the group consisting of H and $C_1$-$C_2$ alkyl; $R^2$ is selected from the group consisting of hydroxyl, halide, —CN, —C(O)$NH_2$, —SH, —S(O)$NH_2$, $CF_3$, $CCl_3$, —NYY, wherein each Y is independently selected from H or $C_1$-$C_5$ alkyl, $C_{1-5}$ acyl halides, —$C_{1-5}$(halo)alkyl, $C_{1-5}$ acyl residues, $C_{2-5}$ secondary amides, ($C_{1-5}$)($C_{1-5}$)tertiary amides, $C_{1-5}$ alcohols, $C_{1-5}$ substituted alkyls, $C_{2-5}$ alkenyls, and $C_{2-5}$ substituted alkenyls, —OC(O)—OC(CH$_3$)$_3$, —OC(O)—CH=CH-phenyl, —OC(O)—R, wherein R is an unbranched or branched $C_1$-$C_5$ alkyl, and —OC(O) $C_{1-5}R^5R^6$ wherein $R^5$ is an alkylene or alkenylene of up to 5 carbons and $R^6$ is selected from the group consisting of substituted and unsubstituted $C_{5-7}$ aromatics, substituted and unsubstituted $C_{5-7}$ cycloalkyls, and substituted and unsubstituted $C_{5-7}$ heterocycloalkyls; provided that: i) $R^2$ is not hydroxyl when $R^1$ is hydrogen or hydroxyl; ii) $R^2$ is not —OC(O)$CH_3$ when $R^3$ is hydrogen; and iii) $R^1$ is not —OC(O)—CH=CH-(m-hydroxy, p-methoxy-phenyl) or —OC(O)—CH=CH-(p-hydroxy-phenyl) when $R^1$ is hydroxyl; one of $R^3$ and $R^4$ is hydrogen and the other is methyl. Salts, hydrates, solvates, prodrugs and N-oxides of the pentacyclic acid triterpene compounds are also contemplated by the present invention. As demonstrated herein, such compositions are useful in controlling bacterial infections and/or biofilm formation in a variety of subjects including animals such as mammals and human patients.

In one embodiment of this invention, a compound selected from the group consisting of a pentacyclic acid triterpene compound or a salt, hydrate, solvate, prodrug or N-oxide thereof is present at more than 1% by weight. In certain embodiments, the pentacyclic acid triterpene compound of the invention comprises 2% to about 60% by weight of the composition. In particular, it is anticipated that oral dose forms of the composition may comprise over 30% by weight of the pentacyclic acid triterpene compound. In certain preferred embodiments useful as topical treatments or dentifrices, the pentacyclic acid triterpene compound makes up about 2% to about 5% by weight of the composition. In the most preferred embodiments useful as topical treatments or dentifrices, the pentacyclic acid triterpene compound makes up about 2% by weight of the composition.

In other embodiments of the invention, the composition comprises an antimicrobial agent, one and only one pentacyclic acid triterpene compound or a salt, hydrate, solvate, prodrug or N-oxide thereof, and a pharmaceutically acceptable carrier, and wherein the compound is present in a concentration of at least about 0.1% by weight, based on the total weight of the composition. While not being limited by theory, it is believed that in certain instances compositions that provide one and only one pentacyclic acid triterpene compound may provide improved control of biofilms or bacterial infections in subjects in need thereof. In particular, it is anticipated that oral dose forms of the composition may comprise over 30% by weight of one and only one pentacyclic acid triterpene compound. In certain preferred embodiments useful as topical treatments or dentifrices, one and only one pentacyclic acid triterpene compound makes up about 2% to about 5% by weight of the composition. In the most preferred embodiments useful as topical treatments or dentifrices, one and only one pentacyclic acid triterpene compound makes up about 2% by weight of the composition.

Various pharmaceutical compositions that may be used in the present invention, including the compounds of the invention and the specific examples described herein, further including pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a patient, is capable of providing (directly or indirectly) a compound used in this invention. The compositions useful in the present invention may, optionally, be converted to their therapeutically-active non-toxic acid salt forms by treatment with appropriate acids. Such acids include inorganic acids, e.g., hydrochloric and hydrobromic acids, sulfuric acid, nitric acid, phosphoric acid and like acids; or organic acids, such as acetic, propanoic, hydroxyacetic, 2-hydroxypropanoic, 2-oxo-propanoic, ethanedioic, propanedioic and like acids. Of course, the salt forms may be converted into the free base form by treatment with alkali. The pharmaceutically-acceptable acid salts of the present invention also comprise the solvates that the compositions of the present invention may form, which, of course, are included within the scope of the present invention. Non-limiting examples of such solvates are hydrates, alcoholates and the like.

Such pharmacologic compositions may be formulated in various ways known in the art for administration purposes. To prepare the pharmaceutical compositions of the present invention, an effective amount of the particular compound, in base or acid salt form, as the active ingredient is combined with one or more pharmaceutically-acceptable carriers and delivery vehicles. Numerous pharmaceutically acceptable carriers and delivery vehicles exist that are readily accessible and well-known in the art, which may be employed to generate the preparation desired (i.e. that permit administration of the pharmaceutical composition orally, topically, rectally, percutaneously, by parenteral injection, intranasally or by inhalation). Representative examples of pharmaceutically acceptable carriers and delivery vehicles include aluminum stearate, lecithin, serum proteins, such as human serum albumin; buffer substances such as the various phosphates, glycine, sorbic acid, potassium sorbate, partial glyceride mixtures of saturated vegetable fatty acids; water, salts or electrolytes, such as protamine sulfate, disodium hydrogen phosphate, potassium hydrogen phosphate, sodium chloride, and zinc salts; colloidal silica, magnesium trisilicate, polyvinyl pyrrolidone, cellulose-based substances, polyethylene glycol, sodium carboxymethylcellulose, polyarylates, waxes, polyethylene, polyoxypropylene-block polymers, polyethylene glycol and wool fat, and the like.

The pharmacologic compositions described herein may further be prepared in unitary dosage form suitable for administration orally, percutaneously, by parenteral injection (including subcutaneous, intramuscular, intravenous and intradermal), topically, intranasally, by inhalation, or for application to a medical device, such as an implant, catheter, or other device. In preparing the compositions that permit administration of an oral dosage, for example, any of the pharmaceutically acceptable carriers known in the art may be used, such as water, glycols, oils, alcohols and the like in the case of carriers that permit oral delivery of liquid preparations such as suspensions, syrups, elixirs and solutions. When solid pharmaceutically acceptable carriers are desired that permit oral or rectal administration, starches, sugars, kaolin, lubricants, binders, cellulose and its derivatives, and disintegrating agents and the like may be used to prepare, for example, powders, pills, capsules and tablets.

For pharmaceutically acceptable carriers that permit parenteral administration, the pharmaceutically acceptable carriers often comprise sterile water, which may be supplemented with various solutes to, for example, increase solubility. Injectable solutions may be prepared in which the pharmaceutically acceptable carrier comprises saline solution, glucose solution, or a mixture thereof, which may include certain well-known anti-oxidants, buffers, bacteriostats, and other solutes that render the formulation isotonic with the blood of the intended patient.

For pharmaceutically acceptable carriers that permit intranasal administration, the pharmaceutically acceptable carriers often comprise poly acrylic acids such as Carbopol® 940, a hydrogenated castor oil such as Cremophor® RH40, glycerol, vinylpyrrolidones such as PVP-K90® or PVP K30®, polyethylene glycols such as PEG 1450®, benzyl alcohol, Edetate sodium, hydroxycellulose, potassium chloride, potassium phosphate, and sodium phosphate. Compositions used for intranasal administration also commonly include benzalkonium chloride as an anti-microbial preservative.

For pharmaceutically acceptable carriers that permit administration by inhalation, the pharmaceutically acceptable carriers often comprise solvent/carrier/water mixtures that are easily dispersed and inhaled via a nebulizer or inhaler. For example, a mixture of ethanol/propylene glycol/water in the ratio of about 85:10:5 (parts ethanol: parts propylene glycol: parts water) can be used to administer the compounds and compositions of the invention via inhalation.

For pharmaceutically acceptable carriers that permit percutaneous administration, the pharmaceutically acceptable carrier may, optionally, comprise a penetration enhancing agent and/or a suitable wetting agent.

Dosage forms that permit topical or transdermal administration of a compound of this invention include ointments, pastes, creams, lotions, gels, powders, solutions, sprays, inhalants or patches. The active compound or compounds is/are mixed under sterile conditions with a pharmaceutically acceptable carrier and optionally one or more preservatives and/or buffers. In the context of certain embodiments of this invention, the active compound is a pentacyclic acid triterpene. In the context of other embodiments of this invention, the pentacyclic acid triterpene is combined in the composition with another active compound that is an antimicrobial agent or antibiotic.

The ointments, pastes, creams and gels may contain, in addition to an active compound or compounds according to the present invention, pharmaceutically acceptable carriers that permit topical or transdermal administration such as animal and vegetable fats, oils, waxes, paraffins, starch, tragacanth, cellulose derivatives, polyethylene glycols, silicones, bentonites, silicic acid, talc and zinc oxide, or mixtures thereof.

In some cases, the pH of the pharmaceutical formulations contemplated herein may be adjusted with acceptable acids, bases or buffers to enhance the stability of one or more of the active compounds present or their delivery forms. In the context of certain embodiments of this invention, the active compound is a pentacyclic acid triterpene. In the context of other embodiments of this invention, the pentacyclic acid triterpene is combined in the composition with another active compound that is an antimicrobial agent or antibiotic.

Still further, in order to prolong the anti-bacterial effect of a compound disclosed herein, it may be desirable to slow the absorption of the compound from subcutaneous or intramuscular injection. This may be accomplished using a liquid suspension of crystalline or amorphous material with poor water solubility. The rate of absorption of the compound then depends upon its rate of dissolution, which, in turn, may depend upon crystal size and crystalline form. Alternatively, delayed absorption of a parenterally administered drug form may be accomplished by dissolving or suspending the compound in an oil vehicle.

Injectable depot forms are made, e.g., by forming microencapsule matrices of one or more compounds of the present invention in biodegradable polymers such as polylactide-polyglycolide. Depending upon the ratio of active(s) to polymer and the nature of the particular polymer employed, the rate at which such active(s) is released may be controlled. Examples of other biodegradable polymers include poly (orthoesters) and poly(anhydrides). Depot injectable formulations are also prepared by entrapping the compound in liposomes or microemulsions that are compatible with body tissues.

The pharmaceutical composition may also be a dentifrice. In the present invention, "dentifrice" is understood to broadly include compositions suitable for administering to the oral cavity, especially, for example, to the gingival/mucosal tissue or to the teeth. Thus, the dentifrice may include toothpastes, toothpowders, liquid dentifrices, mouth detergents, mouthwashes, troches, chewing gums, dental or gingival massage creams, dental strips, dental gels, and gargle tablets.

When the pharmaceutical composition of this invention is a dentifrice such as tooth paste, a tooth or gum adherence promoting substance selected from the group consisting of copolymers of methyl vinyl ether and maleic anhydride, copolymers of vinyl pyrrolidone and vinyl acetate, and cyclodextrins may also be included in the composition. Copolymers of methyl vinyl ether and maleic anhydride useful in this invention may have molecular weights ranging from 200,000 to 2,000,000 kD and may be free acids, mixed sodium and calcium salts, or half ester derivatives. Representative commercial sources of the copolymers of methyl vinyl ether and maleic anhydride include GANTREZ® AN(CAS # 9011-16-9) GANTREZ® S (CAS # 25153-40-69) GANTREZ® MS (CAS# 62386-95-2) GANTREZ® ES (CAS# 25087-06-3 or CAS# 25119-68-0) and can be obtained from International Specialty Products Wayne, N.J. Copolymers of vinyl pyrrolidone and vinyl acetate useful in the invention typically have a molecule weight of approximately 27,000 kD and are water soluble. Representative commercial sources of the copolymers of vinyl pyrrolidone and vinyl acetate PLASDONE® S-630 and can be obtained from International Specialty Products Wayne, N.J. Cyclodextrins useful in the invention are cyclic oligosaccharides composed of either 6, 7 or 8 glucose units (a-, b- and g-cyclodextrin, respectively). Representative commercial sources of the cyclodextrins useful in this invention include CAVAMAX® W6 Pharma, CAVAMAX®W7 Pharma and CAVAMAXW8 Pharma (a-, b- and g-cyclodextrin, respectively) and can be obtained from International Specialty Products Wayne, N.J.

When the composition of this invention is a dentifrice, an antimicrobial agent is selected from the group consisting of triclosan, metronidazole, tetracyclines, quinolones, plant essential oils, camphor, thymol, carvacrol, menthol, eucalyptol, and methyl salicylate may also be included. Pharmaceutically acceptable carriers that permit administration of the pentacyclic acid triterpene compounds of this application as dentifrices include sorbitol, glycerin, silica, sodium lauryl sulfate and *Xanthum* gum. The dentifrices of this invention may also include sodium fluoride.

Methods of Inhibiting Biofilm Formation

Various methods for inhibiting biofilm formation both in vivo and in vitro are contemplated by this invention. The pentacyclic acid triterpenes used in the methods for inhibiting biofilm formation are of the preceeding chemical Structure I wherein $R^1$ is selected from the group consisting of hydrogen, hydroxyl, halide, methoxy, acetoxy, —$CH_2$ OH, —$CH_2$ $CH_2OH$, —CN, —$C_{1-2}$(halo)alkyl, —$CH_2$ Cl, —C(O)H, —C(O)$NH_2$, —SH, $CF_3$, $CCl_3$, and —NAA, wherein each A is independently selected from the group consisting of H and $C_1$-$C_2$ alkyl; $R^2$ is selected from the group consisting of hydroxyl, halide, —CN, —C(O)$NH_2$, —SH, —S(O)$NH_2$, $CF_3$, $CCl_3$, —NYY, wherein each Y is independently selected from H or $C_1$-$C_5$ alkyl, $C_{1-5}$ acyl halides, —$C_{1-5}$(halo)alkyl, $C_{1-5}$ acyl residues, $C_{2-5}$ secondary amides, $(C_{1-5})(C_{1-5})$tertiary amides, $C_{1-5}$ alcohols, $C_{1-5}$ substituted alkyls, $C_{2-5}$ alkenyls, and $C_{2-5}$ substituted alkenyls, —OC(O)—OC($CH_3$)$_3$, —OC(O)—CH=CH-phenyl, —OC(O)—R, wherein R is an unbranched or branched $C_1$-$C_5$ alkyl, and —OC(O)$C_{1-5}R^5R^6$ wherein $R^5$ is an alkylene or alkenylene of up to 5 carbons and $R^6$ is selected from the group consisting of substituted and unsubstituted $C_{5-7}$ aromatics, substituted and unsubstituted $C_{5-7}$ cycloalkyls, and substituted and unsubstituted $C_{5-7}$ heterocycloalkyls; provided that: i) $R^2$ is not hydroxyl when $R^1$ is hydrogen or hydroxyl; ii) $R^2$ is not —OC(O)$CH_3$ when $R^1$ is hydrogen; and iii) $R^2$ is not —OC(O)—CH=CH-(m-hydroxy, p-methoxy-phenyl) or —OC(O)—CH=CH-(p-hydroxy-phenyl) when $R^1$ is hydroxyl; one of $R^3$ and $R^4$ is hydrogen and the other is methyl. Salts, hydrates, solvates, prodrugs and N-oxides of the pentacyclic acid triterpene compounds are also contemplated by the present invention. In these methods, either a composition containing a pentacyclic acid triterpene compound or the pentacyclic acid triterpene compound itself may be provided to the system before, during, or after a biofilm has formed. As demonstrated herein, such compounds and compositions are useful in controlling bacterial infections and/or biofilm formation in a variety of subjects including animals such as mammals and human patients.

In the methods for inhibiting biofilms, an antimicrobial agent, antibiotic or biocide may be incorporated into the system together with the compound in a composition or administered separately. In the present invention, any antimicrobial agent, antibiotic or biocide may be used. Representative examples of biocides that may be used in the present invention, include isothiazolone, derivatives thereof, compounds having a isothiazolone functions, 3-isothiazolone compound, 5-chloro-2-methyl-3-isothiazolone, 1-methyl-3,5,7-triaza-1-azoniatricyclo(3.3.1.1)deoane chloride, 4,5-dichloro-2-octyl-3 isothiazolone, 2-bromo-2-nitropropanediol, 5-bromo-5-nitro dioxane, thiocyanomethylthiobenzothiazole, 4,5-dichloro-2-octyl-3-isothiazolone and 2-noctyl-3-isothiazolone, tetrachloroisophalonitrile, 1,2-benzisothiazolin-3-one, 2-methyl-4,5-trimethylene-4-isothiazolin-3-one, 5-chloro-2-methyl-4isothiazolin-3-one, 2-methyl-4-isothiazolin-3-one, 4-(2-nitrobutyl)morpholine, beta-nitrostyrene ("NS"), beta-bromobeta-nitrostyrene ("BNS"), methylehloro/isothiazolone ("IZN"), methylenebisthiocyanate ("MBT"), 2,2dibrortmo-3-nitrilopropionamide ("DBNPA"), 2-bromo-2-bromomethylglutaronitrile ("BBMGN"), alkyldimethyl-benzylammonium chloride ("ADBAC"), and betatiitrovinyl-furan ("NVF"), 2-methyl-3-isothiazolone, methylene bisthiocyanate, ptolyldiiodotnethylsulfone, 2-methylthio-4-tertbutylamino-6-cyclopropylamino-s-tiiazine,N,N-dimethyl-N'phenyl(N'fluorodiehloromethylthio)sulfamide, sulfamides, N-(cyclo)alkyl-isothiazolone, benzisothiazolin-3-one, etc. and their mixtures.

Other examples of biocides that may be combined with one or more of the biocides listed above include bicyclic oxazolidoines and their mixtures, amine-based bactericide, polyacrolein copolymer, 4,4-dimethyloxazolidine, 2((hydroxymethyl)-amino)ethanol, mixtures of 1,2-benzisothiazolone-3-one with one or more amines, tetrahydro-3,5-dimethyl-2H-1,3,5-thiadiazitie-2-thione. 1,2-benzisothiazolin-3-one, tetrachloroisophthalonitrile, N-cyclopropyl-N-(1,1-dimethylethyl)-6-(methylthio)-1,3; 5-triazine-2,4-diamine, mixtures of N-cyclopropyl-N-(1,1-dimethylethyl)-6-(methylthio)-1,3,5-triazine-2,4-diamine with tetrachloroisophthalonitrile, mixtures of tetrachloroisophthalonitrile with 3-iodo-2-propynylbutyl carbamate, N-(trichloromethylthio)-phthalimide, 3-iodo-2-propynylbutyl carbamate, tetrachloroisophthalonitrile, and their mixtures.

Representative examples of antimicrobial agents useful in methods for inhibiting biofilms include triclosan, metronidazole, tetracyclines, quinolones, plant essential oils, camphor, thymol, carvacrol, menthol, eucalyptol, methyl salicylate, tobramycin, clindamycin, ciprofloxacin, rifampin, oxfloxacin, macrolides, penicillins, cephalosporins, amoxicillin/clavulanate, quinupristin/dalfopristin, amoxicillin/sulbactum, fluoroquinolones, ketolides, and aminoglycosides.

Representative examples of antibiotics that may be useful in the practice of the methods of this invention include tobramycin, clindamycin, ciprofloxacin, tetracyclines, rifampin, triclosan, oxfloxacin, macrolides, penicillins, cephalosporins, amoxicillin/clavulanate, quinupristin/dalfopristin, amoxicillin/sulbactum, metronidazole, fluoroquinolones, quinolones, ketolides, or aminoglycosides.

In this application of this method, the compound may be applied to the surface of a substrate. The substrate may be made from any material to which the compound or a composition containing the compound may be applied. Representative examples of the kinds of materials from which the substrate may be made, include porous materials, soft materials, hard materials, semi-hard materials, regenerating materials, and non-regenerating materials. Preferably, the substrate is made from an inert material selected from the group consisting of a polymer, a metal, an alloy, and combinations thereof. In an alternatively preferred embodiment, the substrate is a biological structure, such as for example, regenerating proteins of mammalian cellular membranes, dental enamel, gum, tongue, and biological polymers.

Preferably, the substrate is a surface of a device that is susceptible to biofilm formation. Examples of suitable substrate surfaces according to the present invention include vessel hulls, automobile surfaces, air plane surfaces, membranes, filters, industrial machinery, microtiter plates, continuous flow chambers, bioreactors, fermentors, chemostats and industrial equipment. Bioreactors can be purchased from Biosurface Technologies Corporation (Bozeman, Mont., USA) and are preferably a drip flow reactor and more preferably a Centers for Disease Control reactor (CDC reactor) or a Rotating Disk Reactor (RDR).

The substrate may also be a medical device. Examples of medical devices included within the present invention include any device that is capable of being implanted temporarily or permanently into a mammalian organism, such as a human. Representative examples of medical devices that may be used according to the present invention include: central venous catheters, urinary catheters, endotracheal tubes, mechanical heart valves, pacemakers, vascular grafts, stents, and prosthetic joints.

Methods of Preventing or Inhibiting Bacterial Infections in a Subject

The methods of the present invention include using the compositions described herein to prevent or inhibit bacterial infections. In the case of medical applications where the subject is a human, the methods of the present invention comprise the steps of providing an effective amount of at least one composition described herein to a patient. In the case of veterinary applications, the subject is an animal. Such compositions and methods are used to treat and/or prevent bacterial-related health afflictions either alone or in combination with antimicrobial agent. In the methods for preventing or inhibiting bacterial infections, an antimicrobial agent, antibiotic or biocide may be incorporated into the system together with the pentacyclic acid triterpene compound in a composition or administered separately. Representative examples of antimicrobial agents that may be useful in the practice of this invention include triclosan, metronidazole, tetracyclines, quinolones, plant essential oils, camphor, thymol, carvacrol, menthol, eucalyptol, methyl salicylate, tobramycin, clindamycin, ciprofloxacin, rifampin, oxfloxacin, macrolides, penicillins, cephalosporins, amoxicillin/clavulanate, quinupristin/dalfopristin, amoxicillin/sulbactum, fluoroquinolones, ketolides, and aminoglycosides. The antimicrobial agent may be an antibiotic. Representative examples of antibiotics that may be useful in the practice of this invention include tobramycin, clindamycin, ciprofloxacin, tetracyclines, rifampin, triclosan, oxfloxacin, macrolides, penicillins, cephalosporins, amoxicillin/clavulanate, quinupristin/dalfopristin, amoxicillin/sulbactum, metronidazole, fluoroquinolones, quinolones, ketolides, or aminoglycosides. While the following description makes reference to specific methods and uses of the disclosed compositions for human applications, it should be appreciated that such compositions and methods may be equally useful in veterinary applications wherein the subject is an animal.

Asiatic acid and madecassic acid are shown herein to prevent, reduce and/or inhibit biofilm formation by *P. aeruginosa* and *E. coli* in the absence of any bacterial growth inhibition. The examples shown herein further demonstrate that asiatic acid and madecassic acid can be used to treat chronic infections involving biofilms, including urinary tract infection, gastritis, lung infection, ear infection, cystitis, pyelonephritis, arterial damage, leprosy, tuberculosis, benign prostatic hyperplasia, prostatitis, osteomyelitis, bloodstream infection, cirrhosis, skin infection, acne, rosacea, open wound infection, chronic wound infection, and sinus infection. Other compounds in *Centella asiatica* extract unnecessarily dilute the concentration of asiatic acid or madecassic acid and reduce their efficiency. We demonstrate that asiatic acid and madecassic acid are biofilm inhibitors and can be used to control, prevent, or treat bacterial infections involving biofilms like urinary tract infections, cystitis, pyelonephritis, and ear infections with or without antibiotics. The use of asiatic acid or madecassic acid as anti-infectives was not previously contemplated as these compounds do not display direct anti-bacterial activity when assayed in bacterial growth inhibition studies.

According to the methods of preventing or inhibiting bacterial infections of animals disclosed herein, the bacterial infections are treated or prevented in a patient by administering or providing an effective amount of a pentacyclic acid triterpene compound or composition disclosed herein, in such amounts and for such time as is necessary to achieve the desired result. The pentacyclic acid triterpenes used in the methods for inhibiting or preventing bacterial infections are of the preceeding chemical Structure I wherein $R^1$ is selected from the group consisting of hydrogen, hydroxyl, halide, methoxy, acetoxy, —$CH_2$ OH, —$CH_2$ $CH_2$OH, —CN, —$C_{1-2}$(halo)alkyl, —$CH_2$ Cl, —C(O)H, —C(O)$NH_2$, —SH, $CF_3$, $CCl_3$, and —NAA, wherein each A is independently selected from the group consisting of H and $C_1$-$C_2$ alkyl; $R^2$ is selected from the group consisting of hydroxyl, halide, —CN, —C(O)$NH_2$, —SH, —S(O)$NH_2$, $CF_3$, $CCl_3$, —NYY, wherein each Y is independently selected from H or $C_1$-$C_5$ alkyl, $C_{1-5}$ acyl halides, —$C_{1-5}$(halo)alkyl, $C_{1-5}$ acyl residues, $C_{2-5}$ secondary amides, ($C_{1-5}$)($C_{1-5}$)tertiary amides, $C_{1-5}$ alcohols, $C_{1-5}$ substituted alkyls, $C_{2-5}$ alkenyls, and $C_{2-5}$ substituted alkenyls, —OC(O)—OC($CH_3$)$_3$, —OC(O)—CH=CH-phenyl, —OC(O)—R, wherein R is an unbranched or branched $C_1$-$C_5$ alkyl, and —OC(O)$C_{1-5}R^5R^6$ wherein $R^5$ is an alkylene or alkenylene of up to 5 carbons and $R^6$ is selected from the group consisting of substituted and unsubstituted $C_{5-7}$ aromatics, substituted and unsubstituted $C_{5-7}$ cycloalkyls, and substituted and unsubstituted $C_{5-7}$ heterocycloalkyls; provided that: i) $R^2$ is not hydroxyl when $R^1$ is hydrogen or hydroxyl; ii) $R^2$ is not —OC(O)$CH_3$ when $R^1$ is hydrogen; and iii) $R^2$ is not —OC(O)—CH=CH-(m-hydroxy, p-methoxy-phenyl) or —OC(O)—CH=CH-(p-hydroxy-phenyl) when $R^1$ is hydroxyl; one of $R^3$ and $R^4$ is hydrogen and the other is methyl. Salts, hydrates, solvates, prodrugs and N-oxides of the pentacyclic acid triterpene compounds are also contemplated by the present invention. In these methods, the composition containing a pentacyclic acid triterpene compound further comprises a pharmaceutically acceptable carrier.

The specific therapeutically effective dose level for any particular patient may depend upon a variety of factors, including the specific biofilm (and, preferably, taking into account the source of such biofilm) being treated or inhibited; the amount of existing biofilm to be treated, if any, within a given patient; the activity of the specific compound employed; the specific pharmacologic formulation employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts. Furthermore, it may be appropriate to administer the required dose more than once in a twenty-four hour period, such as for example in two, three, four or more sub-doses at appropriate intervals throughout the day.

By way of example only, the total daily dose of one or more of the biofilm inhibitors disclosed herein may be provided to a patient in single or in divided doses, which may be in amounts from 0.01 to 50 mg/kg body weight or, more typically, from 0-1 to 25 mg/kg body weight. Single dose compositions may contain such amounts or submultiples thereof to make up the daily dose. More preferably, treatment regimens according to the present invention may comprise administering to a patient about 10 mg to about 1000 mg of the biofilm inhibitor(s) disclosed herein, per day in single or multiple doses.

More than 1 million patients develop urinary tract infections from catheters. The present invention may be utilized to inhibit biofilms in or on urinary catheters and, further, to reduce or prevent bacterial colonization thereon. The compounds and compositions of the present invention also may be used to inhibit biofilms formed by *E. coli* that reside intracellularly in bladder cells, which resist conventional antibiotics and evade host immune systems. Not wishing to be bound by a particular theory, it is believed that by preventing or disrupting the attachment of *E. coli* to uroplakin or the proteins of the tight junctions of umbrella cells of the bladder, the compounds and compositions of the present invention may prevent, reduce, or control the re-occurrence of such urinary tract infections.

The compounds and compositions of the present invention also may be used to treat, i.e., prevent and/or reduce the risk of atherosclerosis and kidney stones. Again, not wishing to be bound by a particular theory, it is believed that bacterial colonization may cause atherosclerosis and the formation of kidney stones. For example, bacterial colonization has been identified in calcified human aneurysms, carotid plaques, femoral arterial plaques, and cardiac valves. Arterial calcification appears to resemble infectious lesion formation in models of atherosclerosis. Moreover, it is believed that a toxin produced by Cag-A positive *Helicobacter pylori* colonization of the stomach leads to tissue inflammation and lesions in arterial walls resulting in atherosclerosis. Accordingly, administering to a patient in need thereof one or more compounds of the present invention (or a composition containing one or more compounds of the present invention) may reduce the risk of, or treat atherosclerosis and kidney stones.

The compounds and compositions of the present invention may be used to treat cystic fibrosis. The principal organism found in the lungs of cystic fibrosis patients is *Pseudomonas aeroginosa*, existing within a biofilm. Thus, the compounds and compositions of the present invention may be used to prevent, inhibit or reduce the formation of biofilms in the lungs of such cystic fibrosis patients.

Diseased tissue, including certain tumors, are more susceptible to bacterial colonization. Based on this observation, clostridia spores and attenuated *Salmonella typhimurium* have been used to deliver therapeutic proteins to tumors. These bacteria selectively colonize tumors versus normal tissue. Accordingly, further embodiments of the invention include administering the compounds and compositions of the present invention to diseased tissues to reduce, treat or eradicate the biofilms within the diseased tissue, including tumors. Again, not wishing to be bound by a particular theory, it is believed that the eradication of biofilms and bacteria from such diseased tissue would enable the mammalian immune system, and/or other pharmaceutical compositions, to further treat the diseased tissue after bacterial colonization has been removed or reduced.

The compounds and compositions of the present invention may also be administered to patients experiencing gastritis. While not wishing to be bound by a particular theory, it is believed that the compounds and compositions of the present invention may be used to prevent the attachment of *Helicobactor pylori* to gastric epithelial cells, which retards the bacteria's ability to invade these cells and/or inhibits or reduces subsequent virulence factors that result in inflammation. By preventing *H. pylori* attachment to gastric epithelial cells, such biofilm inhibitors may further mitigate arterial damage, which may otherwise lead to an increased risk of stroke.

Notwithstanding the examples set forth above, those skilled in the art should appreciate that the compounds and compositions of the present invention may generally be employed to reduce, cure, and/or prevent other acute or chronic microbial infections caused by, e.g., bacterial colonization not expressly described herein. Such compounds and compositions may be used to control, for example, microorganisms that colonize extracellularly or intracellularly. By way of further illustration only, such compounds and compositions may be used to reduce, cure and/or prevent: arterial damage, gastritis, urinary tract infections, otitis media, leprosy, tuberculosis, benign prostratic hyperplasia, chronic prostratitis, chronic infections of humans with cystic fibrosis, osteomyelitis, bloodstream infections, skin infections, open wound infections, and any acute or chronic infection that involves a biofilm.

As previously stated in this specification, conserved mechanisms of bacterial pathogenesis among Gram-positive and Gram-negative bacteria involve cellular invasion. This process enables the bacteria to evade an immune response to increase their population. Therefore, compounds that reduce bacterial invasion would significantly assist the immune system in the eradication of these pathogens. A reduction in bacterial invasion into cells would also help increase the effectiveness of conventional antibiotics. Niels Moller-Frimodt described that antibiotics used to treat urinary tract infections efficiently kill bacteria in the urine, but are insufficient to kill bacteria after they invade the bladder or tissues (Moller-Frimodt, N. Int. J. of Antimicrob Agents, 2002, 19; 546-553). This farther supports the benefits of compounds that reduce the invasion of bacteria into cells.

Preventing or Inhibiting Bacterial Infections of Plants

Finally, bacterial infections may also be prevented or inhibited by the compositions containing pentacyclic acid triterpene compounds disclosed herein when the subject is a plant. Thus, the compound or a composition containing the pentacyclic acid triterpene compound may be administered to a plant, such as a surface of a plant to prevent or inhibit the formation of a biofilm on the plant.

The pentacyclic acid triterpenes used in the methods for inhibiting or preventing bacterial infections in plants are of the preceeding chemical Structure I wherein $R^1$ is selected from the group consisting of hydrogen, hydroxyl, halide, methoxy, acetoxy, $-CH_2OH$, $-CH_2CH_2OH$, $-CN$, $-C_{1-2}$(halo)alkyl, $-CH_2Cl$, $-C(O)H$, $-C(O)NH_2$, $-SH$, $CF_3$, $CCl_3$, and $-NAA$, wherein each A is independently selected from the group consisting of H and $C_1$-$C_2$ alkyl; $R^2$ is selected from the group consisting of hydroxyl, halide, $-CN$, $-C(O)NH_2$, $-SH$, $-S(O)NH_2$, $CF_3$, $CCl_3$, $-NYY$, wherein each Y is independently selected from H or $C_1$-$C_5$ alkyl, $C_{1-5}$ acyl halides, $-C_{1-5}$(halo)alkyl, $C_{1-5}$ acyl residues, $C_{2-5}$ secondary amides, $(C_{1-5})(C_{1-5})$tertiary amides, $C_{1-5}$ alcohols, $C_{1-5}$ substituted alkyls, $C_{2-5}$ alkenyls, and $C_{2-5}$ substituted alkenyls, $-OC(O)-OC(CH_3)_3$, $-OC(O)-CH=CH$-phenyl, $-OC(O)-R$, wherein R is an unbranched or branched $C_1$-$C_5$ alkyl, and $-OC(O)C_{1-5}R^5R^6$ wherein $R^5$ is an alkylene or alkenylene of up to 5 carbons and $R^6$ is selected from the group consisting of substituted and unsubstituted $C_{5-7}$ aromatics, substituted and unsubstituted $C_{5-7}$ cycloalkyls, and substituted and unsubstituted $C_{5-7}$ heterocloalkyls; provided that: i) $R^2$ is not hydroxyl when $R^1$ is hydrogen or hydroxyl; ii) $R^2$ is not $-OC(O)CH_3$ when $R^1$ is hydrogen; and iii) $R^2$ is not $-OC(O)-CH=CH$-(m-hydroxy, p-methoxy-phenyl) or $-OC(O)-CH=CH$-p-hydroxy-phenyl) when $R^1$ is hydroxyl; one of $R^3$ and $R^4$ is hydrogen and the other is methyl. Salts, hydrates, solvates, prodrugs and N-oxides of the pentacyclic acid triterpene compounds are also contemplated by the present invention. Representative types of plants to which the compound or composition of the present invention may be applied include, for example, corn, maize, soybean, wheat, rice, and canola plants. The compound or composition may also be applied to vegetable and fruit crops prone to bacterial disease such as apples, apricots, cherries, nectarines, peaches, pears, plums, prunes, quince almonds, chestnuts, filberts, pecans, pistachios, walnuts, citrus, blackberries, blueberries, boysenberries, cranberries, currants, loganberries, raspberries, strawberries, grapes, avocados, bananas, kiwi, persimmons, pomegranate, pineapple, tropical fruits, artichokes, kohlrabi, arugula, leeks, asparagus, lentils, beans, lettuce (e.g., head, leaf, romaine), beets, bok choy, malanga, broccoli, melons (e.g., muskmelon, watermelon, crenshaw, honeydew, cantaloupe), brussels sprouts, cabbage, cardoni, carrots, napa, cauliflower, okra, onions, celery, parsley, chick peas, parsnips, chicory, peas, chinese cabbage, peppers, collards, potatoes, cucumber, pumpkins, cucurbits, radishes, dry bulb onions, rutabaga, eggplant, salsify, escarole, shallots, endive, soybean, garlic, spinach, green onions, squash, greens, sugar beets, sweet potatoes, turnip, swiss chard, horseradish, tomatoes, kale, and turnips.

It is anticipated that the methods described herein will be applicable to preventing or inhibiting a variety of bacterial infections of plants. Pseudomonadaceae, Rhizobiaceae, Enterobacteriaceae, Corynebacteriaceae and Streptomycetaceae bacteria are all economically significant plant pathogens that may be controlled by the present invention. Non-limiting examples of specific plant pathogens that may be effectively inhibited by the methods described herein include: *Xanthomonas* species, such as, for example, *Xanthomonas campestris* pv. *oryzae; Pseudomonas* species, such as, for example, *Pseudomonas syringae* pv. *lachrymans*; and *Erwinia* species, such as, for example, *Erwinia amylovora*. It is also anticipated that the methods of preventing or inhibiting bacterial infections of plants described herein may also include use of compositions further comprised of antimicrobial agents such as bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Methods of preventing or inhibiting bacterial infections described herein can be used to treat all plants and parts of plants. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and the parts of plants with the active compounds according to the invention is carried out directly or by action on their surroundings, habitat or storage space, according to customary treatment methods, for example by dipping, spraying, evaporating, atomizing, broadcasting, spreading-on and, in the case of propagation material, in particular in the case of seeds, furthermore by one- or multi-layer coating. In the context of certain embodiments of this invention, the active compound is a pentacyclic acid triterpene. In the context of other embodiments of this invention, the pentacyclic acid triterpene is combined in the composition with another active compound that is an antimicrobial agent or antibiotic.

Agriculturally Acceptable Carriers and Compositions

Depending on their particular physical and/or chemical properties, the pentacyclic acid triterpene compounds and compositions can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the pentacyclic acid triterpene compounds and compositions with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The pentacyclic acid triterpene compounds and compositions can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants. In the context of certain embodiments of this invention, the active compound is a pentacyclic acid triterpene. In the context of other embodiments of this invention, the pentacyclic acid triterpene is combined in the composition with another active compound that is an antimicrobial agent or antibiotic.

The pentacyclic acid triterpene compounds and compositions according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

EXAMPLES

The following examples illustrate the use of compounds of the present invention and the preparation of formulations comprising these compounds. The examples demonstrate many uses of the compounds and are not intended to limit the scope of the present invention. Those of skill in the art should, in light of the present disclosure, appreciate that many changes can be made in the specific embodiments which are disclosed and still obtain a like or similar result without departing from the spirit and scope of the invention.

Example 1

Synthesis of Ursane or Oleanane Scaffold Derivative Compounds of Invention

The following methods are disclosed for obtaining compounds useful in the practice of this invention. Although the schematic drawings shown in FIG. 1-4 depict synthesis of various Ursane scaffold derivatives through use of Ursolic acid as a precursor compound, one skilled in the art would recognize that equivalent Oleanane scaffold derivatives could also be obtained through use of Oleanolic acid as a precursor compound. Similarly, one skilled in the art would also recognize that certain derivatives of either Ursolic or Oleanolic acid could also be used in place of Ursolic or Oleanolic acid as potential precursor molecules in the synthetic schemes shown in FIGS. 2,3,4, and 5 to derive Ursane or Oleanane derivatives with substitutions at positions in addition to $R_1$ (C-2). For example, Compound 99 (30-hydroxyursolic acid), Compound 195 (20B-hydroxyursolic acid), Compound 255 (Asiatic acid), Compound 323 (Caulophyllogenin), Compound 430 (Pygenic Acid B) or Compound 455 (Echinocystic Acid) might be substituted for compound 1 in the schemes outlined in FIGS. 1-4. Alternatively, Compound 107 (2-hydroxyoleanic acid), Compound 108 (Corosolic acid), Compound 192 (Euscaphic acid), Compound 203 (Tormentic acid), Compound 255 (Asiatic acid), Compound 314 (Madecassic acid) or Compound 456 (Pygenic Acid A) might be substituted for compound 4 in the schemes outlined in FIGS. 1-4. In substituting these alternative scaffolds, one skilled in the art would recognize that certain groups such as hydroxyls present at alternative positions on the scaffold may be reactive under certain conditions and thus require either modification of the reaction conditions and/or use of suitable protecting reagents.

i) Synthesis of 2α-hydroxy-oleanolic acid and 2β,3β epoxide methyl ursenate

The steps involved in the synthesis of 2α-hydroxy-oleanolic acid are diagrammed in FIG. 2. A detailed description of each of those steps is as follows.

To prepare compound 2 (FIG. 2), Oleanolic acid (2.19 g, 4.8 mmol) was suspended in dichloromethane (200 ml) and stirred at room temperature for several minutes followed by the addition of Dess-Martin reagent (2.44 g, 5.8 mmol). The reaction was quenched after 2 hrs by the addition of water. The reaction layers were separated and the aqueous layer washed (2×) with dichloromethane. The combined organics were dried and evaporated to leave an off-white solid. The solids were purified by several triturations in diethyl ether and the yield was quantitative.

To prepare Compound 3 (FIG. 2), Compound 2 (2.28 g, 5.01 mmol) was suspended in dichloromethane (120 ml) and chilled for several minutes in an ice water bath. TEA (7.02 ml, 50.1 mmol) and trifluoromethane sulfonate (4.53 ml, 25.1 mmol) were added to the cold solution and stirred for 1.5 hrs. The reaction was quenched by the addition of ice water and the aqueous layers washed with dichloromethane. The combined organics were dried and evaporated to leave a reddish oily residue. This residue was then dissolved in dichloromethane and chilled in an ice water bath. mCPBA (3.73 g, 17.54 mmol) was added and the mixture kept on ice for several minutes followed by stirring at room temperature.

To prepare Compound 4 (2α-hydroxy-oleanolic; FIG. 2), Compound 3 (468 mg, 0.99 mmol) was dissolved in ethanol (25 ml) and cooled in an ice water bath. Sodium borohydride (208 mg, 5.5 mmol) was added and the mixture was kept cold and stirred for 2 hrs. The reaction was quenched by the addition of 5% aqueous HCl and the product isolated by dichloromethane extraction. The organics were dried and evaporated to leave an off-white solid. Product was purified by column chromatography.

To prepare 2β,3β epoxide methyl ursenate (Compound 5, FIG. 2), the Mitsunobu Reaction can be used as described in Garcia-Granados, A. et al. *J. Org. Chem.* 2003, 68, 4833-4844. Compound 4 will be dissolved in an appropriate solvent, preferably DMF, and stirred with triphenylphosphine ($PPh_3$) at an appropriate temperature, preferably 0° C., followed by the addition of diethylazodicarboxylate (DEAD) and then stirred at reflux for preferably 2 or more hours.

i) Synthesis of 2α-hydroxy-oleanolic acid and 2β,3β epoxide methyl ursenate

Figure 3:
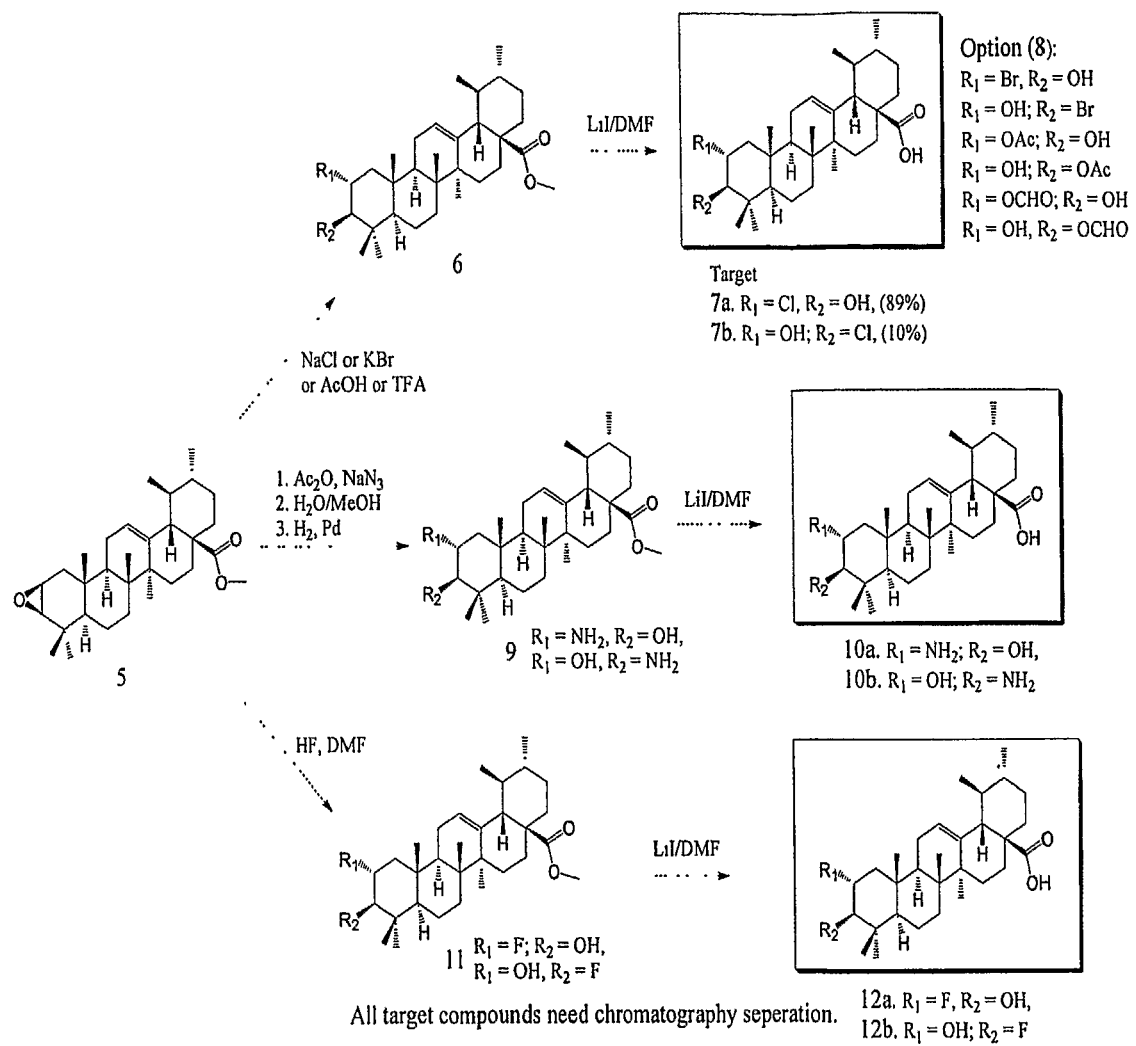
FIG. 3 shows a synthetic scheme for obtaining pentacyclic acid triterpenes with halo, hydroxy, acetyl, or amine (—NH2) groups at the R1 or R2 positions with pentacyclic acid triterpene C-2/C-3 epoxide intermediate precursors.

The steps involved in the synthesis of 2α,3β substituted methyl ursenate and related derivatives are diagrammed in FIG. 3. A detailed description of each of those steps is as follows.

To prepare 2α,3β substituted methyl ursenate, preferred synthetic procedures are described in (Garcia-Granados, A. et al. 2003). As shown in FIG. 3, 2α,3β epoxide methyl ursenate is stirred with chlorine anions of the reagent to produce Compounds 7a and 7b. As noted other halide anions can also be used. O-acetyls can be prepared using acetic acid and trifluoroacetic acid (TFA) would be preferred to produce formyloxy derivatives at either C-2 or C-3.

Figure 4:
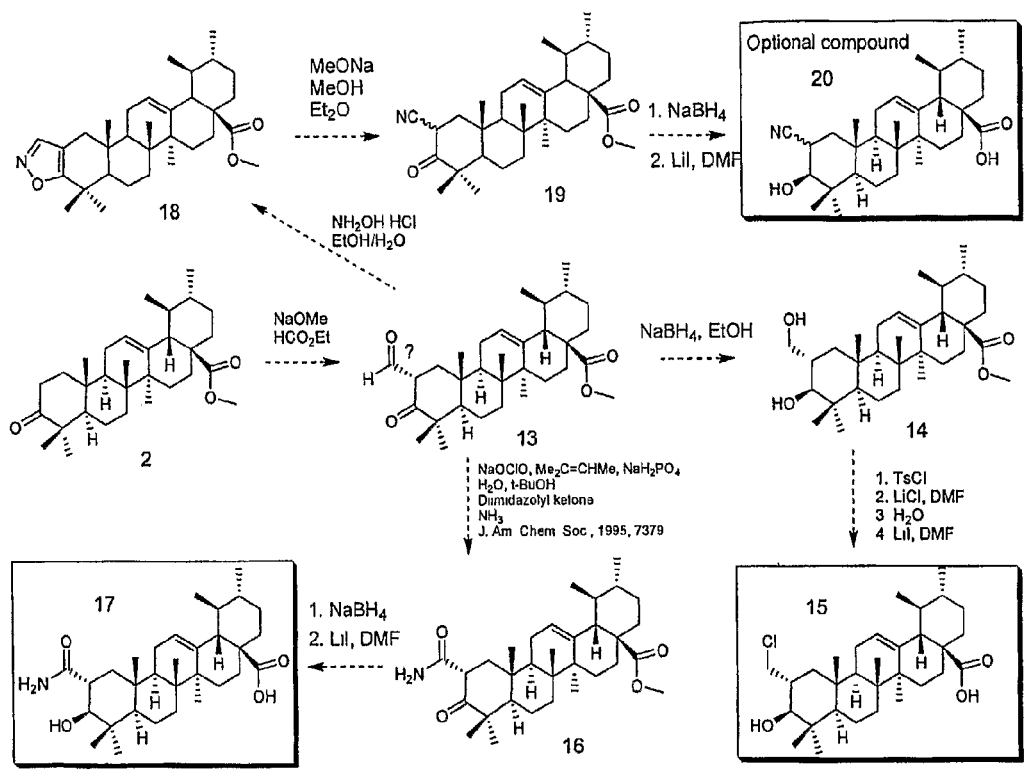
FIG. 4 shows a synthetic scheme for obtaining pentacyclic acid triterpenes with cyano, $C_{1-2}$ alcohols, $C_{1-2}$ (halo)alkyl, $C_1$ (chloro)alkyl, —C(O)H, and —C(O)NH$_2$ groups at R1 with pentacyclic acid triterpene C-3 enone intermediate precursors.
Figure 5:
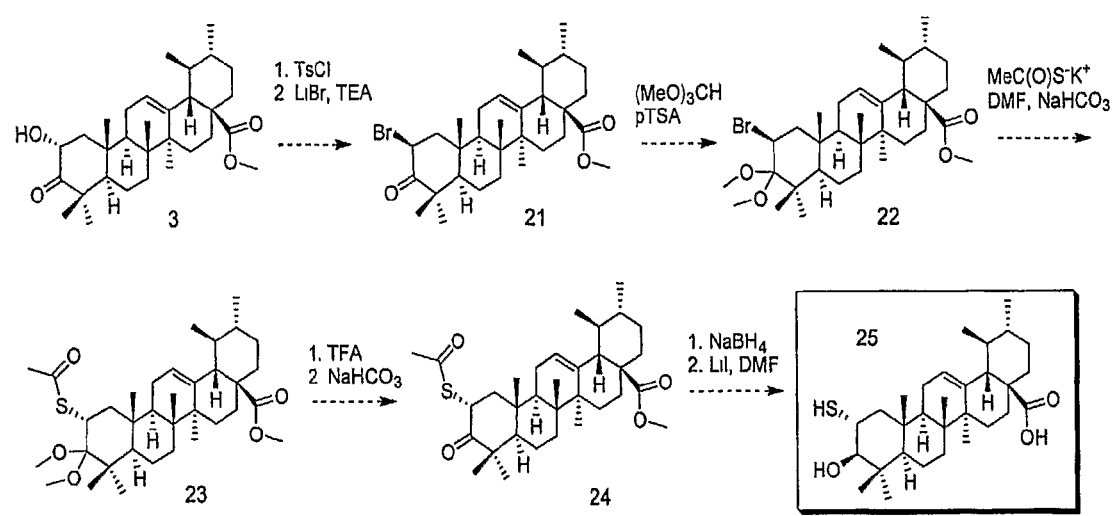
FIG. 5 shows a synthetic scheme for obtaining pentacyclic acid triterpenes with sulfhydryl groups at R1 with pentacyclic acid triterpene C-2 hydroxy/C-3 enone intermediate precursors.

The synthetic procedures shown in FIG. 4 have been previously described by Honda, T. et al. *Bioorg Med Chem. Lett.* 1999, 9, 3429-3434 and Honda, T. et al. *Bioorg Med Chem. Lett.* 1998, 8, 2711-2714.

Example 2

Inhibition of Biofilm Formation by Exemplary Pentacyclic Acid Triterpene Compounds and Structure Activity Relationships To illustrate the effect of various substitutions at various R-group positions of the ursane and oleanane scaffolds on biofilm inhibition, the exemplary pentacyclic acid triterpene compounds 99, 107, 108, 110, 116, 188, 189, 192, 195, 203, 225, 255, 314, and 323 described in the preceding portions of this application were tested for inhibition of biofilm activity as follows.

A microtiter plate assay was used to quantitatively measure the effect each tested compound had on the ability of bacteria to form a biofilm. In this example, a concentrated solution of each compound tested was loaded separately into three separate wells of a polystyrene microtiter plate. In addition, each assay included triplicate wells correlating to negative and positive controls. For the positive controls, biofilm inhibitors of known activity were used, whereas no inhibitors were added to wells correlating to negative controls. Next, 150 μl of sterile media was added to each well (LB media with 0.2% glucose)—followed by 50 μl of the appropriate bacterial inoculum. Thus, each well contained a final volume of approximately 200 μl (not including the volume of the concentrated inhibitor). The final concentration of each biofilm inhibitor tested in the assay was 10 μg/ml. The microtiter plates were then placed on a shaker for approximately 20 to 24 hours at room temperature. After the incubation period, the microtiter plate was removed from the shaker, rinsed, and stained. During the rinsing step, the test compound, media, and bacterial inoculum solution was drained from the plate, approximately 300 μL of 0.1M phosphate buffered saline (PBS) was added to each well, which was subsequently drained from the plate. The rinsing step removed any suspended cells from the assay. An 0.1% crystal violet stain was added to each well for approximately 20 minutes. Next, the crystal violet solution was drained from the microtiter plate. The plate was rinsed with PBS as described above four (4) times to remove any excess stain from the plate. Following the PBS rinsing steps, the plate was eluted with 250 μL/well of ethanol, which improved the detection of the stain. The plate was immediately analyzed spectrophotometrically at 540 nm using a microtiter plate reader.

The inhibitory effect each compound had on the bacteria's ability to form a biofilm on the surface of each well was determined as follows: The optical densities (O.D.) observed for each set of three (3) wells correlating with a test compound or control were averaged. The average O.D. for each test compound was compared to the average O.D. of the negative control (the positive control was employed to verify proper assay function). In general, biofilm inhibition activity is inversely proportional to O.D., whereby, for example, low O.D. readings correlate with significant inhibition activity and high O.D. readings correlate with small or no inhibition activity. The approximate percent inhibition observed for each compound was calculated by comparing the average O.D. for each compound to the average O.D. for the negative controls. Table 2 summarizes the average percent inhibition observed for the tested compounds listed against biofilms generated by *Pseudomonas aeruginosa*.

TABLE 2

Compound Biofilm Inhibition - *Pseudomonas aeruginosa*

| Compound Number | % Biofilm Inhibition of Pseudomonas Aeruginosa |
|---|---|
| 99 | 30% |
| 107 | 46% |
| 108 | 52% |
| 110 | 35% |
| 116 | 48% |
| 188 | 62% |
| 189 | 35% |

TABLE 2-continued

Compound Biofilm Inhibition - *Pseudomonas aeruginosa*

| Compound Number | % Biofilm Inhibition of Pseudomonas Aeruginosa |
|---|---|
| 192 | 32% |
| 195 | 25% |
| 203 | 43% |
| 225 | 35% |

As shown in Table 2, the biofilm inhibitors referenced therein exhibited significant biofilm inhibition activity. Notably, in wells correlating to compounds 188, 108, and 116, a reduction in biofilm mass of 62%, 52%, and 48%, respectively, was observed. To further demonstrate the ability of the compounds disclosed herein to inhibit biofilm formation generated by a diverse array of microorganisms, compounds 108, 110, 225, 255, 314, and 323 were evaluated for their activity against *Escherichia coli* using the assay described above. Each compound was tested at a final concentration of 10 μg/ml. The data are summarized in Table 3 below.

TABLE 3

Compound Biofilm Inhibition - *Escherichia coli*

| Compound Number | % Biofilm Inhibition of *E. coli* |
|---|---|
| 108 | 74% |
| 110 | 80% |
| 225 | 35% |
| 255 | 75% |
| 323 | 35% |
| 430 | 60% |

As shown in Table 3, the biofilm inhibitors referenced therein exhibited significant biofilm inhibition activity against *E. coli*. Notably, in wells correlating to compounds 110, 255, and 108, a reduction in biofilm mass of 80%, 75%, and 74%, respectively, was observed. Compound 110 was further tested against *Staphylococcus epidermidis*. Using the microtiter assay described above, at the final concentration of 10 μg/ml, compound 110 was shown to inhibit biofilm formation by *S. epidermidis* by approximately 25%.

The foregoing data illustrate the effect of various substitutions at various R-group positions of the ursane and oleanane scaffolds on reducing biofilm growth produced by a wide variety of bacteria.

Examples of the structure activity relationships provided by the discovery and analysis of the relative biofilm inhibiting activity of the preceding pentacyclic acid triterpene compounds are illustrated in the following Table 4. Comparison of the inhibition activity of compound 108 to 110 shows that the hydroxy group at position C2 in compound 108 increases inhibition when tested against *P. aeruginosa*. Furthermore, comparing the biofilm inhibition activity of compounds 314 and 108 shows that the hydroxy group at position C5 of compound 314 reduces inhibition when tested against *E. coli*. Still further, comparing the biofilm inhibition activity of compounds 108 and 203 shows that the hydroxy group at position C11 of compound 203 reduces inhibition when tested against *P. aeruginosa*. As further shown through the biofilm inhibition exhibited by compounds 108 and 188, the hydroxycinnamoyl group at position C3 and the hydroxy group at position C10 of compound 188 increase inhibition when tested against *P. aeruginosa*. The improved activity conferred by the hydroxycinnamoyl group at position C3 is further evidenced in the comparison of compound 188 and compound 195, where presence of the hydroxycinnamoyl group as opposed to a hydroxy group at C3 increases inhibition from 25 to 62%.

TABLE 4

Structure Activity Relationships

| Compound Number | % Biofilm Inhibition of Pseudomonas Aeruginosa | R1 at C2 | R2 at C3 | R4 at C5 | R9 at C10 |
|---|---|---|---|---|---|
| 99 | 30% | | | | |
| 107 | 46% | | | | |
| 108 | 52% | —OH | —OH | —CH3 | |
| 110 | 35% | —H | —OH | —CH3 | |
| 116 | 48% | | | | |
| 188 | 62% | —H | (HC) | —CH3 | —OH |
| 189 | 35% | | | | |
| 192 | 32% | | | | |
| 195 | 25% | —H | —OH | —CH3 | —OH |
| 203 | 43% | | | | |
| 225 | 35% | | | | |

Example 3

*Escherichia coli* Biofilm Inhibition by Pentacyclic Acid Triterpenes

Biofilm inhibition experiments are conducted using an assay adapted from the reported protocol described in Pratt and Kolter, 1998, Molecular Microbiology, 30: 285-293; Li et al., 2001, J. Bacteriol., 183: 897-908. Similar experiments have previously been completed for exemplary pentacyclic acid triterpene compounds as described in U.S. patent application Ser. No. 11/181,556 and U.S. Provisional Patent Application Ser. No. 60/587,680, both herein incorporated by reference in their entirety. *E. coli* clinical strain UTI89 is grown in LB in 96 well plates at room temperature for one or two days without shaking. *E. coli* laboratory strain JM109 is grown in LB plus 0.2% glucose in 96 well plates at room temperature for one day without shaking. To quantify the biofilm mass, the suspension culture is poured out and the biofilm is washed three times with water. The biofilm is stained with 0.1% crystal violet for 20 minutes. The plates are then washed three times with water. OD reading at 540 nm is measured to quantify the biofilm mass at the bottom of the wells. Then 95% ethanol is added to dissolve the dye at the bottom and on the wall and the OD reading at 540 nm is measured to quantify the total biofilm mass. To study the overall effect of the compounds (3.6 mg/mL in 100% ethanol as stock solution), compounds are added with the inoculation and a time course of biofilm mass is measured. Appropriate amounts of 100% ethanol are added to each sample to eliminate the effect of solvent. Each condition has 3-4 replicates on each plate and is performed over multiple days. Reductions in biofilm mass of 30 to 80% or greater relative to the negative controls are taken as an indication that the compounds tested are biofilm inhibitors.

Example 4

Inhibition of Biofilm Formation by Compounds of the Invention

*Pseudomonas aeruginosa* PA01 Assays

An overnight culture of *P. aeruginosa* PAO1 in LB+1% citrate is prepared. It is incubated at 37° C. shaker for 24 hours. A 1:20 dilution of the overnight culture is prepared. Test compounds are diluted appropriately with a volume of ethanol followed by shaking for approximately 5 minutes and then diluted with an appropriate volume of water.

Replicate 96-well plates are prepared, preferably two to four replicates, with appropriately diluted overnight culture and test compound in each well. Preferably, test compounds are prepared at 10 to 30 micrograms per milliliter. On each 96-well plate controls are appropriately prepared with at least one set of negative controls consisting of overnight culture and ethanol/water diluent and another set of negative controls consisting of growth media and ethanol/water diluent. The ethanol/water diluent in the negative control wells is added such that the final concentration of ethanol/water in the negative control wells is identical to the final concentration of ethanol/water in the wells receiving the positive control or pentacyclic acid tripterpene compound(s). Plates are covered with foil at room temperature and shaken for approximately 24 hours.

After shaking absorbance of the wells of the plates are determined, preferably at 630 nanometers. Liquid is than aspirated out of the wells and each well is filled with diluted crystal violet, preferably approximately 250 microliters of a 1:4 dilution, and allowed to stand for approximately 10 minutes. Each well of the plate is washed, preferably four times, with PBS with approximately one minute between each wash. After the final wash is aspirated out, the plate may be turned over onto paper towels to dump out excess PBS. 95% ethanol is added to each well, preferably 250 microliters. Absorbance of each well of a plate is determined, preferably at 540 nm. Preferably slight shaking is performed during the absorbance reading for approximately 5 minutes. Each well of the plate is then diluted 1 to 50 with ethanol in a separate plate, preferably 145 ul of 95% ethanol and 5 uL from the original plate, and absorbance is determined. Preferably, slight shaking for approximately 3 minutes is performed.

Biofilm inhibition in each well is determined by subtracting the absorbance of the wells with test compounds from wells with controls containing overnight culture subtracting out controls with only media. A typical positive result of biofilm inhibition confirmed with replicates would be 30 percent to 80 percent or more inhibition of biofilm formation in the wells with the positive control and test pentacyclic acid triterpene(s) compound(s) as compared to the wells with the negative controls of overnight culture that receive no compound.

Example 5

Effect of Pentacyclic Acid Triterpenes on Mature Biofilms of Clinical Isolates of *P. aeruginosa*

Clinical isolates of *P. aeruginosa* from cystic fibrosis patients are passed twice on tryptic soy agar with 5% sheep blood after retrieval from −80° C. and then grown overnight in CAMHB. After dilution of a culture to 0.5 McFarland in broth medium, 100 μl is transferred in triplicate to wells of a flat-bottom 96-well microtiter plate. Bacterial biofilms are formed by immersing the pegs of a modified polystyrene microtiter lid into this biofilm growth plate, followed by incubation at 37° C. for 20 hours with no movement.

Peg lids are rinsed three times in sterile water, placed onto flat-bottom microtiter plates containing either the pentacyclic acid triterpene(s) or a positive control such as Asiatic acid (Compound 255) at 5 ug/ml in 100 μl of CAMHB per well and incubated for approximately 40 hours at 37° C. On each 96-well plate controls are appropriately prepared with at least one set of negative controls consisting of CAMHB growth media and ethanol/water diluent. The ethanol/water diluent in the negative control wells is added such that the final concentration of ethanol/water in the negative control wells is identical to the final concentration of ethanol/water in the wells receiving the positive control or pentacyclic acid triptperpene compound(s).

Pegs are rinsed, placed in a 0.1% (wt/vol) crystal violet solution for 15 min, rinsed again, and dried for several hours. To solubilize adsorbed crystal violet, pegs were incubated in 95% ethanol (150 μl per well of a flat-bottom microtiter plate) for 15 min. The absorbance is read at 590 nm on a plate reader. The wells containing asiatic acid are compared to negative controls. Negative controls are prepared as stated above by but without the positive control compound or the pentacyclic acid triterpene compound.

Detachment of mature biofilms against clinical isolates of between 25% to 74% is observed in positive control wells relative to negative control wells. A typical positive result of biofilm inhibition confirmed with replicates would be about 25 percent to 75 percent or more inhibition of biofilm formation in the wells with the test pentacyclic acid triterpene(s) compound(s) as compared to the negative control wells (i.e. biofilm coated pegs incubated with ethanol/water diluent alone).

Example 6

Effect of Pentacyclic Acid Triterpene Compounds in Combination with Tobramycin on Biofilm Formation of *Pseudomonas aeruginosa*

Biofilm formation of *P. aeruginosa* is evaluated using a standardized biofilm method with a rotating disk reactor (RDR). This method provides a model resembling the formation of biofilms in cystic fibrosis patients. The rotating disk reactor consists of a one-liter glass beaker fitted with a drain spout. The bottom of the vessel contains a magnetically driven rotor with six 1.27 cm diameter coupons constructed from polystyrene. The rotor consists of a star-head magnetic stir bar upon which a disk is affixed to hold the coupons. The vessel with the stir bar is placed on a stir plate and rotated to provide fluid shear. A nutrient solution (AB Trace Medium with 0.3 mM glucose, see Table 3 below for composition) was added through a stopper in the top of the reactor at a flow rate of 5 ml/min. The reactor volume was approximately 180 ml and varied slightly between reactors depending on the placement of the drain spout and the rotational speed of the rotor. At a volume of 180 ml, the residence time of the reactors was 36 minutes. The reactors were operated at room temperature (c.a. 26° C.).

TABLE 3

Composition of the AB Trace Medium for the RDR test.

| Component | Formula | Concentration (g/l) |
|---|---|---|
| Disodium phosphate | $Na_2HPO_4$ | 6.0 |
| Monopotassium phosphate | $KH_2PO_4$ | 3.0 |
| Sodium Chloride | NaCl | 3.0 |
| Ammonium sulfate | $(NH_4)_2SO_4$ | 2.0 |
| Magnesium chloride | $MgCl_2$ | 0.2 |
| Glucose | $C_6O_{12}H_6$ | 0.054 |
| Calcium chloride | $CaCl_2$ | 0.010 |
| Sodium sulfate | $Na_2SO_4$ | 0.011 |
| Ferric chloride | $FeCl_3$ | 0.00050 |

For each test, two RDRs are operated in parallel with one receiving test compound and the other serving as an untreated control. In this case, the test compound is either a positive control such as Asiatic, Madecassic, or Corosolic acid or a pentacyclic acid triterpene compound. The RDRs are sterilized by autoclave, filled with sterile medium and inoculated with *P. aeruginosa* strain PAO1. The reactors are then incubated at room temperature in batch mode (no medium flow) for a period of 24 hours, after which the flow is initiated for a further 24 hour incubation. Test compounds are dissolved in 10 ml ethanol to achieve a concentration of 1.8 mg/ml. After the 48 hours of biofilm development described above, 10 ml of ethanol containing the test compounds is added to the reactor to achieve a final concentration of approximately 50, 100, or 200 μg/ml. Control reactors receive 10 ml of ethanol. The reactors are then incubated for an additional 24 hours in batch (no flow) mode. After this incubation period, the six coupons are removed from each reactor and placed in 12-well polystyrene tissue culture plates with wells containing either 2 ml of a 100 μg/ml tobramycin solution or 2 ml of phosphate-buffered saline (PBS). These plates are incubated at room temperature for two hours. The coupons are then rinsed by three transfers to plates containing 2 ml of fresh PBS. For each two RDR reactors run in parallel, four sets of three coupons are obtained: one set with no test compound treatment and no tobramycin treatment, one set with no test compound treatment and tobramycin treatment, one set treated with a test compound treatment and no tobramycin treatment, and one set treated with a test compound treatment and tobramycin. After rinsing, one coupon of each set of three is stained with a LIVE/DEAD® BacLight™ Bacterial Viability Kit (Invitrogen, Carlsbad, Calif.) and imaged using epifluorescent microscopy. The remaining two coupons are placed in 10 ml of PBS and sonicated for five minutes to remove and disperse biofilm cells. The resulting bacterial suspensions are then serially diluted in PBS and plated on tryptic soy agar plates for enumeration of culturable bacteria. The plates are incubated for 24 hours at 37° C. before colony forming units (CFU) were determined.

Averages from experiments performed on three separate days for each test compound can be calculated. The values can be reported as $\log_{10}$ CFU. Reductions in the $\log_{10}$ CFU of between about 0.5 to 1.2 ($\log_{10}$ CFU) are observed in wells containing both Asiatic, Madecassic, or Corosolic acid at the tested concentrations and Tobramycin relative to control wells containing only Tobramycin. A typical reduction in $\log_{10}$ CFU of between about 0.5 to 1.2 or more ($\log_{10}$ CFU) is expected in the wells with both the test pentacyclic acid triterpene(s) compound(s) at 50-200 μg/ml and Tobramycin as compared to the wells containing only Tobramycin. Wells containing either a positive control compound such as Asiatic, Madecassic, or Corosolic acid or a pentacyclic acid triterpene compound alone are not expected to result in $\log_{10}$ CFU reductions of greater than 0.5 relative to wells that receive only ethanol (i.e. are not treated with any of Asiatic acid, Madecassic acid, Corosolic acid, a pentacyclic acid triterpene compound, or Tobramycin).

As a comparison to multiple published clinical studies, reduction in $\log_{10}$ CFU of between about 0.5 to 1.2 or more with a pentacyclic acid triterpene compound in combination with tobramycin relative to tobramycin alone would predict that improved lung function (FEV or forced expiratory volume) and decreased average CFU (density) in sputum from patients with cystic fibrosis would be observed in a combination therapy involving these compounds (Ramsey, Bonnie W. et. al., "Intermittent administration of inhaled tobramycin in patients with cystic fibrosis", New England J. Medicine 340 (1):23-30, 1999; Saiman, L. "The use of macrolide antibiotics in patients with cystic fibrosis", Curr Opin Pulm Med, 2004, 10:515:523; Pirzada, O. et al. "Improved lung function and body mass index associated with long-term use of Macrolide antibiotics.", J. Cystic Fibrosis, 2003, 2, p. 69-71). Using the endpoints listed in these publications and used in Cystic Fibrosis clinical trials, a reduction in $\log_{10}$ CFU of between about 0.5 to 1.2 or more with a pentacyclic acid triterpene compound in combination with tobramycin relative to tobramycin alone would demonstrate that a combined treatment of tobramycin and a compound of the invention could provide benefit to Cystic Fibrosis patients or other people suffering from chronic lung infections. A reduction in $\log_{10}$ CFU of between about 0.5 to 1.2 or more with a pentacyclic acid triterpene compound in combination with tobramycin relative to tobramycin alone would also demonstrate that the pentacyclic acid triterpene compound (s) of the invention in combination with an antibiotic would remove biofilms from teeth, skin, tissues, catheters, medical devices, and other surfaces.

Example 7

Effect of Pentacyclic Acid Triterpene Compounds on Biofilm Growth and Inhibition with *Streptococcus mutans* 25175 and *Streptococcus sobrinus* 6715

Pentacyclic Acid Triterpene Compounds are tested against *S. mutans* 25175 and *S. sobrinus* 6715 at a concentration of 40 ug/ml to 200 ug/ml using the method described in Example 2. The use of 1 mL polycarbonate tubes were used in place of 96 well polysterene microtiter plates.

Exposure of *S. mutans* 25175 and *S. sobrinus* 6715 to pentacyclic acid triterpene compounds at a concentration of 40 ug/ml to 200 ug/ml is expected to result in biofilm growth inhibition of 30 percent to 80 percent or more as compared to the wells with negative controls of overnight culture that receive no compound.

Example 8

The Effects of Pentacyclic Acid Triterpene Compounds on the Binding to and Invasion of *E. coli* Clinical Strain UTI89 Against Bladder Epithelial Cells The effect of pentacyclic acid triterpene test compounds on bacterial invasion of *E. coli* clinical strain UTI89 is studied as described in Elsinghorst, et al. 1994, Methods Enzymol, 236: 405-420; and Martinez et al., 2000, EMBO J., 19:2803-2812. Epithelial bladder cells are grown in plates. Positive controls such as Asiatic acid, corosolic acid, or ursolic acid and pentacyclic acid triterpene test compounds are added at concentrations of 10 µg/ml, 20 µg/ml, or 40 µg/ml to bacteria and epithelial cells for approximately 5, 15, 30, or 60 minutes with approximately $10^7$ CFU of *E. coli*. Binding is assessed at time zero and invasion is assessed at approximately 5, 15, 30, or 60 minutes from completing the mixture of compound, bacteria, and epithelial cells. As a negative control, ethanol was added to cells to a final concentration of 0.1%. The effect of bacterial viability and bacterial adherence during the infection period is evaluated according to the methods described in Martinez et al., 2000, EMBO J., 19:2803-2812. The positive control and test pentacyclic acid triterpene compounds are not expected to affect the binding of *E. coli* to bladder epithelial cells. The positive control and test pentacyclic acid triterpene compounds are expected to reduce the invasion of *E. coli* into bladder epithelial cells.

Example 9

Bladder Concentrations of the Pentacyclic Acid Triterpene Compounds in Rats

Pharmacokinetic studies of pentacyclic acid triterpene compounds in rats are performed by dosing Rats at 50 mg/kg (oral). Two animals are assigned to the each group. Prior to dosing, a baseline blood sample is taken from each animal. At time zero for the pentacyclic acid triterpene compound, a single bolus dose in 50% Labrasol (Gattefosse) is given to each animal. Bladders are analyzed at 24 hours. Concentrations of both asiatic acid and madecassic acid in the bladder are expected to be greater than approximately 10 µg/g at 24 hours.

These experiments demonstrate that the pentacyclic acid triterpene compound is expected to be in adequate concentration in the bladders of mice to reduce invasion of bacteria and the formation of biofilms.

Example 10

The Effects of the Pentacyclic Acid Triterpene Compounds on the Pathogenesis of *E. coli* Clinical Strain UTI89 in Mice The procedures in this example have been previously reported by Justice, S. et al. Differentiation and development pathways of uropathogenic *Escherichia coli* in urinary tract pathogenesis. PNAS, 2004, 101(5), p. 1333-1338. Briefly, *E. coli* UTI89-[pCOMGFP] is prepared after retrieval from frozen stocks by inoculating appropriately in LB medium statically for approximately 20 hours. Cells are harvested and suspended in 1 ml of PBS. Cells are diluted appropriately to achieve approximately a $10^8$ CFU or $10^7$ CFU input into C3H/HeN mice (2 mice per group).

Mice were deprived of water for approximately two hours. In experiment 1, all mice are anesthetized with 0.15 cc ketamine cocktail. In experiment 2, all mice are anesthetized with isofluorane. In experiment 1, urine is dispelled from the bladders and approximately 40 µg/ml of pentacyclic acid triterpene test compound or an appropriate amount of ethanol as control was introduced into the bladders via catheterization of the urethra using a tubing coated tuberculin syringe. 30 minutes is allowed to elapse. In experiment 2, bladders are not pre-incubated with test compounds. Bladders are then expelled and an inoculum of $10^8$ CFU (Experiment 1) or $10^7$ CFU (Experiment 2) of *E. coli* containing 40 µg/ml of test compound or an equivalent amount of ethanol as controls are introduced into the bladders as indicated above.

In experiment 1 five hours elapses and in experiment 2 six hours elapses, and the mice are anesthetized and sacrificed appropriately. The bladders are removed, bisected, stretched, and fixed in 3% paraformaldehyde for 1 hour at room temperature. Bladders are then permeabilized in 0.01% Triton/PBS for 10 minutes and counter stained with TOPRO3™ (Invitrogen, Carlsbad, Calif.) for 10 minutes for visualization by confocal microscopy. Bladders are mounted on Prolong™ antifade (Invitrogen, Carlsbad, Calif.).

In experiment 1, the pentacyclic acid triterpene is expected to demonstrate about a 70% or greater reduction, respectively, in biofilm pods or IBCs in the bladders of mice as compared to the controls by examination with confocal microscopy. In experiment 2, the pentacyclic acid triterpene is expected to demonstrate approximately a 60% reduction in large biofilm pods or large IBCs in the bladders of mice as compared to the controls by examination with confocal microscopy.

The results of these experiments would demonstrate that the compounds of the invention can interrupt the pathogenesis of clinical strains of *E. coli* in mice. Moreover, it becomes readily apparent the significant impact the compounds of the invention will have on treating chronic infections involving biofilms from the understanding described by Justice, S, et al. that biofilm pods or IBCs play an integral role in the recurrence of urinary tract infections (Justice, S. et al. Differentiation and development pathways of uropathogenic *Escherichia coli* in urinary tract patliogenesis. *PNAS*, 2004, 101(5), p. 1333-1338). In this publication the authors describe and their experiments demonstrate that IBCs prevent the mammalian immune response from eradicating the bacterial population and enable them to increase their numbers. Therefore, disabling this advantage, or interrupting the pathogenesis of bacteria, the compounds of the invention work in combination with a mammalian immune response or an antibiotic, as demonstrated in other examples in this specification, to reduce, prevent, treat, or eradicate infections involving biofilms. Furthermore, this animal model is representative of chronic lung, ear, and sinus infections, acne, rosacea, and chronic wounds. It is also representative of the cycle of pathogenesis of other *E. coli* infections such as, but not limited to, pyelonephritis, prostatitis, meningitis, sepsis, and gastrointestinal infections.

Example 11

The Effects of the Pentacyclic Acid Triterpene Compounds on the Pathogenesis of *E. coli* Clinical Strain UTI89 in Mice The procedures in this example have been previously reported by Justice, S. et al Differentiation and development pathways of uropathogenic *Escherichia coli* in urinary tract pathogenesis. *PNAS*, 2004, 101(5), p. 1333-1338. Briefly, *E. coli* UTI89-[pCOMGFP] is prepared after retrieval from frozen stocks by inoculating appropriately in LB medium statically for approximately 20 hours. Cells are harvested and suspended in 1 ml of PBS. Cells are diluted appropriately to achieve approximately $10^7$ CFU input into C3H/HeN mice.

Mice are deprived of water for approximately two hours. All mice are anesthetized with isofluorane. Urine was dispelled from the bladders and an inoculum of approximately $10^7$ CFU of *E. coli* is introduced into the bladders as indicated above. Treatments of sulfamethoxazole and trimethoprim (SMZ/TMP), asiatic acid, and combination of SMZ/TMP and asiatic acid is evaluated.

Three mice or more do not receive the pentacyclic acid triterpene or SMZ/TMP during the experiment. Three or more mice receive the pentacyclic acid triterpene orally at approximately 25 milligram per kilogram twice a day beginning one day prior to infection each day during the experiment. The pentacyclic acid triterpene is prepared in 50% Labrasol®. Five mice or more receive SMZ/TMP in their drinking water at a concentration of 270 micrograms of SMZ per milliliter and 54 micrograms of TMP per milliliter immediately after infection throughout the experiment. Five mice or more receive the pentacyclic acid triterpene and SMZ/TMP in combination dosed according to the individual dosing groups. The experiment is performed for approximately 2 days after inoculation. Mice are anesthetized and sacrificed appropriately. The bladders are removed and colony forming units (CFU) are determined as previously described by Justice, S. et al.

The pentacyclic acid triterpene is expected to be superior to SMZ/TMP at preventing the colonization of bladders. The results of this experiment are expected to demonstrate that the compounds of the invention can be delivered orally to interrupt the pathogenesis of clinical strains of *E. coli* in mice. This experiment is also expected to demonstrate the compounds of the invention may be superior to conventional antibiotics.

Example 12

A Topical Gel was Prepared Containing 2% of by Weight of the Pentacyclic Acid Triterpenes with Azithromycin for Use in Treating Acne, Rosacea, and Skin Infections 0.25 gram of the pentacyclic acid triterpene is dissolved in 6.75 grams of ethanol. 0.2 grams of azithromycin was dissolved in this solution. 0.25 grams of hydroxypropyl methylcellulose was added with gentle stirring until a homogenous solution was obtained. 4.8 grams of water was then added with gentle shaking.

This formulation is stored for thirty days at 2° C. to 8° C., room temperature (approximately 22° C.), and at 30° C. It is expected to remain homogenous for thirty days at each storage condition. A formulation without antibiotic can also be prepared using this same procedure.

Example 13

Pharmaceutical Formulation for Nebulization of a Pentacyclic Acid Triterpene Compound Solutions are prepared comprising 2 mg/ml and 10 mg/ml of the pentacyclic acid triterpene in ethanol/propylene glycol/water (85:10:5). These solutions are nebulized separately by a ProNeb Ultra nebulizer manufactured by PARI. The nebulized solutions are collected in a cold trap, processed appropriately, and are detected by mass spectrometry. The pentacyclic acid triterpene is expected to be recovered from both formulations to demonstrate that nebulization can be used to deliver this compound to patients with lung infections.

Example 14

A Pentacyclic Acid Triterpene, 2% Toothpaste Formulation

Toothpaste preparations are prepared containing 2% pentacyclic acid triterpene with and without antibiotic and with and without polymer. Polymer, Gantre® S-97, was added to improve retention of the pentacyclic acid triterpene and antibiotic on teeth.

All of the dry ingredients are mixed together. Glycerin is slowly added while mixing. An aliquot of water is added slowly and thoroughly mixed. Peppermint extract is added and then the rest of the water is added while mixing. Madecassic acid and antibiotic are then added until homogenous.

Formulation A

| Ingredients | Parts By Weight |
| --- | --- |
| Sorbitol | 20.0 |
| Glycerin | 22.0 |
| Silica | 20 |
| Sodium lauryl sulfate | 2.0 |
| Xanthum gum | 1 |
| Madecassic Acid | 2.0 |
| Peppermint extract | 1.0 |
| Sodium fluoride | 0.3 |
| Water | 31.7 |

Formulation B

| Ingredients | Parts By Weight |
| --- | --- |
| Sorbitol | 20.0 |
| Glycerin | 22.0 |
| Silica | 20 |
| Sodium lauryl sulfate | 2.0 |
| Xanthum gum | 1 |
| Madecassic Acid | 2.0 |
| Triclosan | 0.3 |
| Peppermint extract | 1.0 |
| Sodium fluoride | 0.3 |
| Gantrez ® S-97 | 2.5 |
| Water | 28.9 |

Formulations A and B are prepared and stored for thirty days at 2° C. to 8° C., room temperature (approximately 22° C.), and at 30° C.

Example 15

Figure 6:
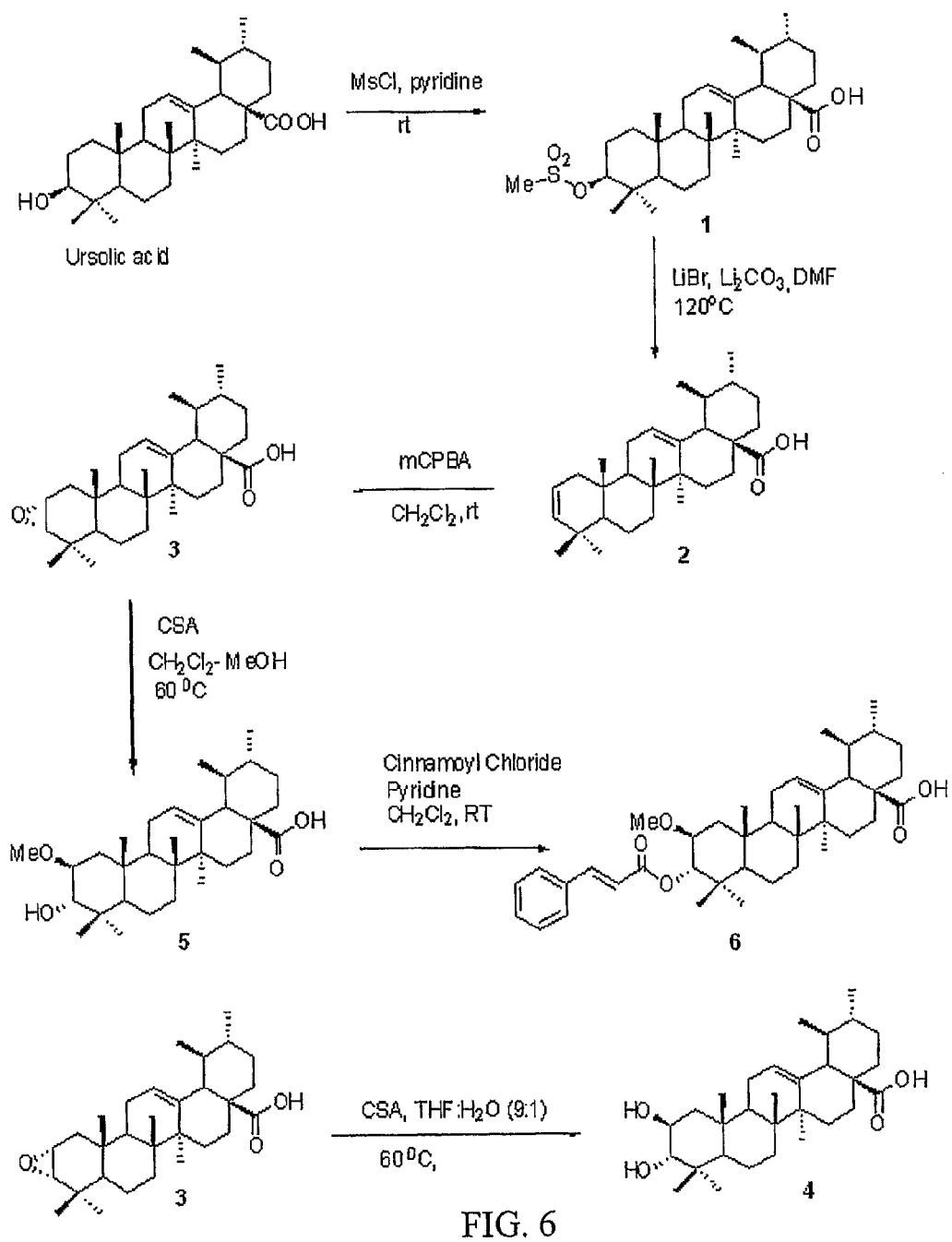
FIG. 6 shows a synthetic scheme for obtaining 2β,3α-dihydroxy-12-ursen-28-oic acid 2β-methoxy-3α-hydroxy-12-ursen-28-oic acid and 2β-methoxy-3α-cinnamoyl-12-ursen-28-oic acid from Ursolic acid.

Synthesis of 2β,3α-dihydroxy-12-ursen-28-oic acid, 2α-methoxy-3α-hydroxy-12-ursen-28-oic acid and 2β-methoxy-3α-cinnamoyl-12-ursen-28-oic acid The steps involved in the synthesis of 2β,3α-dihydroxy-12-ursen-28-oic acid, 2β-methoxy-3α-hydroxy-12-ursen-28-oic acid and 2β-methoxy-3α-cinnamoyl-12-ursen-28-oic acid are diagrammed in FIG. 6. A detailed description of each of those steps is as follows.

To prepare of Compound 1 (FIG. 6), Methanesulfonyl chloride (30 μL, 0.44 mmol) was added to a solution of ursolic acid (50 mg, 0.11 mmol) in pyridine (1 mL), and the reaction mixture was stirred at room temperature for 12 h. Then, the reaction mixture was diluted with $CHCl_3$ (10 mL) and extracted with 10% aqueous HCl solution (3×10 mL). The combined organic phases were dried ($Na_2SO_4$) and evaporated under vacuo to afford 51 mg (88%) of 1 as a white solid. $^1$H NMR ($CDCl_3$, 400 MHz) δ: 5.26-5.19 (m, 1H); 4.39-4.31 (m, 1H); 3.11 (s, 3H); 2.20 (t, 1H, J=6 Hz); 2.09-1.82 (m, 6H); 1.70-1.62 (m, 4H); 1.59-1.43 (m, 4H); 1.40-1.19 (m, 4H); 1.13-0.75 (m, 23H); 0.73 (s, 3H). ESI-TOF high acc m/z 557.3272 (M+Na$^+$, $C_{31}H_{50}O_5S$ requires 557.3271).

To prepare of Compound 2 (FIG. 6), the mixture of 1(100 mg, 0.19 mmol), LiBr (50 mg, 0.57 mmol), and $Li_2CO_3$ (47 mg, 0.63 mmol) in DMF (5 mL) was heated at 120° C. for 12 h. Then, the reaction mixture was diluted with ether (20 mL) and extracted with water (20 mL) and brine (20 mL). The combined organic phases were dried over $Na_2SO_4$, the solvent was evaporated and the crude product was purified by flash chromatography (5% EtOAc/Hexane) to yield 74 mg (90%) of 2 as a yellow solid. $^1$H NMR ($CDCl_3$, 400 MHz) δ: 5.49-5.35 (m, 2H); 5.33-5.19 (m, 1H); 2.21 (d, 1H, J=11 Hz); 2.08-1.83 (m, 6H); 1.79-1.42 (m, 6H); 1.40-1.21 (m, 5H); 1.19-0.78 (m, 21H); 0.74 (s, 3H). ESI-TOF high acc m/z 461.3392 (M+Na$^+$, $C_{30}H_{46}O_2$ requires 461.339).

To prepare Compound 3 (FIG. 6), MCPBA (15 mg, 0.086 mmol) was added to a solution of 2 (25 mg, 0.057 mmol) dissolved in dry $CH_2Cl_2$ (1 mL). The reaction mixture was stirred at room temperature for 12 h. Triethylamine (0.1 mL) was added and the solvent was removed. The crude product was then purified by flash chromatography using 20% EtOAc/Hexane to afford 18 mg of 3 as a white solid. $^1$H NMR ($CDCl_3$, 400 MHz) δ: 5.29-5.22 (m, 1H); 3.28-3.18 (m, 1H); 2.80 d, 1H, J=4 Hz); 2.21 (d, 1H, J=11 Hz); 2.05-1.80 (m, 4H); 1.78-1.55 (m, 3H); 1.51-1.15 (m, 8H); 1.13-0.75 (m, 23H); 0.73 (s, 3H). ESI-TOF high acc m/z 477.3319 (M+Na$^+$, $C_{30}H_{46}O_3$ requires 477.3339).

To prepare 2β,3α-dihydroxy-12-ursen-28-oic acid (Compound 4; FIG. 6), a stirred solution of epoxide 3 (20 mg, 0.044 mmol) in 2 mL THF:$H_2O$ (9:1) was added d-10-camphorsulfonic acid (10 mg, 0.044 mmol). The reaction mixture was heated at 60° C. and stirred for 3 h. Triethylamine (0.1 mL) was added, the reaction mixture was diluted with EtOAc (5 mL) and extracted with 10% aqueous HCl solution. The organic layer was separated, dried ($Na_2SO_4$) and concentrated. The residue was then purified by flash chromatography (60% EtOAc/Hexane) to yield 8.4 mg (40%) of 4 as a white solid. $^1$H NMR ($MeOD_4$, 400 MHz) δ: 6.86-6.79 (m, 1 h); 5.41-5.32 (m, 1H); 5.15 (d, 1H, J=8 Hz); 3.78 (d, 1H, J=11 Hz); 3.68-3.42 (m, 4H); 3.19-2.81 (m, 11H); 2.72-2.4 (m, 23H); 2.38 (s, 3H). ESI-TOF high acc m/z 495.3349 (M+Na$^+$, $C_{30}H_{45}O_4$ requires 495.3445).

To prepare 2β-methoxy-3α-hydroxy-12-ursen-28-oic acid (Compound 5; FIG. 6), a stirred solution of epoxide 3 (30 mg, 0.066 mmol) in 3 mL $CH_2Cl_2$:MeOH (1:1) was added d-10-camphorsulfonic acid (15 mg, 0.066 mmol). The reaction mixture was heated at 60° C. and stirred for 3 h. Triethylamine (0.11 mL) was added, the reaction mixture was diluted with EtOAc (5 mL) and extracted with 10% aqueous HCl solution. The organic layer was separated, dried ($Na_2SO_4$) and concentrated. The residue was then purified by flash chromatography (30% EtOAc/Hexane) to yield 27 mg (85%) of 5 as a white solid. $^1$H NMR ($CDCl_3$, 400 MHz) δ: 5.29-5.26 (m, 1H); 3.68 (d, 1H, J=9 Hz); 3.40-3.29 (m, 4H); 2.21 (d, 1H, J=11 Hz); 2.08-1.82 (m, 4H); 1.78-1.63 (m, 3H); 1.60-1.19 (m, 8H); 1.18-0.80 (m, 23H); 0.73 (s, 3H). ESI-TOF high acc m/z 509.3590 (M+Na$^+$, $C_{31}H_{50}O_4$ requires 509.3601).

To prepare 2β-methoxy-3α-cinnamoyl-12-ursen-28-oic acid (Compound 6), Pyridine (40 μL, 0.48 mmol) was added to a solution of 5 (47 mg, 0.097 mmol) and cinnamoyl chloride (32 mg, 0.19 mmol) in dry $CH_2Cl_2$ (5 mL). The reaction mixture was stirred at room temperature for 6 h. Then, the reaction mixture was diluted with $CH_2Cl_2$ (10 mL) and extracted with 10% aqueous HCl solution (2×10 mL). The combined organic phases were dried (Na₂SO₄) and concentrated. The crude product was then purified by flash chromatography (30% EtOAc/Hexane) to afford of 6 as a white solid. ¹H NMR (CDCl₃, 400 MHz) δ: 7.92 (d, 1H, J=16 Hz); 7.61-7.52 (m, 2H); 7.50-7.35 (m, 3H); 6.45 (d, 1H, J=16 Hz); 5.42-5.38 (m, 1H); 3.70 (d, 1H, J=9 Hz); 3.43-3.32 (m, 1H); 2.30 (d, 1H, J=); 2.18-1.91 (m, 4H); 1.88-1.72 (m, 3H); 1.68-1.23 (m, 8H); 1.21-0.79 (m, 26H). ESI-TOF high acc m/z 639.4018 (M+Na⁺, C₄₀H₅₆O₅ requires 639.402).

Example 16

Inhibition of Biofilm Formation by Analogs with Either β or α Configurations at the C2 or C3 Positions: *Escherichia coli* Clinical Strain UTI89

Biofilm inhibition experiments were conducted using an assay adapted from the reported protocol described in Pratt and Kolter, 1998, Molecular Microbiology, 30: 285-293; Li et al., 2001, J. Bacteriol., 183: 897-908. *E. coli* clinical strain UTI89 was grown in LB in 96 well plates at room temperature for one day without shaking. To quantify the biofilm mass, the suspension culture was poured out and the biofilm was washed three times with water. The biofilm was stained with 0.1% crystal violet for 20 minutes. The plates were then washed three times with water. Then 95% ethanol was added to dissolve the dye at the bottom and on the wall and the OD reading at 540 nm was measured to quantify the total biofilm mass. Test compounds were added with the inoculation and biofilm mass was measured after one day as described above appropriate amounts of 100% ethanol were added to each sample to eliminate the effect of solvent. Each condition had 4 to 8 replicates on each plate and was performed over multiple days.

The compounds tested had no inhibitory effect on the growth of either strain of *E. coli* when compared to controls, demonstrating that these compounds are not antibacterial compounds. Pygenic acid B (2α,3α,24-trihydroxy-12-ursen-28-oic acid) inhibited biofilm formation of the UTI89 strain by about 80%, 53%, and 50% as compared to the controls at 32, 16, and 8 ug/ml, respectively. Pygenic acid C (1β,2α,3α,24-tetrahydroxy-12-ursen-28-oic acid) inhibited biofilm formation of the UTI89 strain by about 45% as compared to the controls at 32 ug/ml. Echinocystic acid (3β,16α-dihydroxy-olean-12-en-28-oic acid) inhibited biofilm formation of the UTI89 strain by about 80%, 50%, and 27% as compared to the controls at 32, 16, and 8 ug/ml, respectively. Corosolic acid (2α,3β-dihydroxy-12-ursen-28-oic acid) inhibited biofilm formation of the UTI89 strain by about 85% as compared to the controls at 20 ug/ml. 2β-methoxy-3α-cinnamoyl-12-ursen-28-oic acid, 3β-O-tert-butyloxycarbonyl-ursolic acid, 2β-methoxy-3α-hydroxy-12-ursen-28-oic acid, and 2β,3α-dihydroxy-12-ursen-28-oic acid inhibited biofilm formation of the UTI89 strain as compared to the controls by about 40%, 46%, 38%, and 62%, respectively, at 32 ug/ml. These four compounds were synthetically prepared according to the methods in Figure X. These experiments confirm that compounds of the invention isolated from plants or prepared synthetically by the methods listed in the specification and exhibiting different β or α configurations at C-2 or C-3 inhibit the formation of biofilms against clinical strains of *E. coli*. The comparison of Corosolic acid (2α,3β-dihydroxy-12-ursen-28-oic acid; 85% inhibition at 20 ug/ml) and 2β,3α-dihydroxy-12-ursen-28-oic acid (62% inhibition at 32 ug/ml) also demonstrates that the 2α,3β configuration provides increased biofilm inhibition relative to the 2β,3α configuration when R¹ and R² of the ursane scaffold are hydroxy.

What is claimed:
1. A compound corresponding to the following chemical structure:

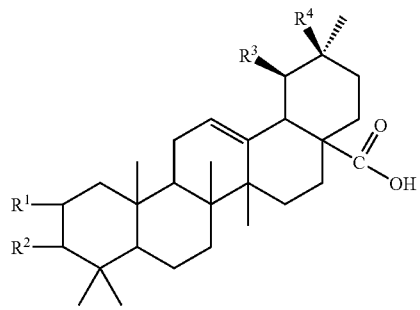

wherein:
R¹ is selected from the group consisting of hydrogen, hydroxyl, halide, methoxy, acetoxy, —CH₂OH, —CH₂CH₂OH, —CN, —C₁₋₂(halo)alkyl, —CH₂Cl, —C(O)H, —C(O)NH₂, —SH, CF₃, CCl₃, and —NAA, wherein each A is independently selected from the group consisting of H and C₁-C₂ alkyl;
R² is selected from the group consisting of hydroxyl, halide, —CN, —C(O)NH₂, —SH, —S(O)NH₂, CF₃, CCl₃, —NYY wherein each Y is independently selected from H and C₁-C₅ alkyl, C₁₋₅ acyl halides, —C₁₋₅(halo)alkyl, C₁₋₅ acyl residues, C₂₋₅ secondary amides, (C₁₋₅)(C₁₋₅)tertiary amides, C₁₋₅ alcohols, C₁₋₅ substituted alkyls, C₂₋₅ alkenyls, C₂₋₅substituted alkenyls, —OC(O)—OC(CH₃)₃, —OC(O)—CH=CH-phenyl, —OC(O)—R, wherein R is an unbranched or branched C₁-C₅ alkyl, and —OC(O)C₁₋₅R⁵R⁶ wherein R⁵ is an alkylene or alkenylene of up to 5 carbons and R⁶ is selected from the group consisting of substituted and unsubstituted C₅₋₇ aromatics, substituted and unsubstituted C₅₋₇ cycloalkyls, and substituted and unsubstituted C₅₋₇ heterocycloalkyls; provided that:
 i) R² is not hydroxyl when R¹ is hydrogen, hydroxyl, methoxy, chloride or —CN;
 ii) R² is not chloride or —OC(O)CH₃ when R¹ is hydrogen;
 iii) R² is not —OC(O)—CH=CH-(m-hydroxy, p-methoxy-phenyl) or —OC(O)—CH=CH-(p-hydroxy-phenyl) when R¹ is hydroxyl; and
 iv) R² is not C₁₋₅ substituted alkyl, —C₁₋₅(halo)alkyl, or C₁₋₅, alcohol when R¹ is hydrogen, halide, hydroxyl, methoxy, acetoxy or —SH;
one of R³ and R⁴ is hydrogen and the other is methyl; and
R¹ is in the β stereochemical configuration and R² is in the α stereochemical configuration;
and salts, hydrates, solvates, prodrugs and N-oxides thereof.

2. The compound of claim 1, wherein said compound contains a C-28 carboxyl group and wherein said prodrug of said compound is selected from the group consisting of esters, amides, and hydrazides of said C-28 carboxyl group.

3. The compound of claim 1 wherein the compound is not a salt, hydrate, solvate, prodrug or N-oxide of the chemical structure.

4. A method for treating, controlling, reducing or inhibiting a bacterial infection in a subject in need thereof by administering to the subject an effective amount of a composition comprising a compound having the following chemical structure:

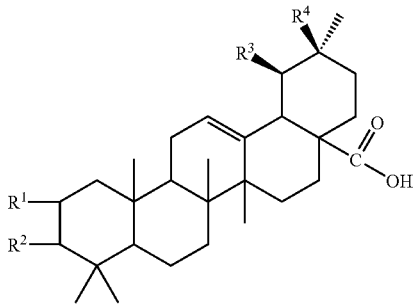

wherein:
R¹ is selected from the group consisting of hydrogen, hydroxyl, halide, methoxy, acetoxy, —CH₂OH, —CH₂CH₂OH, —CN, —C₁₋₂(halo)alkyl, —CH₂Cl, —C(O)H, —C(O)NH₂, —SH, CF₃, CCl₃, and —NAA, wherein each A is independently selected from the group consisting of H and C₁-C₂ alkyl;
R² is selected from the group consisting of hydroxyl, halide, —CN, —C(O)NH₂, —SH, —S(O)NH₂, CF₃, CCl₃, —NYY wherein each Y is independently selected from H and C₁-C₅ alkyl, C₁₋₅ acyl halides, —C₁₋₅(halo)alkyl, C₁₋₅ acyl residues, C₂₋₅ secondary amides, (C₁₋₅)(C₁₋₅)tertiary amides, C₁₋₅ alcohols, C₁₋₅ substituted alkyls, C₂₋₅ alkenyls, C₂₋₅ substituted alkenyls, —OC(O)—OC(CH₃)₃, —OC(O)—CH=CH-phenyl, —OC(O)—R, wherein R is an unbranched or branched C₁-C₅ alkyl, and —OC(O)C₁₋₅R⁵R⁶ wherein R⁵ is an alkylene or alkenylene of up to 5 carbons and R⁶ is selected from the group consisting of substituted and unsubstituted C₅₋₇ aromatics, substituted and unsubstituted C₅₋₇ cycloalkyls, and substituted and unsubstituted C₅₋₇ heterocycloalkyls; provided that:
i) R² is not hydroxyl when R¹ is hydrogen or hydroxyl;
ii) R² is not —OC(O)CH₃ when R¹ is hydrogen; and
iii) R² is not —OC(O)—CH=CH-(m-hydroxy, p-methoxy-phenyl) or —OC(O)—CH=CH-(p-hydroxy-phenyl) when R¹ is hydroxyl;
one of R³ and R⁴ is hydrogen and the other is methyl;
and salts, hydrates, solvates, prodrugs and N-oxides thereof;
and an acceptable carrier, thereby treating, controlling, reducing or inhibiting the bacterial infection.

5. The method of claim 4, wherein R¹ is in the β stereochemical configuration and R² is in the α stereochemical configuration.

6. The method of claim 4, wherein R¹ is in the α stereochemical configuration and R² is in the β stereochemical configuration.

7. The method of claim 4, wherein the composition is administered to the subject orally, topically, rectally, percutaneously, by parenteral injection, intranasally or by inhalation.

8. The method of claim 7, wherein the infection is a chronic bacterial infection.

9. The method of claim 8, wherein the chronic bacterial infection is selected from the group consisting of urinary tract infection, gastritis, lung infection, ear infection, cystitis, pyelonephritis, arterial damage, leprosy, tuberculosis, benign prostatic hyperplasia, prostatitis, osteomyelitis, bloodstream infection, cirrhosis, skin infection, acne, rosacea, open wound infection, atopic dermatitis, chronic wound infection, and sinus infection.

10. The method of claim 9, wherein the chronic bacterial infection causes an autoimmune disease.

11. The method of claim 4, wherein the subject is a mammal and the carrier is a pharmaceutically acceptable carrier.

12. The method of claim 11, wherein the mammal is a human.

13. The method of claim 4, wherein the composition further comprises an antimicrobial agent.

14. The method of claim 13, wherein the antimicrobial agent is an antibiotic.

15. The method of claim 14, wherein the antibiotic is selected from the group consisting of tobramycin, clindamycin, ciprofloxacin, tetracyclines, rifampin, triclosan, oxfloxacin, macrolides, penicillins, cephalosporins, amoxicillin/clavulanate, quinupristin/dalfopristin, amoxicillin/sulbactum, metronidazole, fluoroquinolones, quinolones, ketolides, or aminoglycosides.

16. A compound corresponding to the following chemical structure:

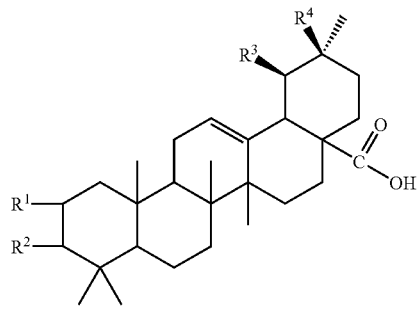

wherein R¹ is selected from the group consisting of C₁ alcohol, —C₁(chloro)alkyl, —C(O)H, —C(O)NH₂, and —NH₂, R² is hydroxyl, and one of R³ and R⁴ is hydrogen and the other is methyl; and salts, hydrates, solvates, prodrugs and N-oxides thereof.

17. A compound corresponding to the following chemical structure:

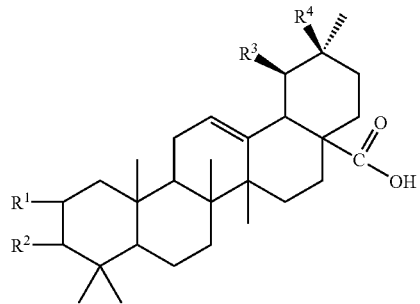

wherein R¹ is selected from the group consisting of fluoro, chloro, —C(O)H, —C(O)NH₂, —SH and —NH₂, and R² is selected from the group consisting of hydroxyl, halide, —CN, —C(O)NH₂, —SH, —S(O)NH₂, CF₃, CCl₃, NYY, wherein each Y is independently selected from H and C₁-C₅ alkyl, C₁₋₅ acyl halides, —C₁₋₅(halo)alkyl, C₁₋₅ acyl residues, C₂₋₅ secondary amides, (C₁₋₅) tertiary amides, C₁₋₅ alcohols, C₁₋₅ substituted alkyls, $C_{2-5}$ alkenyls, $C_{2-5}$ substituted alkenyls, —OC(O)—OC($CH_3$)$_3$, —OC(O)—CH=CH-phenyl, —OC(O)—R, wherein R is an unbranched or branched $C_1$-$C_5$ alkyl, and —OC(O)$C_{1-5}R^5R^6$ wherein $R^5$ is an alkylene or alkenylene of up to 5 carbons and $R^6$ is selected from the group consisting of substituted and unsubstituted $C_{5-7}$ aromatics, substituted and unsubstituted $C_{5-7}$ cycloalkyls, and substituted and unsubstituted $C_{5-7}$ heterocycloalkyls; provided that $R^2$ is not $C_{1-5}$ substituted alkyl, —$C_{1-5}$(halo)alkyl, or $C_{1-5}$ alcohol when $R^1$ is —SH; and one of $R^3$ and $R^4$ is hydrogen and the other is methyl; and salts, hydrates, solvates, prodrugs and N-oxides thereof.

18. A compound corresponding to the following chemical structure:

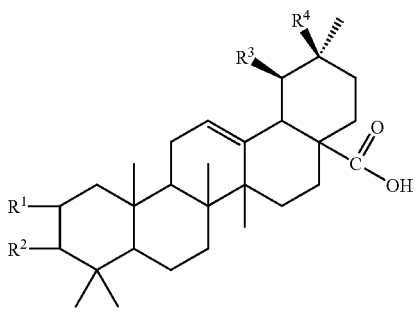

wherein $R^2$ is selected from the group consisting of —C(O)H, —C(O)$NH_2$, —$NH_2$ and —SH, $R^1$ is hydroxyl, and one of $R^3$ and $R^4$ is hydrogen and the other is methyl; and salts, hydrates, solvates, prodrugs and N-oxides thereof.

19. A composition comprising a compound corresponding to the following structure:

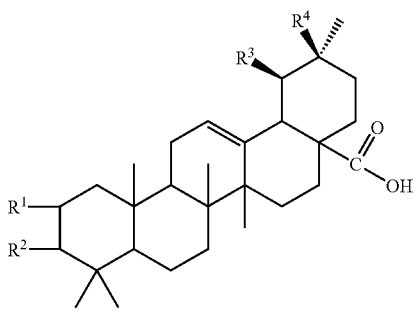

wherein:
$R^1$ is selected from the group consisting of hydrogen, hydroxyl, halide, methoxy, acetoxy, —$CH_2$OH, —$CH_2CH_2$OH, —CN, —$C_{1-2}$(halo)alkyl, —CH, Cl, —C(O)H, —C(O)$NH_2$, —SH, $CF_3$, $CCl_3$, and —NAA, wherein each A is independently selected from the group consisting of H and $C_1$-$C_2$ alkyl;
$R^2$ is selected from the group consisting of hydroxyl, halide, —CN, —C(O)$NH_2$, —SH, —S(O)$NH_2$, $CF_3$, $CCl_3$, —NYY wherein each Y is independently selected from H and $C_1$-$C_5$ alkyl, $C_{1-5}$ acyl halides, —$C_{1-5}$(halo)alkyl, $C_{1-5}$ acyl residues, $C_{2-5}$ secondary amides, ($C_{1-5}$) ($C_{1-5}$)tertiary amides, $C_{1-5}$ alcohols, $C_{1-5}$ substituted alkyls, $C_{2-5}$ alkenyls, $C_{2-5}$ substituted alkenyls, —OC(O)—OC($CH_3$)$_3$, —OC(O)—CH=CH-phenyl, —OC(O)—R, wherein R is an unbranched or branched $C_1$-$C_5$ alkyl, and —OC(O) $C_{1-5}R^5R^6$ wherein $R^5$ is an alkylene or alkenylene of up to 5 carbons and $R^6$ is selected from the group consisting of substituted and unsubstituted $C_{5-7}$ aromatics, substituted and unsubstituted $C_{5-7}$ cycloalkyls, and substituted and unsubstituted $C_{5-7}$ heterocycloalkyls; provided that:
 i) $R^2$ is not hydroxyl when $R^1$ is hydrogen, hydroxyl, methoxy, chloride or —CN;
 ii) $R^2$ is not chloride or —OC(O)$CH_3$ when $R^1$ is hydrogen;
 iii) $R^2$ is not —OC(O)—CH=CH-(m-hydroxy, p-methoxy-phenyl) or —OC(O)—CH=CH-(p-hydroxy-phenyl) when $R^1$ is hydroxyl; and
 iv) $R^2$ is not $C_{1-5}$ substituted alkyl, —$C_{1-5}$(halo)alkyl, or $C_{1-5}$ alcohol when $R^1$ is hydrogen, halide, hydroxyl, methoxy, acetoxy or —SH;
one of $R^3$ and $R^4$ is hydrogen and the other is methyl; and
$R^1$ is in the β stereochemical configuration and $R^2$ is in the α stereochemical configuration;
and salts, hydrates, solvates, prodrugs and N-oxides thereof;
and a pharmaceutically acceptable carrier.

20. The composition of claim 19, wherein the composition is a racemic mixture of the compound and its isomer wherein $R^1$ is in the α stereochemical configuration and $R^2$ is in the β stereochemical configuration.

21. The composition of claim 19, wherein the pharmaceutically acceptable carrier permits administration of the pharmaceutical composition orally, topically, rectally, percutaneously, by parenteral injection, intranasally or by inhalation.

22. The composition of claim 21, wherein the composition is a topical preparation.

23. The composition of claim 21, wherein the topical preparation is a gel, cream, emollient, or soap.

24. The composition of claim 19, wherein the composition is a dentifrice.

25. The composition of claim 24, wherein the dentifrice is selected from the group consisting of toothpaste, toothpowder, liquid dentifrice, mouth detergent, mouthwash, troches, chewing gum, dental or gingival massage cream, dental strip, dental gel, and gargle tablet.

26. The composition of claim 25, wherein the dentifrice is a tooth paste and further comprises a tooth or gum adherence promoting substance selected from the group consisting of copolymers of methyl vinyl ether and maleic anhydride, copolymers of vinyl pyrrolidone and vinyl acetate, and cyclodextrins.

27. The composition of claim 25, further comprising an antimicrobial agent selected from the group consisting of triclosan, metronidazole, tetracyclines, quinolones, plant essential oils, camphor, thymol, carvacrol, menthol, eucalyptol, and methyl salicylate.

28. The composition of claim 19 wherein the composition is a pharmaceutical composition.

29. The composition of claim 28, wherein $R^1$ is in the α stereochemical configuration and $R^2$ is in the β stereochemical configuration.

30. The composition of claim 28, wherein the pharmaceutically acceptable carrier permits administration of the pharmaceutical composition orally, topically, rectally, percutaneously, by parenteral injection, intranasally or by inhalation.

31. The composition of claim 28, further comprising an antimicrobial agent selected from the group consisting of triclosan, metronidazole, tetracyclines, quinolones, plant essential oils, camphor, thymol, carvacrol, menthol, eucalyptol, and methyl salicylate.

32. The composition of claim 28, further comprising an antimicrobial agent an antibiotic.

33. The composition of claim 32, wherein the antibiotic is selected from the group consisting of tobramycin, clindamycin, ciprofloxacin, tetracyclines, rifampin, triclosan, oxfloxacin, macrolides, penicillins, cephalosporins, amoxicillin/clavulanate, quinupristin/dalfopristin, amoxicillin/sulbactum, metronidazole, fluoroquinolones, quinolones, ketolides, or aminoglycosides.

34. The composition of claim 19 wherein the compound is not a salt, hydrate, solvate, prodrug or N-oxide of the chemical structure.

35. A composition comprising an antimicrobial agent and a compound corresponding to the following chemical structure:

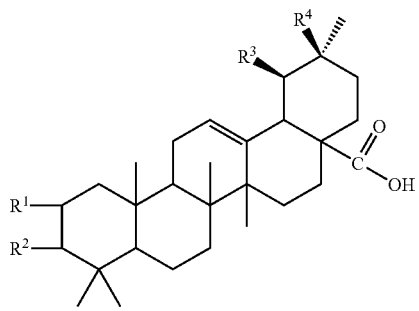

wherein:

$R^1$ is selected from the group consisting of hydrogen, hydroxyl halide, methoxy, acetoxy, —$CH_2$ OH, —$CH_2CH_2OH$, —CN, —$C_{1-2}$(halo)alkyl, —$CH_2Cl$, —C(O)H, —C(O)$NH_{22}$, —SH, $CF_3$, $CCl_3$, and —NAA, wherein each A is independently selected from the group consisting of H and $C_1$-$C_2$ alkyl;

$R^2$ is selected from the group consisting of hydroxyl, halide, —CN, —C(O)$NH_2$, —SH, —S(O)$NH_2$, $CF_3$, $CCl_3$, —NYY wherein each Y is independently selected from H and $C_1$-$C_5$ alkyl, $C_{1-5}$ acyl halides, —$C_{1-5}$(halo)alkyl, $C_{1-5}$ acyl residues, $C_{2-5}$ secondary amides, ($C_{1-5}$) ($C_{1-5}$)tertiary amides, $C_{1-5}$ alcohols, $C_{1-5}$ substituted alkyls, $C_{2-5}$ alkenyls, $C_{2-5}$ substituted alkenyls, —OC(O)—OC($CH_3$)$_3$, —OC(O)—CH=CH-phenyl, —OC(O)—R, wherein R is an unbranched or branched $C_1$-$C_5$ alkyl, and —OC(O) $C_{1-5}R^5R^6$ wherein $R^5$ is an alkylene or alkenylene of up to 5 carbons and $R^6$ is selected from the group consisting of substituted and unsubstituted $C_{5-7}$ aromatics, substituted and unsubstituted $C_{5-7}$ cycloalkyls, and substituted and unsubstituted $C_{5-7}$ heterocycloalkyls; provided that:

i) $R^2$ is not hydroxyl when $R^1$ is hydrogen, hydroxyl, methoxy, chloride or —CN;
  ii) $R^2$ is not chloride or —OC(O)$CH_3$ when $R^1$ is hydrogen;
  iii) $R^2$ is not —OC(O)—CH=CH-(m-hydroxy, p-methoxy-phenyl) or —OC(O)—CH=CH-(p-hydroxy-phenyl) when $R^1$ is hydroxyl; and
  iv) $R^2$ is not $C_{1-5}$ substituted alkyl, —$C_{1-5}$(halo)alkyl, or $C_{1-5}$ alcohol when $R^1$ is hydrogen, halide, hydroxyl, methoxy, acetoxy or —SH;

one of $R^3$ and $R^4$ is hydrogen and the other is methyl; and salts, hydrates solvates, prodrugs and N-oxides thereof.

36. The composition of claim 21, wherein the antimicrobial agent is an antibiotic.

37. The composition of claim 22, wherein the antibiotic is selected from the group consisting of tobramycin, clindamycin, ciprofloxacin, tetracyclines, rifampin, triclosan, oxfloxacin, macrolides, penicillins, cephalosporins, amoxicillin/clavulanate, quinupristin/dalfopristin, amoxicillin/sulbactum, metronidazole, fluoroquinolones, quinolones, ketolides, or aminoglycosides.

38. The composition of claim 37, wherein the composition comprises about 0.1% to about 20.0% of the compound.

39. The composition of claim 38, wherein the composition comprises about 0.1% to about 5.0% of the compound.

40. The composition of claim 39, wherein the composition comprises about 2% of the compound.

41. A method for inhibiting or reducing a biofilm comprising contacting the biofilm or a cell capable of biofilm formation with an effective amount of a composition comprising a compound corresponding to the following chemical structure:

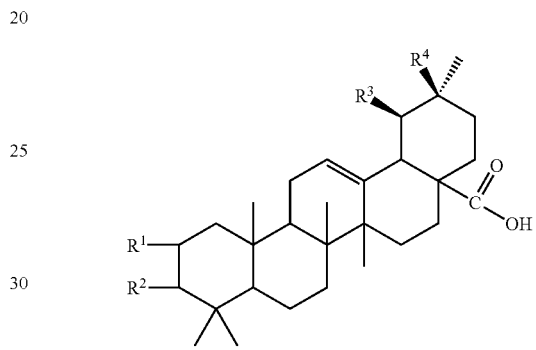

wherein:

$R^1$ is selected from the group consisting of hydrogen, hydroxyl, halide, methoxy, acetoxy, —$CH_2$ OH, —$CH_2CH_2OH$, —CN, —$C_{1-2}$(halo)alkyl, —$CH_2Cl$, —C(O)H, —C(O)$NH_2$, —SH, $CF_3$, $CCl_3$, and —NAA, wherein each A is independently selected from the group consisting of H and $C_1$-$C_2$ alkyl;

$R^2$ is selected from the group consisting of hydroxyl, halide, —CN, —C(O)$NH_2$, —SH, —S(O)$NH_2$, $CF_3$, $CCl_3$, —NYY wherein each Y is independently selected from H and $C_{1-5}$ alkyl, $C_{1-5}$ acyl halides, —$C_{1-5}$(halo)alkyl, $C_{1-5}$ acyl residues, $C_{2-5}$ secondary amides, ($C_{1-5}$) ($C_{1-5}$)tertiary amides, $C_{1-5}$ alcohols, $C_{1-5}$ substituted alkyls, $C_{2-5}$, alkenyls, $C_{2-5}$ substituted alkenyls, —OC(O)—OC($CH_3$)$_3$, —OC(O)—CH=CH-phenyl, —OC(O)—R, wherein R is an unbranched or branched $C_1$-$C_5$ alkyl, and —OC(O)$C_{1-5}R^5R^6$ wherein $R^5$ is an alkylene or alkenylene of up to 5 carbons and $R^6$ is selected from the group consisting of substituted and unsubstituted $C_{5-7}$ aromatics, substituted and unsubstituted $C_{5-7}$ cycloalkyls, and substituted and unsubstituted $C_{5-7}$ heterocycloalkyls; provided that:

i) $R^2$ is not hydroxyl when $R^1$ is hydrogen or hydroxyl;
  ii) $R^2$ is not —OC(O)$CH_3$ when $R^1$ is hydrogen; and
  iii) $R^2$ is not —OC(O)—CH=CH-(m-hydroxy, p-methoxy-phenyl) or —OC(O)—CH=CH-(p-hydroxy-phenyl) when $R^1$ is hydroxyl;

one of $R^3$ and $R^4$ is hydrogen and the other is methyl;

and salts, hydrates, solvates, prodrugs and N-oxides thereof;

and an acceptable carrier, thereby preventing, inhibiting or reducing the biofilm or its formation.

42. The method of claim 41, wherein the biofilm or biofilm formation is prevented, inhibited or reduced in vivo and the acceptable carrier is a pharmaceutically acceptable carrier.

43. The method of claim 41, wherein the biofilm or biofilm formation is inhibited or prevented on a substrate.

44. The method of claim 43, wherein the substrate is a biological structure selected from the group consisting of a regenerating protein of a mammalian cellular membranes, dental enamel, gum, tongue, and biological polymer.

45. The method of claim 43, wherein the substrate is a medical device selected from the group consisting of a central venous catheter, urinary catheter, endotracheal tube, mechanical heart valve, pacemaker, vascular graft, stent, and prosthetic joint.

46. The method of claim 33, wherein the prevention, inhibition or reduction of biofilm formation is effected in a vessel hull, car, airplane, industrial equipment, device, membrane, filter, microtiter plate, continuous flow chamber, or piece of machinery.

47. The method of claim 41, wherein the biofilm or cell capable of biofilm formation is associated with a respiratory infection and wherein the biofilm or a cell capable of biofilm formation is contacted by administering the composition by an inhaler or nebulizer.

48. The method of claim 47, wherein the respiratory infection occurs in a patient with cystic fibrosis.

49. The method of claim 41, wherein the composition further comprises an antimicrobial agent.

50. The method of claim 49, wherein the antimicrobial agent is an antibiotic.

51. The method of claim 50, wherein the antibiotic is selected from the group consisting of tobramycin, clindamycin, ciprofloxacin, tetracyclines, rifampin, triclosan, oxfloxacin, macrolides, penicillins, cephalosporins, amoxicillin/clavulanate, quinupristin/dalfopristin, amoxicillin/sulbactum, metronidazole, fluoroquinolones, quinolones, ketolides, or aminoglycosides.

52. The method of claim 41 wherein the compound is not a salt, hydrate, solvate, prodrug or N-oxide of the chemical structure.

53. A compound corresponding to the following chemical structure:

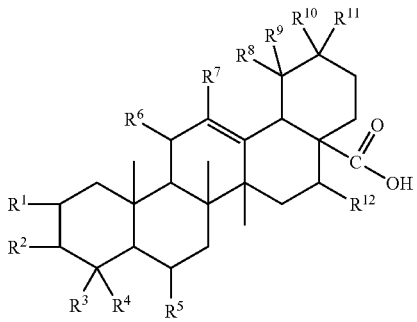

wherein:
$R^1$ is selected from the group consisting of hydrogen, hydroxyl, halide, methoxy, acetoxy, —$CH_2$OH, —$CH_2CH_2$OH, —CN, —$C_{1-2}$(halo)alkyl, —$CH_2$Cl, —C(O)H, —C(O)$NH_2$, —SH, $CF_3$, $CCl_3$, and —NAA, wherein each A is independently selected from the group consisting of H and $C_1$-$C_2$ alkyl;
$R^2$ is selected from the group consisting of hydroxyl, halide, —CN, —C(O)$NH_2$, —SH, —S(O)$NH_2$, $CF_3$, $CCl_3$, —NYY wherein each Y is independently selected from H and $C_1$-$C_5$ alkyl, $C_{1-5}$ acyl halides, —$C_{1-5}$(halo)alkyl, $C_{1-5}$ acyl residues, $C_{2-5}$ secondary amides, ($C_{1-5}$)($C_{1-5}$)tertiary amides, $C_{1-5}$ alcohols, $C_{1-5}$ substituted alkyls, $C_{2-5}$ alkenyls, $C_{2-5}$ substituted alkenyls, substituted or unsubstituted $C_{5-7}$ aromatics, —OC(O)—OC($CH_3$)$_3$, —OC(O)—CH=CH-phenyl, —OC(O)—R, wherein R is an unbranched or branched $C_1$-$C_5$ alkyl, and —OC(O)$C_{1-5}R^{13}R^{14}$ wherein $R^{13}$ is an alkylene or alkenylene of up to 5 carbons and $R^{14}$ is selected from the group consisting of substituted and unsubstituted $C_{5-7}$ aromatics, substituted and unsubstituted $C_{5-7}$ cycloalkyls, and substituted and unsubstituted $C_{5-7}$ heterocycloalkyls; wherein $R^1$ is in the β stereochemical configuration and $R^2$ is in the α stereochemical configuration and provided that:
i) $R^2$ is not hydroxyl when $R^1$ is hydrogen, hydroxyl, methoxy, chloride or —CN;
ii) $R^2$ is not chloride or —OC(O)$CH_3$ when $R^1$ is hydrogen;
iii) $R^2$ is not —OC(O)—CH=CH-(m-hydroxy, p-methoxy-phenyl) or —OC(O)—CH=CH-(p-hydroxy-phenyl) when $R^1$ is hydroxyl; and
iv) $R^2$ is not $C_{1-5}$ substituted alkyl, —$C_{1-5}$(halo)alkyl, or $C_1$—, alcohol when $R^1$ is hydrogen, halide, hydroxyl, methoxy, acetoxy or —SH;
$R^3$ is selected from the group consisting of hydrogen, methyl, halide, and —$NH_2$;
$R^4$ is selected from the group consisting of hydrogen, methyl, hydroxyl, halide, $C_{1-3}$ alkoxy, —CN, —$NH_2$, —C(O)H, —C(O)$NH_2$, —SH, —S(O)$NH_2$, carboxylic acid groups, $C_{1-3}$ acyl halides, $C_{1-3}$ acyl residues, $C_{2-3}$ secondary amides, $C_{1-3}$ alcohols, ($C_{1-2}$)($C_{1-2}$) ethers, $C_{2-3}$ alkyls, $C_{1-3}$ substituted alkyls, $C_{2-3}$ alkenyls, and $C_{2-3}$ substituted alkenyls;
$R^5$, and $R^{12}$ are independently selected from the group consisting of hydrogen, hydroxyl, halide, $C_{1-3}$ alkoxy, —CN, —$NH_2$, —C(O)$NH_2$, —OC(O)$C_{1-3}$, —SH, —S(O)$NH_2$, and —$C_{1-3}$(halo)alkyl;
$R^6$ and $R^7$ are independently is selected from the group consisting of hydrogen, hydroxyl, halide, and —$NH_2$;
one of $R^8$ and $R^{10}$ is hydrogen and the other is methyl;
$R^9$ and $R^{11}$ are independently selected from the group consisting of hydrogen, methyl, hydroxyl, halide, $C_{1-3}$ alkoxy, —NH2, and —CN;
and salts, hydrates, solvates, prodrugs and N-oxides thereof.

54. The compound of claim 53, wherein the compound is part of a racemic mixture.

55. A compound corresponding to the following chemical structure:

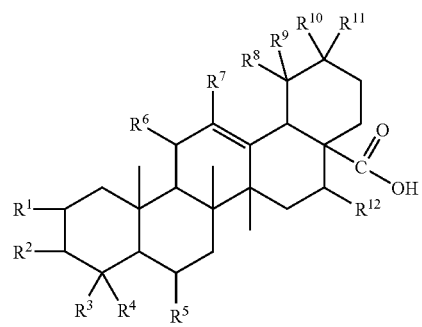

wherein:

$R^1$ is selected from the group consisting of $C_1$ alcohol, —$C_1$ (chloro)alkyl, —C(O)H, —C(O)NH$_2$, and —NH$_2$, $R^2$ is hydroxyl;

$R^3$ is selected from the group consisting of hydrogen, methyl, halide, and —NH$_2$;

$R^4$ is selected from the group consisting of hydrogen, methyl, hydroxyl, halide, $C_{1-3}$ alkoxy, —CN, —NH$_2$, —C(O)H, —C(O)NH$_2$, —SH, —S(O)NH$_2$, carboxylic acid groups, $C_{1-3}$ acyl halides, $C_{1-3}$ acyl residues, $C_{2-3}$ secondary amides, $C_{1-3}$ alcohols, $(C_{1-2})(C_{1-2})$ ethers, $C_{2-3}$ alkyls, $C_{1-3}$ substituted alkyls, $C_{2-3}$ alkenyls, and $C_{2-3}$ substituted alkenyls;

$R^5$, and $R^{12}$ are independently selected from the group consisting of hydrogen, hydroxyl, halide, $C_{1-3}$ alkoxy, —CN, —NH$_2$, —C(O)NH$_2$, —OC(O)C$_{1-3}$, —SH, —S(O)NH$_2$, and —C$_{1-3}$(halo)alkyl;

$R^6$ and $R^7$ are independently is selected from the group consisting of hydrogen, hydroxyl, halide, and —NH$_2$;

one of $R^8$ and $R^{10}$ is hydrogen and the other is methyl;

$R^9$ and $R_{11}$ are independently selected from the group consisting of hydrogen, methyl, hydroxyl, halide, $C_{1-3}$ alkoxy, —NH$_2$, and —CN;

and salts, hydrates, solvates, prodrugs and N-oxides thereof.

56. A compound corresponding to the following chemical structure:

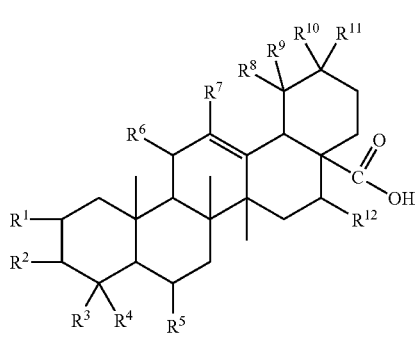

wherein:

$R^1$ is selected from the group consisting of fluoro, chloro, —C(O)H, —C(O)NH$_2$, —SH and —NH$_2$;

$R^2$ is selected from the group consisting of hydroxyl, halide, —CN, —C(O)NH$_2$, —SH, —S(O)NH$_2$, CF$_3$, CCl$_3$, —NYY, wherein each Y is independently selected from H and $C_1$-$C_5$alkyl, $C_{1-5}$ acyl halides, —$C_{1-5}$(halo)alkyl, $C_{1-5}$ acyl residues, $C_{1-5}$ secondary amides, $(C_{1-5})$tertiary amides, $C_{1-5}$ alcohols, $C_{1-5}$ substituted alkyls, $C_{2-5}$ alkenyls, $C_{2-5}$ substituted alkenyls, substituted or unsubstituted $C_{5-7}$ aromatics, —OC(O)—OC(CH$_3$)$_3$, —OC(O)—CH=CH-phenyl, —OC(O)—R, wherein R is an unbranched or branched $C_1$-$C_5$ alkyl and —OC(O)C$_{1-5}$R$^{13}$R$^{14}$ wherein R$^{13}$ is an alkylene or alkenylene of up to 5 carbons and R$^{14}$ is selected from the group consisting of substituted and unsubstituted $C_{5-7}$ aromatics, substituted and unsubstituted $C_{5-7}$ cycloalkyls, and substituted and unsubstituted $C_{5-7}$ heterocycloalkyls; provided that $R^2$ is not $C_{1-5}$ substituted alkyl, —$C_{1-5}$(halo)alkyl, or $C_{1-5}$ alcohol when $R^1$ is —SH;

$R^3$ is selected from the group consisting of hydrogen, methyl, halide, and —NH$_2$;

$R^4$ is selected from the group consisting of hydrogen, methyl, hydroxyl, halide, $C_{1-3}$ alkoxy, —CN, —NH$_2$, —C(O)H, —C(O)NH$_2$, —SH, —S(O)NH$_2$, carboxylic acid groups, $C_{1-3}$ acyl halides, $C_{1-3}$ acyl residues, $C_{2-3}$ secondary amides, $C_{1-3}$ alcohols, $(C_{1-2})(C_{1-2})$ ethers, $C_{2-3}$ alkyls, $C_{1-3}$ substituted alkyls, $C_{2-3}$ alkenyls, and $C_{2-3}$ substituted alkenyls;

$R^5$, and $R^{12}$ are independently selected from the group consisting of hydrogen, hydroxyl, halide, $C_{1-3}$ alkoxy, —CN, —NH$_2$, —C(O)NH$_2$, —OC(O)C$_{1-3}$, —SH, —S(O)NH$_2$, and —C$_{1-3}$(halo)alkyl;

$R^6$ and $R^7$ are independently is selected from the group consisting of hydrogen, hydroxyl, halide, and —NH$_2$;

one of $R^8$ and $R^{10}$ is hydrogen and the other is methyl;

$R^9$ and $R^{11}$ are independently selected from the group consisting of hydrogen, methyl, hydroxyl, halide, $C_{1-3}$ alkoxy, —NH$_2$, and —CN;

and salts, hydrates, solvates, prodrugs and N-oxides thereof.

57. A compound corresponding to the following chemical structure:

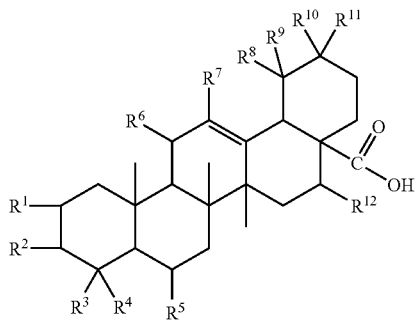

wherein:

$R^1$ is hydroxyl;

$R^2$ is selected from the group consisting of —C(O)H, —C(O)NH$_2$, —NH$_2$ and —SH;

$R^3$ is selected from the group consisting of hydrogen, methyl, halide, and —NH$_2$;

$R^4$ is selected from the group consisting of hydrogen, methyl, hydroxyl, halide, $C_{1-3}$ alkoxy, —CN, —NH$_2$, —C(O)H, —C(O)NH$_2$, —SH, —S(O)NH$_2$, carboxylic acid groups, $C_{1-3}$ acyl halides, $C_{1-3}$ acyl residues, $C_{2-3}$ secondary amides, $C_{1-3}$ alcohols, $(C_{1-2})(C_{1-2})$ ethers, $C_{2-3}$ alkyls, $C_{1-3}$ substituted alkyls, $C_{2-3}$ alkenyls, and $C_{2-3}$ substituted alkenyls;

$R^5$, and $R^{12}$ are independently selected from the group consisting of hydrogen, hydroxyl, halide, $C_{1-3}$ alkoxy, —CN, —NH$_2$, —C(O)NH$_2$, —OC(O)C$_{1-3}$, —SH, —S(O)NH$_2$, and —C$_{1-3}$(halo)alkyl;

$R^6$ and $R^7$ are independently is selected from the group consisting of hydrogen, hydroxyl, halide, and —NH$_2$;

one of $R^8$ and $R^{10}$ is hydrogen and the other is methyl;

$R^9$ and $R^{11}$ are independently selected from the group consisting of hydrogen, methyl, hydroxyl, halide, $C_{1-3}$ alkoxy, —NH$_2$, and —CN;

and salts, hydrates, solvates, prodrugs and N-oxides thereof.

* * * * *

UNITED STATES PATENT AND TRADEMARK OFFICE
CERTIFICATE OF CORRECTION

PATENT NO. : 7,612,045 B2  Page 1 of 1
APPLICATION NO. : 11/662806
DATED : November 3, 2009
INVENTOR(S) : Gary R. Eldridge It is certified that error appears in the above-identified patent and that said Letters Patent is hereby corrected as shown below:

Column 70, Line 66, should read "alkyl, $C_{1-5}$ acyl residues, $C_{2-5}$ secondary amides, $(C_{1-5})\underline{(C_{1-5})}$"

Column 73, Line 2, should read "antimicrobial agent $\underline{is}$ an antibiotic."

Column 74, Line 66, should read "and an acceptable carrier, thereby ~~preventing,~~ inhibiting or"

Column 75, Line 2, should read "formation is ~~prevented,~~ inhibited or reduced in vivo and the"

Column 75, Line 5, should read "formation is inhibited or ~~prevented~~ reduced on a substrate"

Column 75, Line 15, should read "The method of claim 33, where the ~~prevention~~, inhi-"

Column 78, Line 7, should read "$(C_{1-2})(C_{1-2})$ ethers,"

Signed and Sealed this

Fifth Day of January, 2010

David J. Kappos
*Director of the United States Patent and Trademark Office*